US011912712B2

(12) United States Patent
Cao et al.

(10) Patent No.: US 11,912,712 B2
(45) Date of Patent: Feb. 27, 2024

(54) ORGANIC ELECTROLUMINESCENT ELEMENT HAVING AN ORGANIC COMPOUND

(71) Applicant: BEIJING BAYI SPACE LIQUID CRYSTAL TECHNOLOGY CO. LTD., Beijing (CN)

(72) Inventors: Jianhua Cao, Beijing (CN); Weidong Jiang, Beijing (CN); Youwen Cheng, Beijing (CN); Chenghui Li, Beijing (CN); Jia Zhao, Beijing (CN); Qingyi Wang, Beijing (CN); Meiyan Wang, Beijing (CN); Jianbo Sun, Beijing (CN)

(73) Assignee: BEIJING BAYI SPACE LIQUID CRYSTAL TECHNOLOGY CO. LTD., Beijing (CN)

( * ) Notice: Subject to any disclaimer, the term of this patent is extended or adjusted under 35 U.S.C. 154(b) by 0 days.

(21) Appl. No.: 18/308,612

(22) Filed: Apr. 27, 2023

(65) Prior Publication Data

US 2023/0286992 A1   Sep. 14, 2023

Related U.S. Application Data

(63) Continuation of application No. PCT/CN2020/139376, filed on Dec. 25, 2020.

(30) Foreign Application Priority Data

Oct. 30, 2020   (CN) .......................... 202011195763.8

(51) Int. Cl.
*C07D 487/04*   (2006.01)
*H10K 50/11*   (2023.01)
(Continued)

(52) U.S. Cl.
CPC ......... *C07D 487/04* (2013.01); *C07D 519/00* (2013.01); *C09K 11/06* (2013.01);
(Continued)

(58) Field of Classification Search
CPC .............. C07D 491/048; C07D 513/04; C07D 519/00; H10K 85/626; H10K 85/6574;
(Continued)

(56) References Cited

U.S. PATENT DOCUMENTS 9,837,627 B2 * 12/2017 Lee .................... H10K 50/15
9,911,925 B2 *  3/2018 Lee .................... H10K 85/622
(Continued)

OTHER PUBLICATIONS

International Search Report issued in International Patent Application No. PCT/CN2020/139376; dated Aug. 4, 2021; 5 pgs.
(Continued)

*Primary Examiner* — Caleb E Henry
(74) *Attorney, Agent, or Firm* — HAUPTMAN HAM, LLP

(57) ABSTRACT

The present invention relates to an organic compound, an organic electroluminescent material, and an organic electroluminescent element. The structural formula of the compound is shown in formula (I). When the organic compound of the present invention is used for preparing an organic electroluminescent element, the electron mobility, thermal stability, and luminescent characteristics are excellent; and the organic compound can be applied to an organic layer of the organic electroluminescent element. The organic compound of the present invention has a relatively good film-forming property; and when same is applied to an electron transport layer and an electron transport auxiliary layer, an organic electroluminescent element, which has a lower driving voltage, a higher light emission efficiency, and a
(Continued)

Light longer service life than existing electron transport materials, can be manufactured, and thus, a full-color display panel with having improved performance and a prolonged service life can be manufactured.

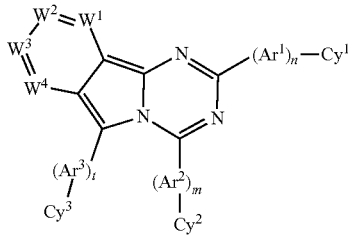

Formula (I)

7 Claims, 1 Drawing Sheet

(51) Int. Cl.
*H10K 85/60* (2023.01)
*C07D 519/00* (2006.01)
*C09K 11/06* (2006.01)

(52) U.S. Cl.
CPC ......... *H10K 50/11* (2023.02); *H10K 85/6572* (2023.02); *C09K 2211/1059* (2013.01)

(58) Field of Classification Search
CPC ............... H10K 85/6576; H10K 50/11; H10K 2101/10; H10K 50/131; H10K 50/852; H10K 85/657; H10K 59/351; H10K 85/342; H10K 2101/20; H10K 2101/90; H10K 85/6572; C09K 11/06
See application file for complete search history.

(56) References Cited

U.S. PATENT DOCUMENTS

| | | | |
|---|---|---|---|
| 10,586,931 B2* | 3/2020 | Kanamoto | H10K 85/342 |
| 11,469,380 B2* | 10/2022 | Kurihara | G09F 9/30 |
| 2016/0351826 A1* | 12/2016 | Kim | H10K 85/615 |
| 2017/0179396 A1* | 6/2017 | Kim | H10K 50/11 |
| 2017/0200903 A1* | 7/2017 | Park | H10K 85/622 |
| 2017/0352447 A1* | 12/2017 | Lee | H01B 1/127 |
| 2018/0053903 A1* | 2/2018 | Suzuki | C07D 491/048 |
| 2019/0248801 A1* | 8/2019 | Sim | C07D 491/048 |
| 2020/0083462 A1* | 3/2020 | Kurihara | H10K 85/657 |
| 2020/0099001 A1* | 3/2020 | Kim | H10K 85/346 |
| 2020/0152887 A1* | 5/2020 | Yamaguchi | H10K 85/6574 |
| 2020/0199135 A1* | 6/2020 | Kurihara | C09K 11/06 |
| 2020/0259099 A1* | 8/2020 | Kurihara | H10K 85/657 |
| 2020/0295280 A1* | 9/2020 | Jeon | H10K 85/346 |
| 2020/0303663 A1* | 9/2020 | Jeon | H10K 85/6572 |

OTHER PUBLICATIONS

Written Opinion of the International Searching Authority issued in International Patent Application No. PCT/CN2020/139376; dated Aug. 4, 2021; 5 pgs.
Notification to Grant Patent Right for Invention issued in Chinese Patent Application No. 202011195763.8; dated Dec. 14, 2022; 3 pgs.
First Office Action issued in Chinese Patent Application No. 202011195763.8; dated May 16, 2022; 8 pgs.
Search Report issued in Chinese Patent Application No. 202011195763.8; dated May 10, 2022; 3 pgs.

* cited by examiner

ORGANIC ELECTROLUMINESCENT ELEMENT HAVING AN ORGANIC COMPOUND

RELATED APPLICATIONS

The present application is Continuation of International Application Number PCT/CN2020/139376 filed Dec. 25, 2020, and claims priority to Chinese Application Number 202011195763.8 filed Oct. 30, 2020, the disclosure of which are hereby incorporated by reference herein in their entireties.

TECHNICAL FIELD

The present invention belongs to the technical field of organic electroluminescent materials and particularly relates to an organic compound, an organic electroluminescent material, and an organic electroluminescent element.

BACKGROUND ART

In general, an organic luminescent phenomenon refers to a phenomenon that a light is emitted when an electric energy is applied to an organic substance. That is, when an organic layer is disposed between an anode and a cathode, if a voltage is applied between the two electrodes, holes are injected from the anode into the organic layer, and electrons are injected from the cathode into the organic layer. When meeting the injected hole and electron form an exciton. When the exciton transits to a ground state, light and heat are emitted.

As a method for efficiently manufacturing an organic electroluminescent element, studies have been made to manufacture an organic layer in an element by replacing a single layer with a multilayer structure. Tang in 1987 proposed an organic electroluminescent element having a stacked structure of a hole layer and a functional layer of an emission layer. Most organic electroluminescent elements currently used comprise: a substrate, an anode, a hole injection layer for receiving holes from the anode, a hole transport layer for transporting holes, an emission layer for emitting a light by recombination of holes and electrons, an electron transport layer for transporting electrons, an electron injection layer for receiving electrons from a cathode, and a cathode. The reason why the organic electroluminescent element is formed in a multilayer manner is that the moving speeds of the holes and the electrons are different, if the hole injection layer and the hole transport layer, and the electron transport layer and the electron injection layer are appropriately manufactured, the holes and the electrons may be efficiently transported, a balance between the holes and the electrons in the element may be achieved, and the utilization rate of the excitons may be improved.

In addition, many organic monomolecular substances having a imidazolyl, a -zolyl, a thiazolyl, or a spiroflurenyl have been reported as substances that may be conventionally used in the electron injection layer and the electron transport layer. For example, TPBI disclosed in the Chinese Patents CN 103833507 B, CN 107573328 B, and CN 107556310 B and the U.S. Pat. No. 5,645,948 to the Kodak Company in 1996 is a imidazolyl-containing substance for an electron transport layer, with three N-phenylbenzimidazolyls contained in 1-, 3-, and 5-substitution positions of benzene in the structure. Functionally, the TPBI has an electron transport ability and also has a function of blocking holes crossing over from an emission layer, but has a problem of a low thermal stability when actually used in an element.

In view of the above concerns, the present invention is proposed.

SUMMARY OF THE INVENTION

In order to solve the above problems in the prior art, the present invention provides an organic compound, an organic electroluminescent material, and an organic electroluminescent element. The organic compound of the present invention as a luminescent material may improve the stability, luminous efficiency, service life, etc., of a luminescent element.

A first object of the present invention provides an organic compound. The organic compound has a structural formula shown in a formula (I):

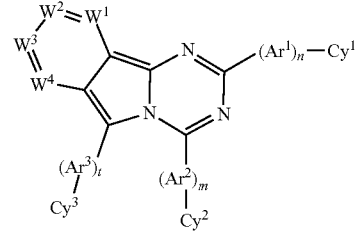

Formula (I)

wherein $W^1$-$W^4$ are the same or different from each other and are each independently selected from $CR^1$ or N;
the $R^1$ is selected from one of hydrogen, deuterium, halogen, cyano, nitro, $C_1$-$C_{40}$ alkyl, $C_2$-$C_{40}$ alkenyl, $C_2$-$C_{40}$ alkynyl, $C_3$-$C_{40}$ cycloalkyl, heterocycloalkyl having an atomic nucleus number of 3 to 40, $C_6$-$C_{60}$ aryl, $C_2$-$C_{60}$ heteroaryl, $C_1$-$C_{40}$ alkoxy, $C_6$-$C_{60}$ aryloxy, $C_1$-$C_{40}$ alkylsilyl, $C_6$-$C_{60}$ arylsilyl, $C_1$-$C_{40}$ alkylboryl, $C_6$-$C_{60}$ arylboryl, $C_6$-$C_{60}$ arylphosphoryl, $C_6$-$C_{60}$ aryloxyphosphinyl, and $C_6$-$C_{60}$ arylamino, when there are a plurality of the substituents $R^1$, any two or more adjacent substituents may be optionally jointed or fused, or bonded to a bridging group of a same nitrogen atom, phosphorus atom, boron atom, oxygen or sulfur to be bridged with each other, to form a single ring or a fused ring;
$Ar^1$, $Ar^2$, and $Ar^3$ are a single bond, $C_6$-$C_{60}$ arylene or $C_2$-$C_{60}$ heteroarylene;
$Cy^1$, $Cy^2$, and $Cy^3$ are each independently selected from $C_6$-$C_{60}$ aryl or $C_2$-$C_{60}$ heteroaryl;
m, n, and t represent an integer of 0-5; and
the arylene and the heteroarylene in the $Ar^1$, the $Ar^2$, and the $Ar^3$, the aryl and the heteroaryl in the $Cy^1$, the $Cy^2$, and the $Cy^3$, and the alkyl, the alkenyl, the alkynyl, the cycloalkyl, the heterocycloalkyl, the aryl, the heteroaryl, the alkoxy, the aryloxy, the alkylsilyl, the arylsilyl, the alkylboryl, the arylboryl, the arylphosphoryl, the aryloxyphosphinyl, and the arylamino in the $R^1$ are each independently selected from one of deuterium, a halogen atom, cyano, nitro, $C_1$-$C_{40}$ alkyl, $C_2$-$C_{40}$ alkenyl, $C_2$-$C_{40}$ alkynyl, $C_3$-$C_{40}$ cycloalkyl, $C_3$-$C_{40}$ heterocycloalkyl, $C_6$-$C_{60}$ aryl, $C_2$-$C_{60}$ heteroaryl, $C_1$-$C_{40}$ alkoxy, $C_6$-$C_{60}$ aryloxy, $C_1$-$C_{40}$ alkylsilyl, $C_6$-$C_{60}$ arylsilyl, $C_1$-$C_{40}$ alkylboryl, $C_6$-$C_{60}$ arylboryl, $C_6$-$C_{60}$ arylphosphoryl, $C_6$-$C_{60}$ aryloxyphosphinyl, and $C_6$-$C_{60}$ arylamino, and in such a case, when there are a plurality of substituents, the substituents may be the same or different from each other.

Further, the $C_2$-$C_{60}$ heteroaryl is one of the following structures:

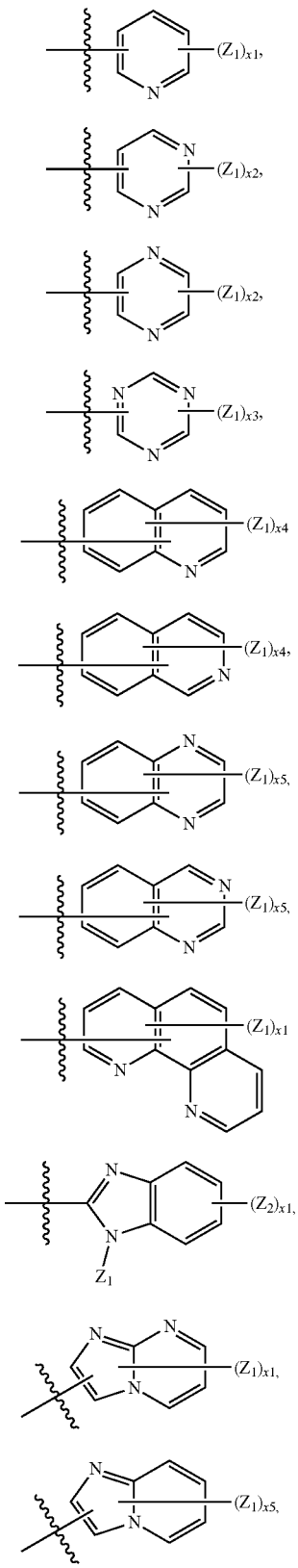

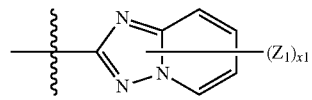

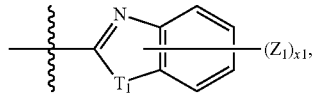

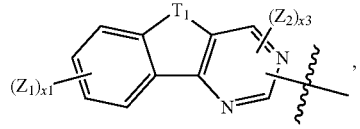

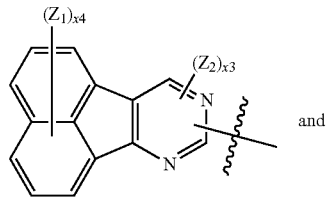

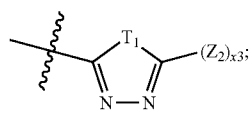

$Z_1$ and $Z_2$ are each independently selected from one of hydrogen, deuterium, a halogen atom, hydroxy, a nitrile group, nitro, amino, amidino, hydrazino, hydrazono, carboxy or a carboxylate thereof, sulfo or a sulfonate thereof, phosphoryl or a phosphate thereof, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{40}$ cycloalkyl, $C_3$-$C_{40}$ cycloalkenyl, $C_6$-$C_{60}$ aryl, $C_6$-$C_{60}$ aryloxy, $C_6$-$C_{60}$ arylboryl, $C_6$-$C_{60}$ arylphosphoryl, $C_6$-$C_{60}$ aryloxyphosphinyl, $C_6$-$C_{60}$ arylamino or $C_2$-$C_{60}$ heteroaryl;

x1 represents an integer of 1-4; x2 represents an integer of 1-3; x3 represents 1 or 2; x4 represents an integer of 1-6; x5 represents an integer of 1-5;

$T_1$ represents oxygen, sulphur, $CR^2R^3$ or $NCy^1$;

the $R^2$ and the $R^3$ are each independently selected from one of hydrogen, deuterium, $C_1$-$C_{40}$ alkyl, $C_2$-$C_{40}$ of alkenyl, $C_2$-$C_{40}$ of alkynyl, $C_3$-$C_{40}$ of cycloalkyl, heterocycloalkyl having an atomic nucleus number of 3 to 40, $C_6$-$C_{60}$ aryl, and $C_2$-$C_{60}$ heteroaryl; and ∿∿ represents a connection bond of a substituent to a main structure.

Further, the $Ar^1$, the $Ar^2$, and the $Ar^3$ is one of the following structures:

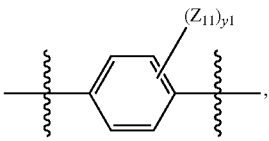

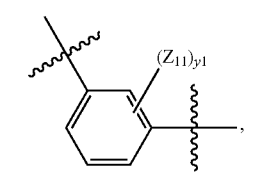

-continued

III-3
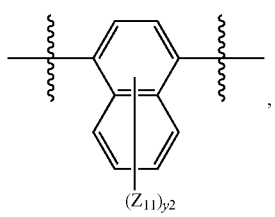

III-4
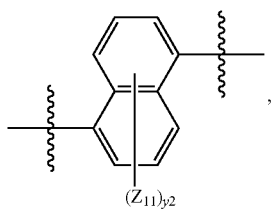

III-5
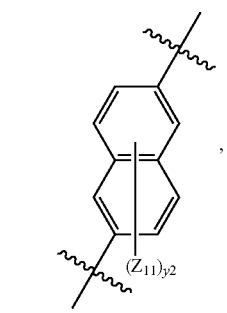

III-6
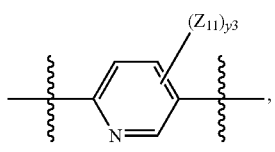

III-7
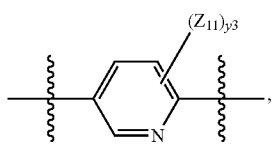

III-8
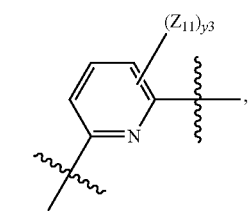

III-9
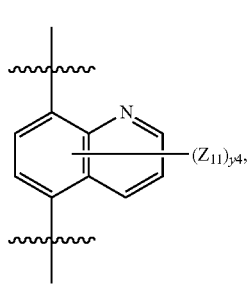

-continued

III-10
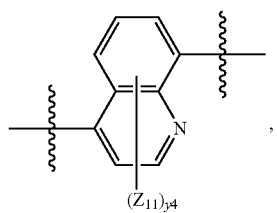

III-11

III-12

III-13

III-14

III-15

$Z_{11}$ and $Z_{12}$ are each independently selected from one of hydrogen, deuterium, a halogen atom, hydroxy, a nitrile group, nitro, amino, amidino, hydrazino, hydrazono, carboxy or a carboxylate thereof, sulfo or a sulfonate thereof, phosphoryl or a phosphate thereof, $C_1$-$C_{40}$ alkyl, $C_2$-$C_{40}$ alkenyl, $C_2$-$C_{40}$ alkynyl, $C_1$-$C_{40}$ alkoxy, $C_3$-$C_{40}$ cycloalkyl, $C_3$-$C_{40}$ cycloalkenyl, $C_6$-$C_{60}$ aryl, $C_6$-$C_{60}$ aryloxy, $C_6$-$C_{60}$ arylboryl, $C_6$-$C_{60}$ arylphosphoryl, $C_6$-$C_{60}$ aryloxyphosphinyl, $C_6$-$C_{60}$ arylamino or $C_2$-$C_{60}$ heteroaryl;

y1 represents an integer of 1-4; y2 represents an integer of 1-6; y3 represents an integer of 1-3; y4 represents an integer of 1-5;

$T_2$ represents oxygen, sulphur, $CR^2R^3$ or $NCy^1$;

the $R^2$ and the $R^3$ are each independently selected from one of hydrogen, deuterium, $C_1$-$C_{40}$ alkyl, $C_2$-$C_{40}$ of alkenyl, $C_2$-$C_{40}$ of alkynyl, $C_3$-$C_{40}$ of cycloalkyl, heterocycloalkyl having an atomic nucleus number of 3 to 40, $C_6$-$C_{60}$ aryl, and $C_2$-$C_{60}$ heteroaryl; and ∿∿∿ represents a connection bond of a substituent to a main structure.

Further, the $W^1$-$W^4$ are the same or different from each other and are each independently selected from $CR^1$ or N, and the $R^1$ is selected from one of hydrogen, deuterium, $C_1$-$C_{40}$ alkyl, $C_6$-$C_{60}$ aryl, and $C_2$-$C_{60}$ heteroaryl.

Further, the $Cy^1$, the $Cy^2$, and the $Cy^3$ are selected from one of pyrimidine, pyrazine, triazine, imidazole, benzimidazole, phenanthroimidazole, imidazopyridine, triazolopyridine, and quinazoline;

the pyrimidine, the pyrazine, the triazine, the imidazole, the benzimidazole, the phenanthroimidazole, the imidazopyridine, the triazolopyridine, and the quinazoline may be each independently substituted with one of deuterium, a halogen atom, cyano, nitro, $C_1$-$C_{40}$ alkyl, $C_2$-$C_{40}$ alkenyl, $C_2$-$C_{40}$ alkynyl, $C_3$-$C_{40}$ cycloalkyl, $C_3$-$C_{40}$ heterocycloalkyl, $C_6$-$C_{60}$ aryl, $C_2$-$C_{60}$ heteroaryl, $C_1$-$C_{40}$ alkoxy, $C_6$-$C_{60}$ aryloxy, $C_1$-$C_{40}$ alkylsilyl, $C_6$-$C_{60}$ arylsilyl, $C_1$-$C_{40}$ alkylboryl, $C_6$-$C_{60}$ arylboryl, $C_6$-$C_{60}$ arylphosphoryl, $C_6$-$C_{60}$ aryloxyphosphinyl, and $C_6$-$C_{60}$ arylamino, in such a case, when there are a plurality of substituents, the substituents may be the same or different from each other.

The organic compound described according to the present invention has a significantly increased molecular weight, by introducing different substituents $R^1$, $Cy^1$ to $Cy^3$, particularly aryl and/or heteroaryl, thus enables the increase of the glass transition temperature, and can have higher thermal stability compared with a conventional luminescent material. Therefore, the performances and the service life of the organic electroluminescent element comprising the compound of the present invention may be greatly improved. The organic electroluminescent element with such improved performances and service life may eventually maximize the performance of a full-color organic luminescent panel.

Further, the organic compound is one of CJUIP01-CJUIP252 and has a specific structural formula shown as follows:

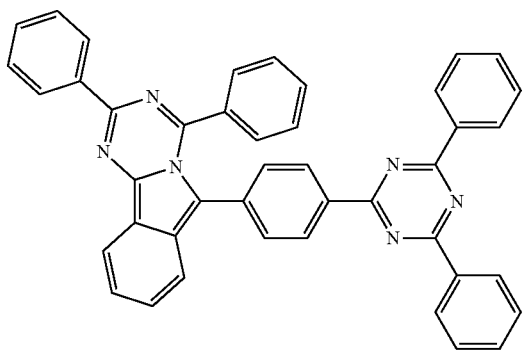

CJHP01

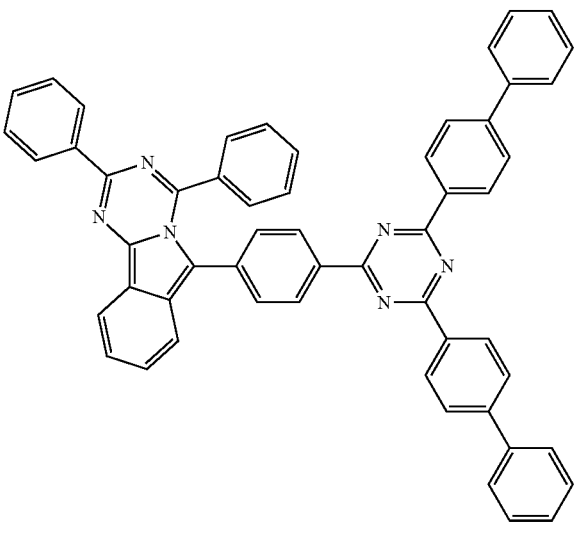

CJHP02

CJHP03

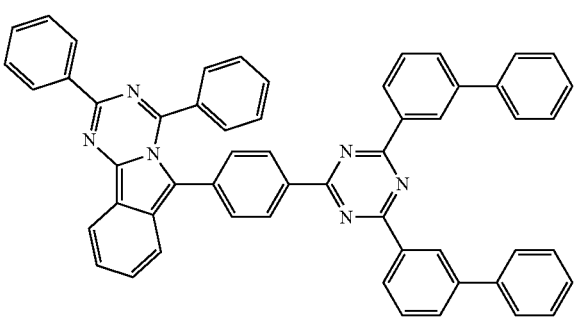

CJHP04

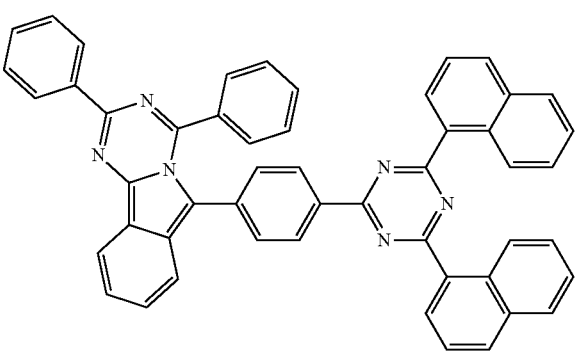

CJHP05

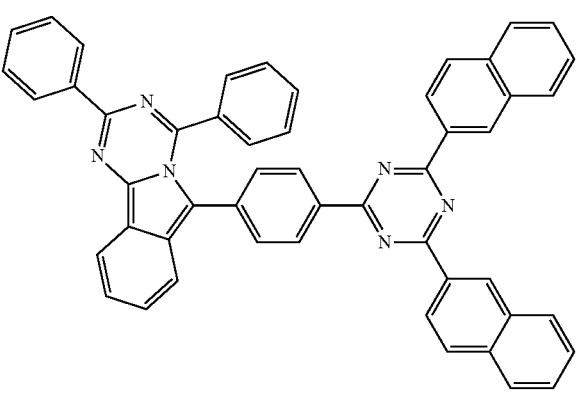

CJHP06
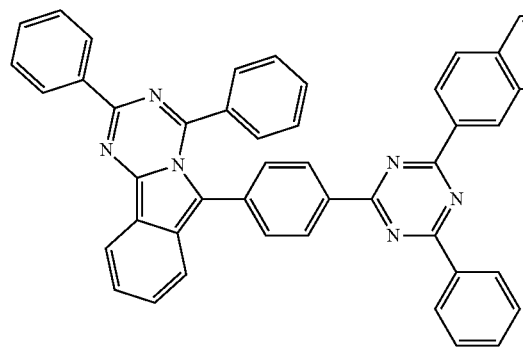
CJHP07
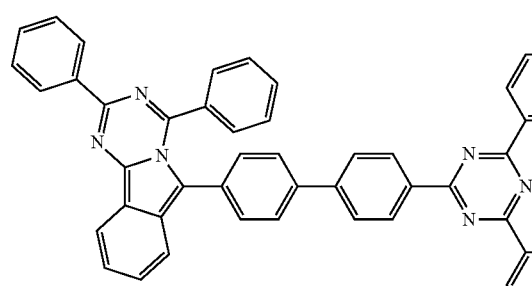
CJHP08
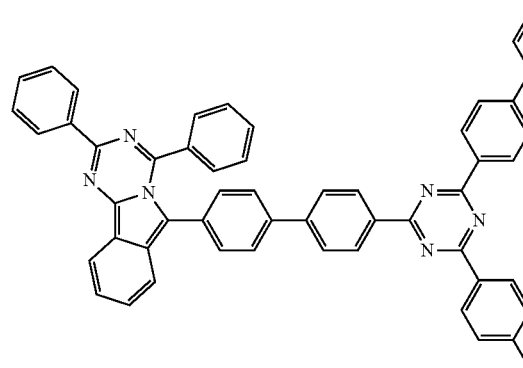
CJHP09
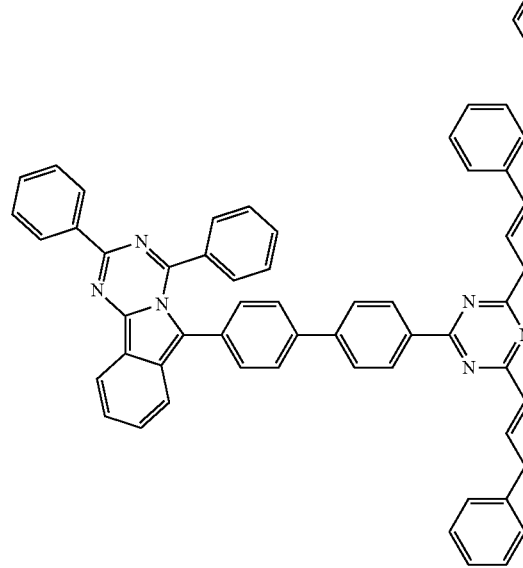
CJHP10
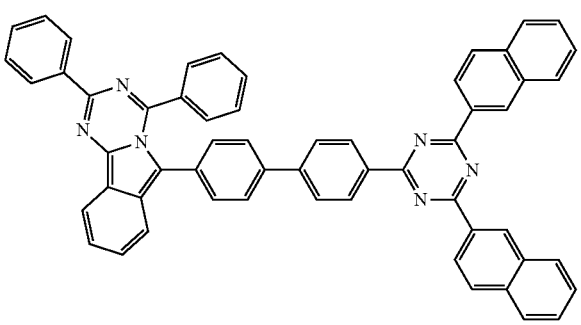
CJHP11
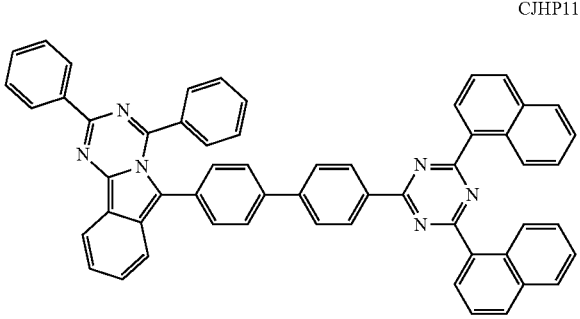
CJHP12
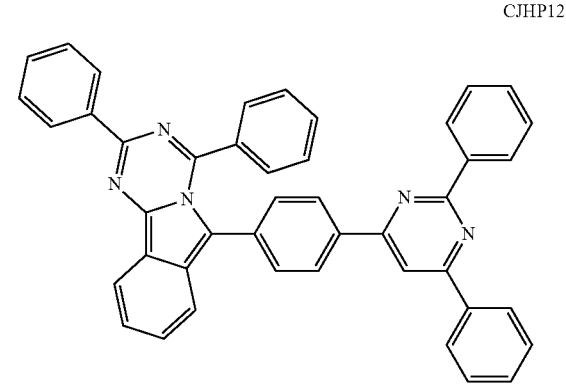
CJHP13
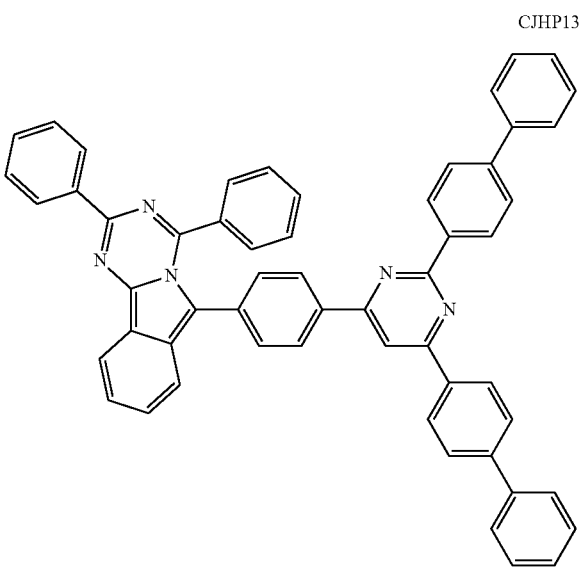

CJHP14
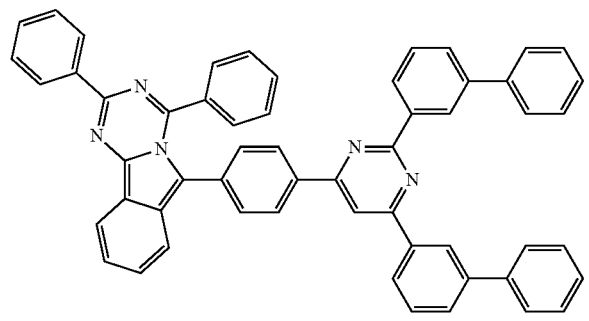
CJHP15
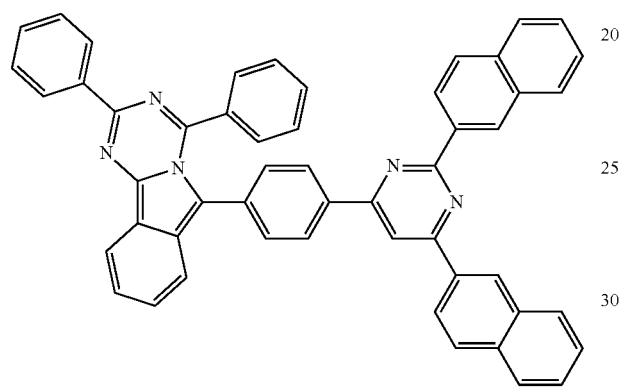
CJHP16
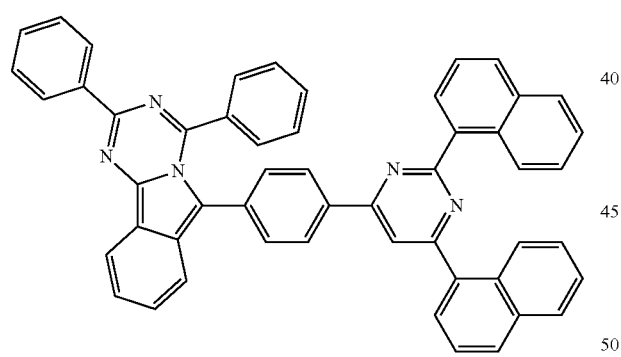
CJHP17
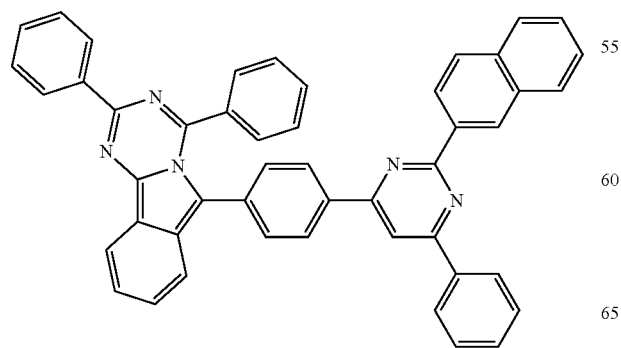
CJHP18
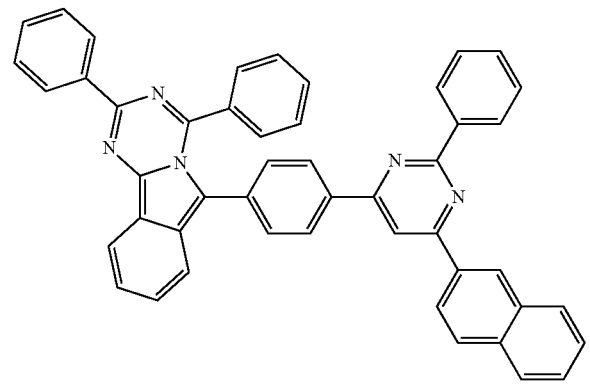
CJHP19
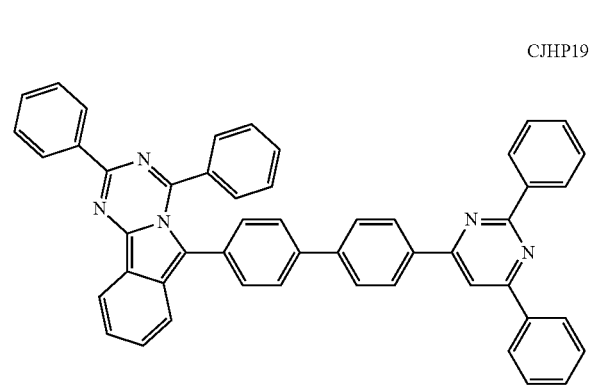
CJHP20
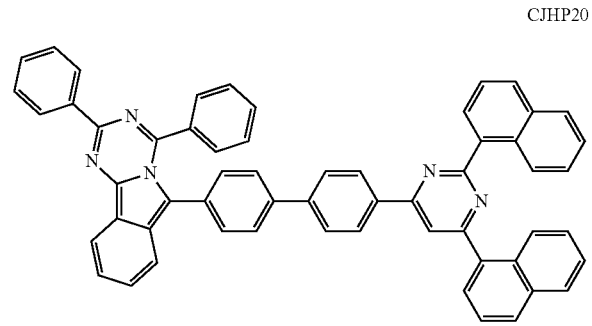
CJHP21
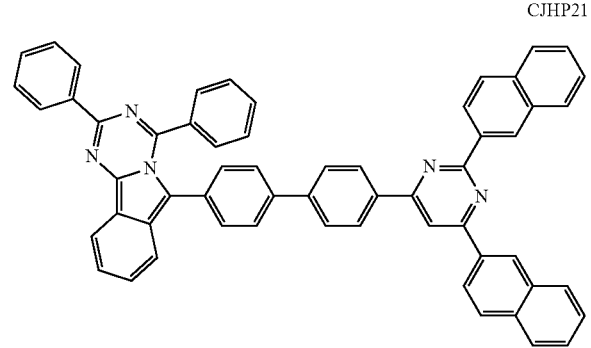

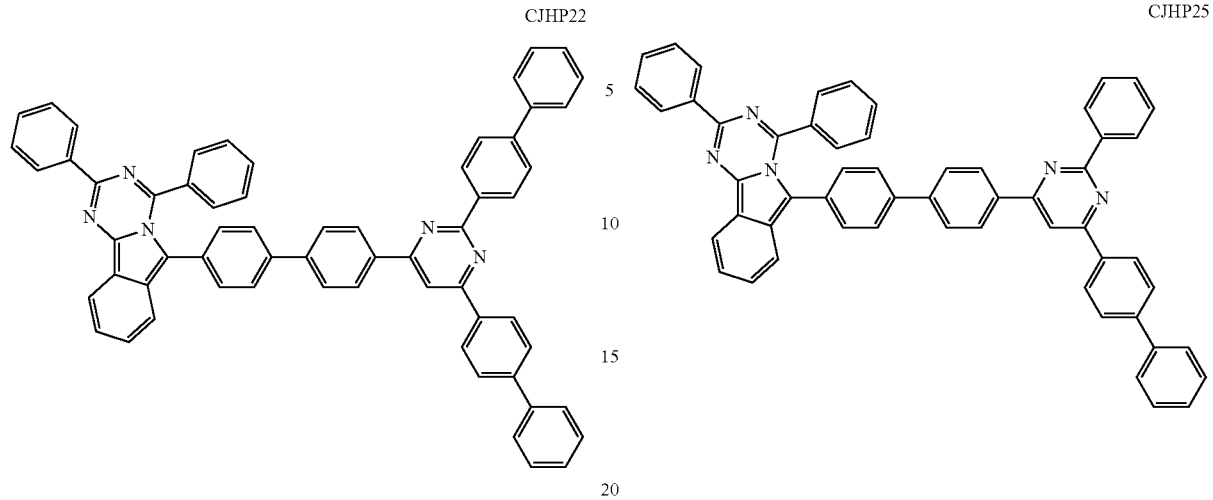
CJHP22
CJHP25
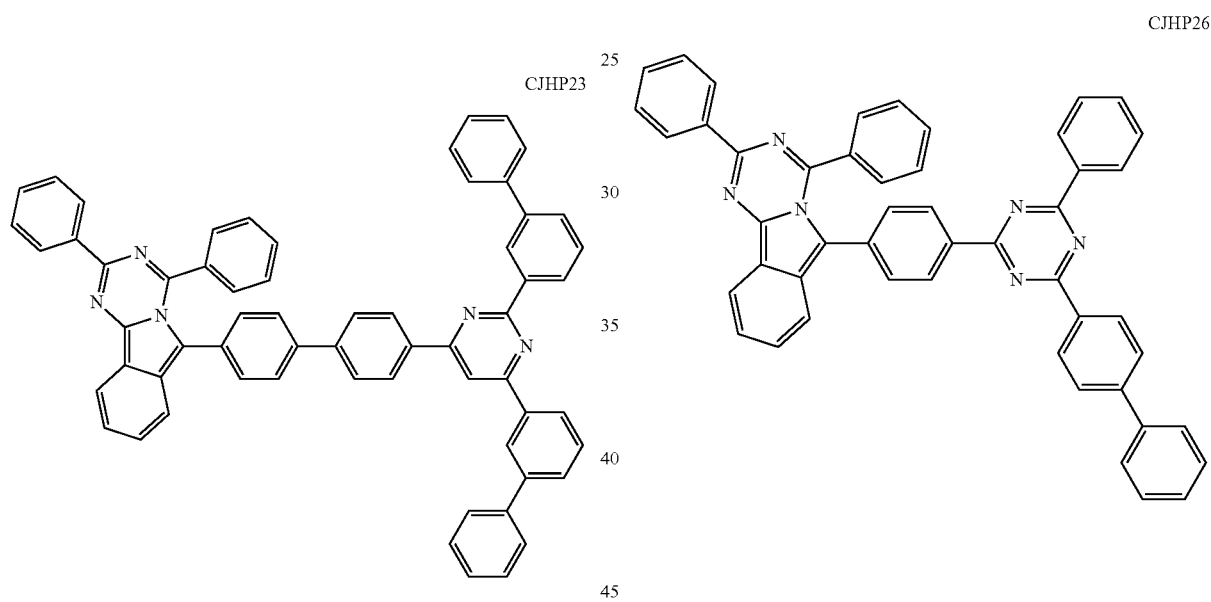
CJHP23
CJHP26
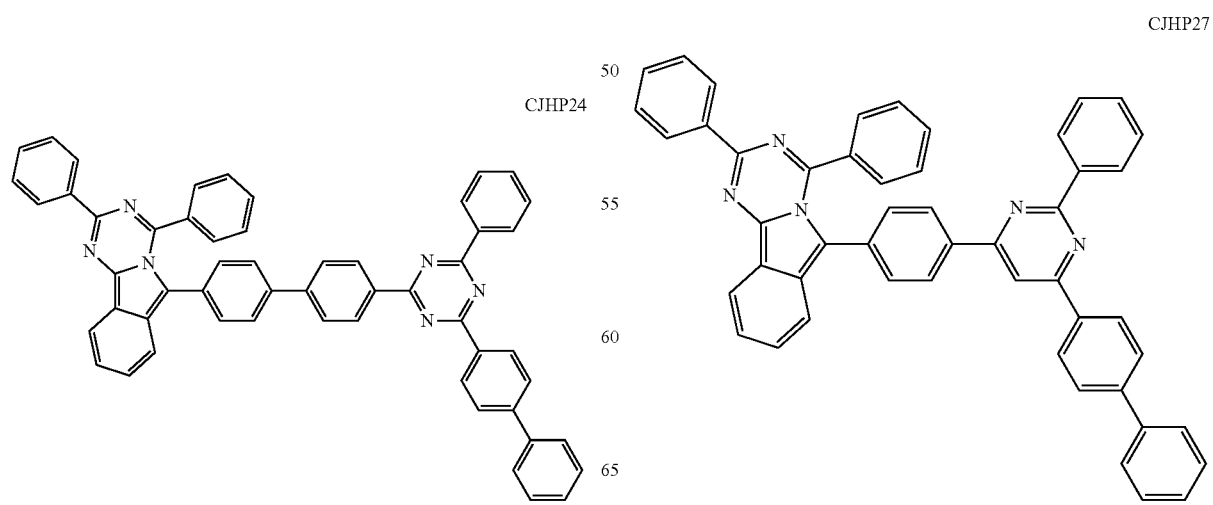
CJHP24
CJHP27

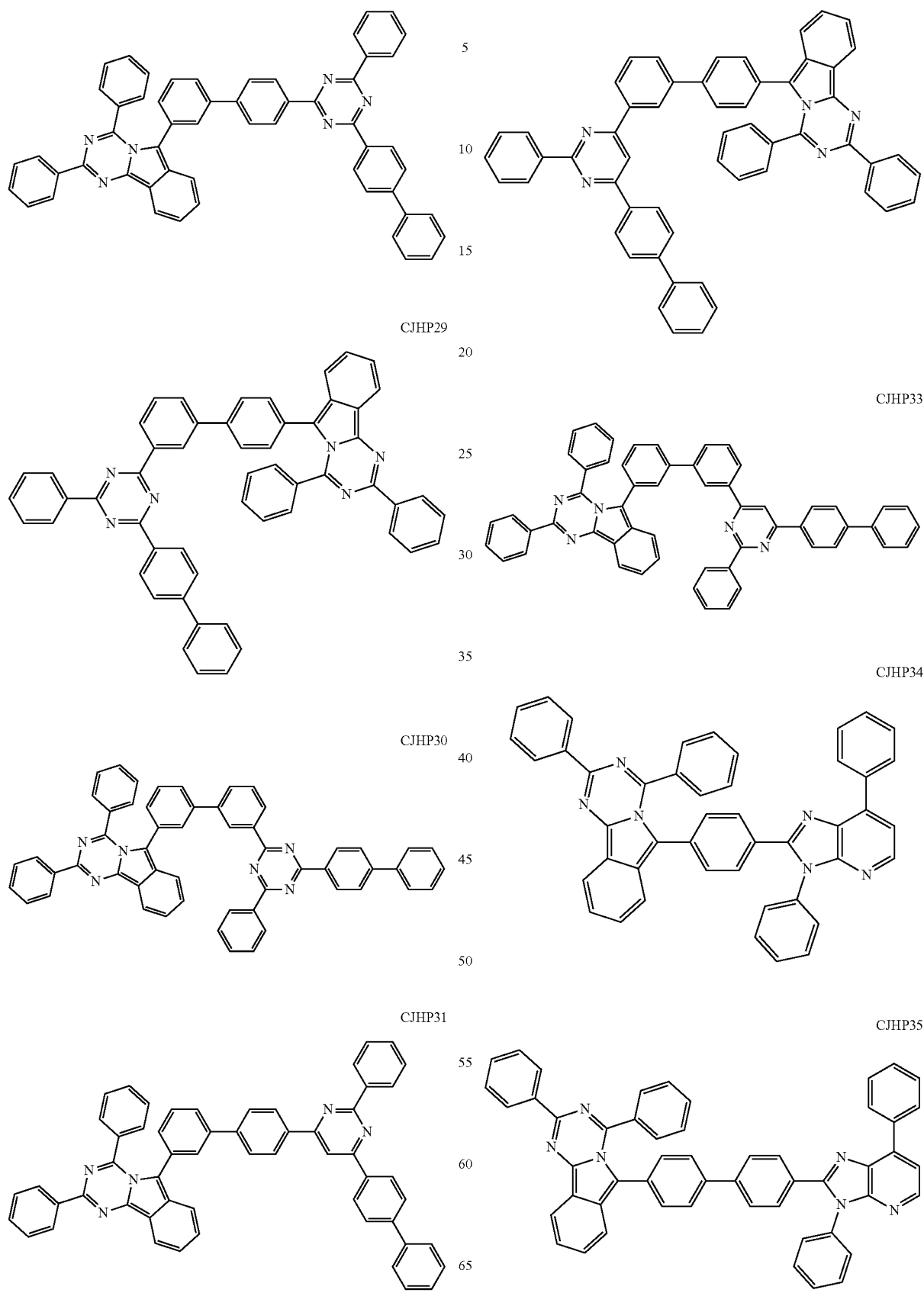

CJHP36
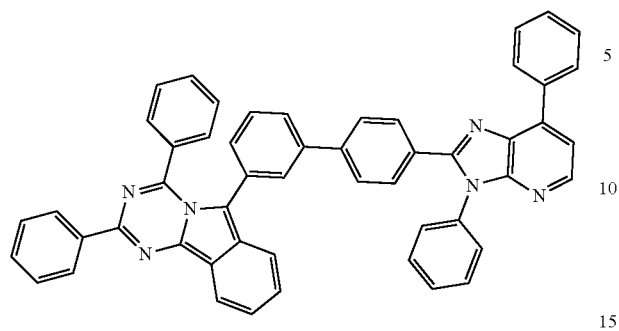
CJHP40
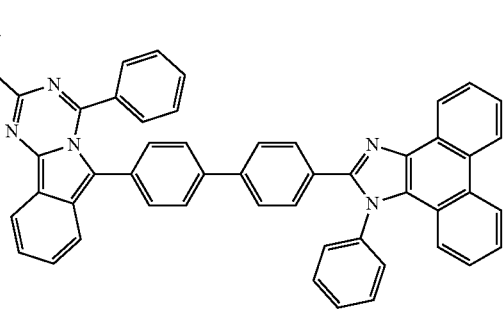
CJHP37
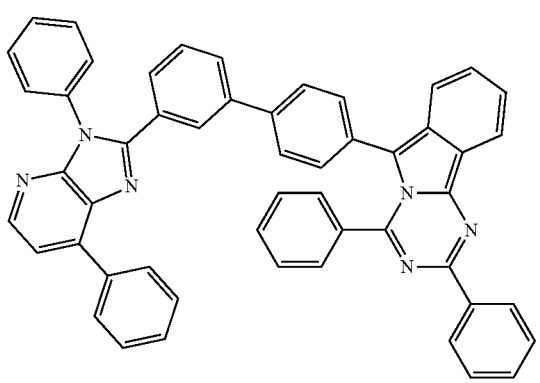
CJHP41
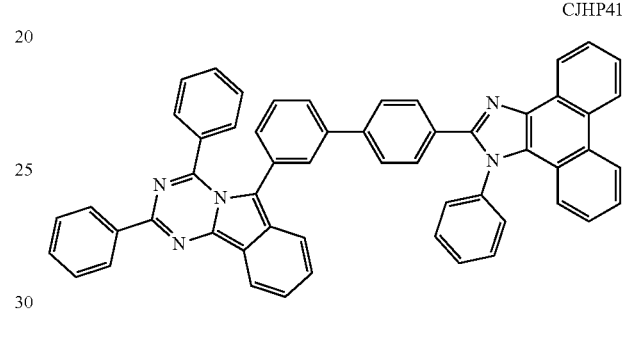
CJHP38
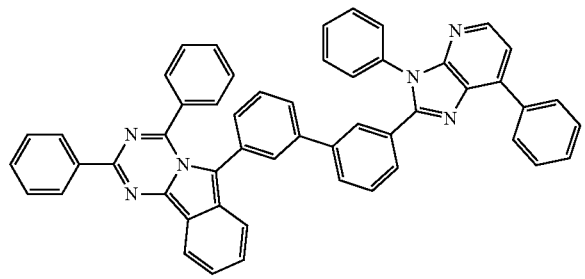
CJHP42
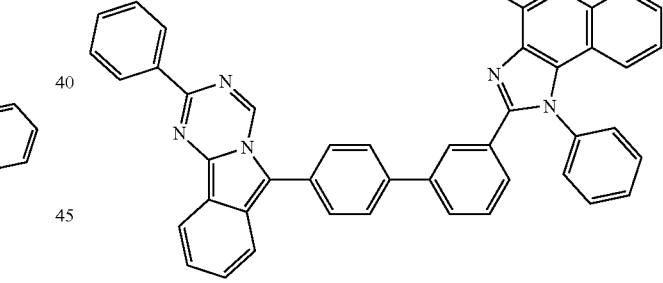
CJHP39
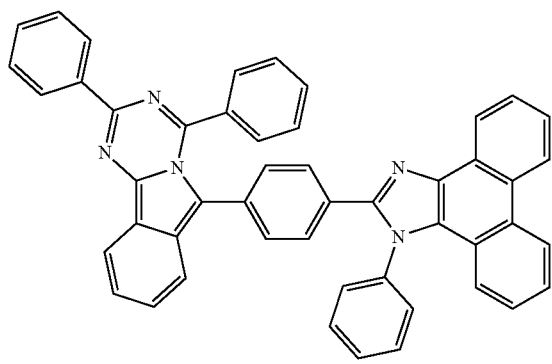
CJHP43
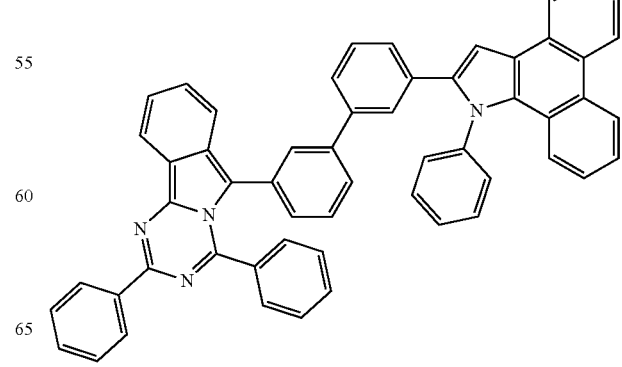

-continued
CJHP44
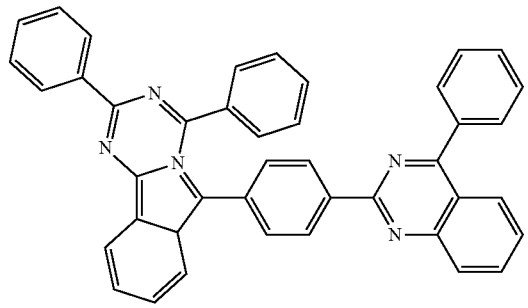
CJHP45
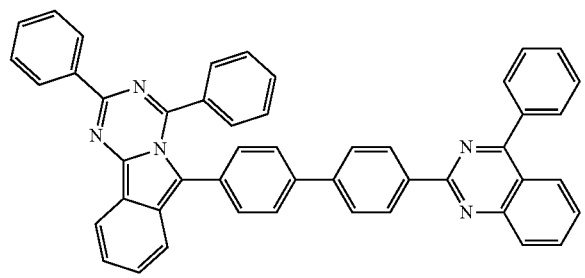
CJHP46
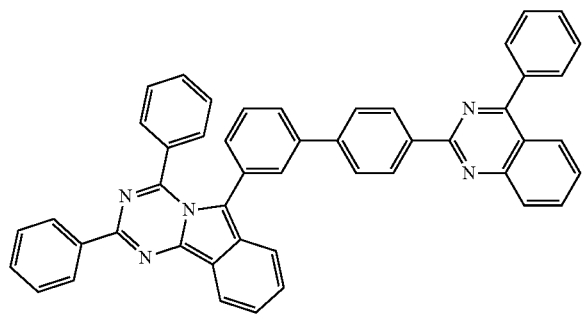
CJHP47
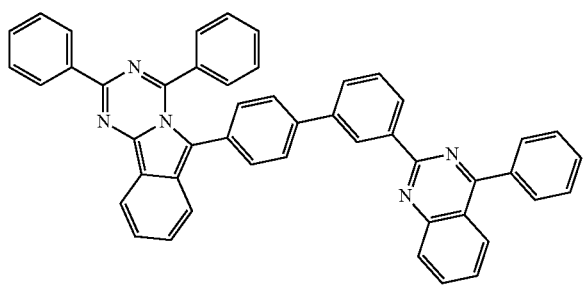
CJHP48
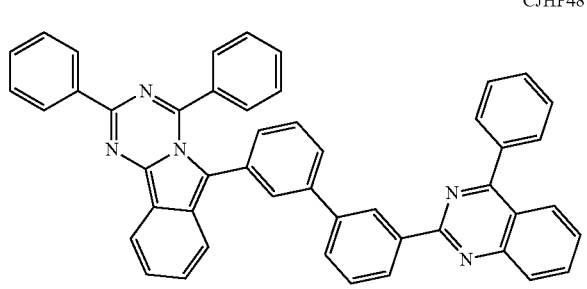
-continued
CJHP49
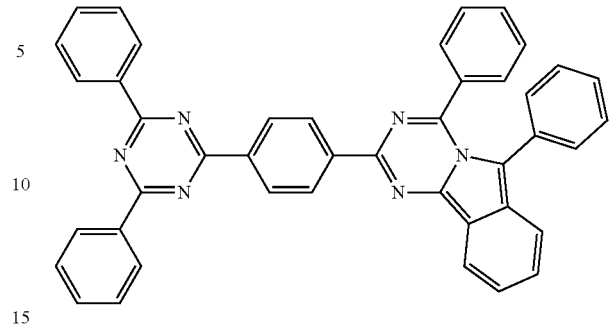
CJHP50
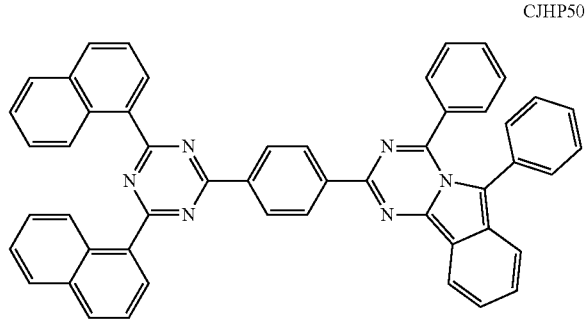
CJHP51
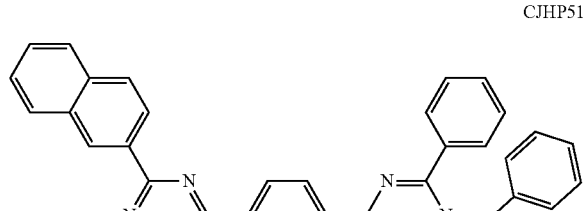
CJHP52
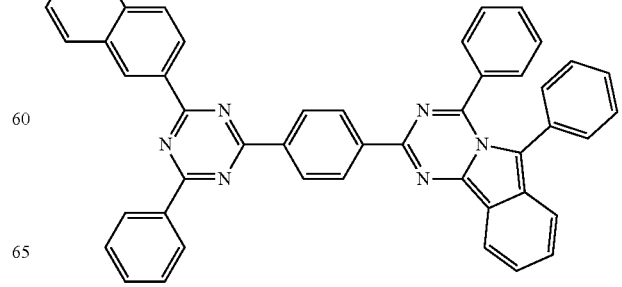

CJHP53
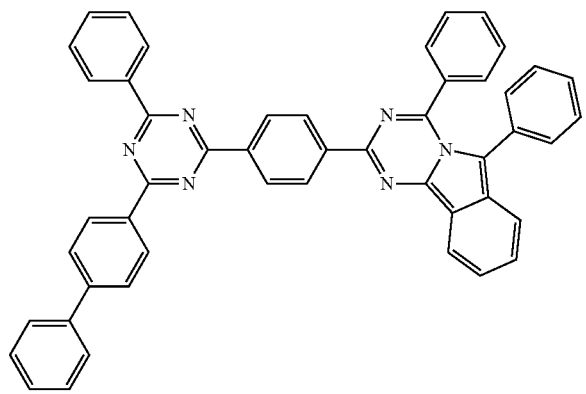
CJHP54
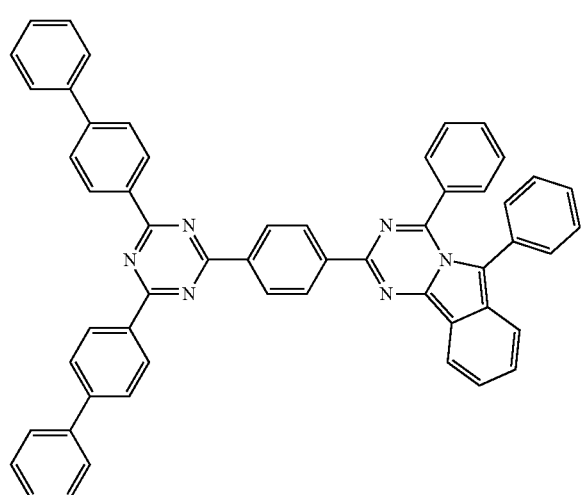
CJHP55
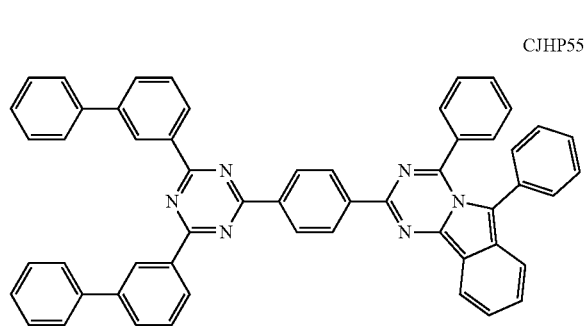
CJHP56
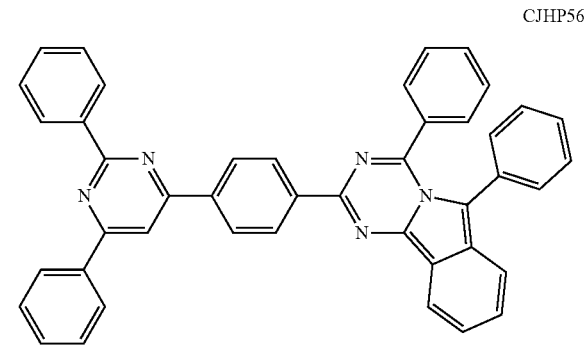
CJHP57
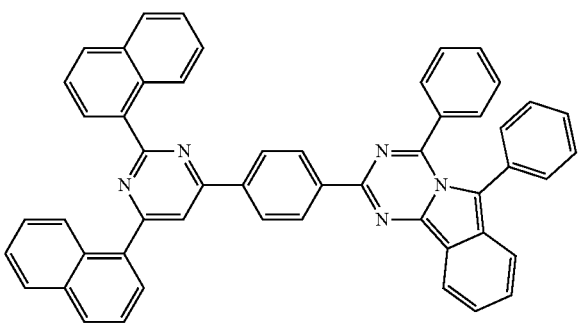
CJHP58
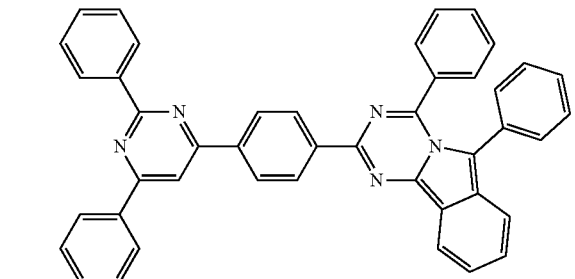
CJHP59
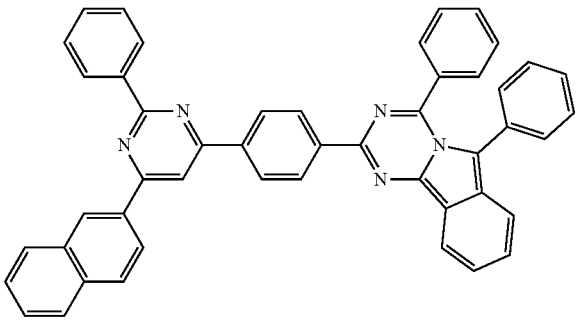
CJHP60

CJHP61
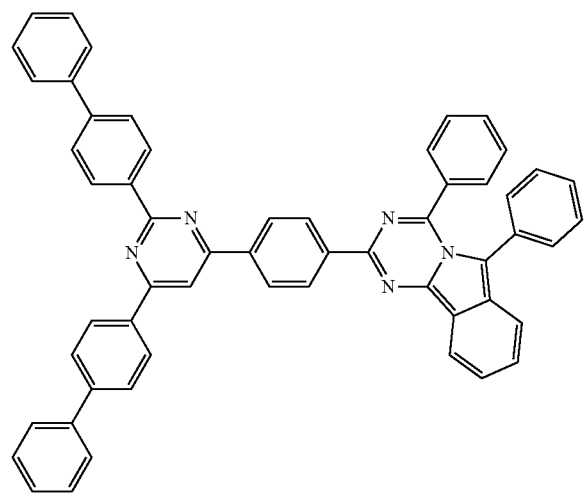
CJHP62
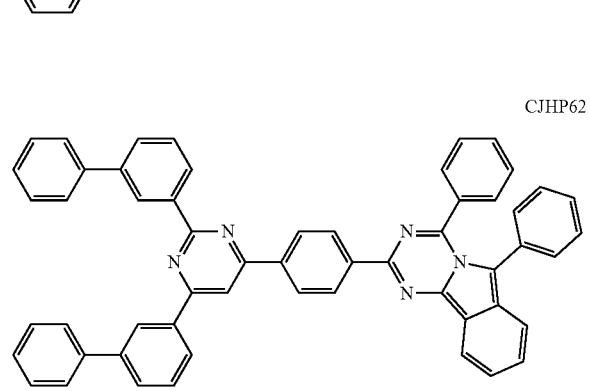
CJHP63
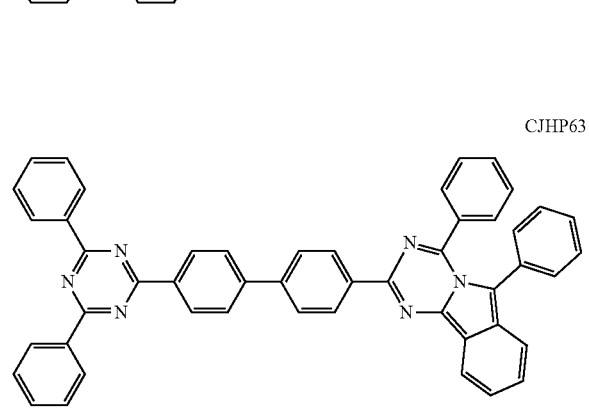
CJHP64
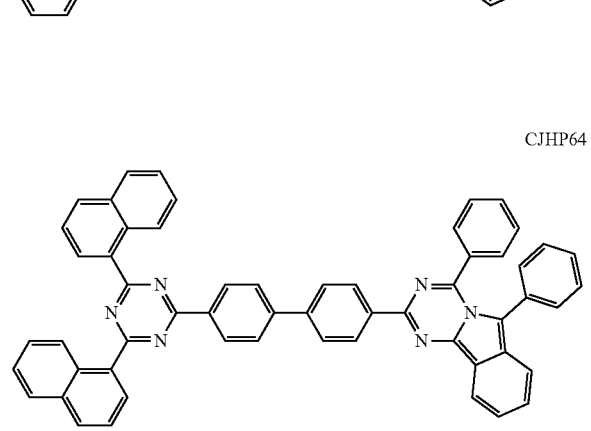
CJHP65
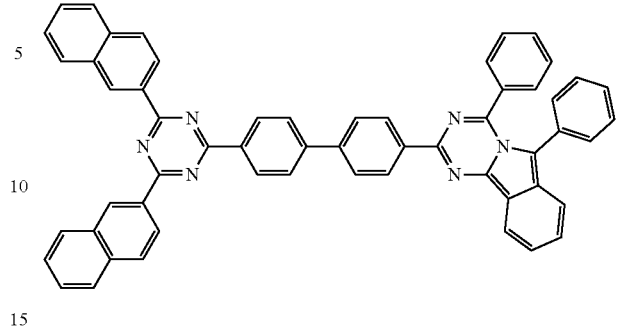
CJHP66
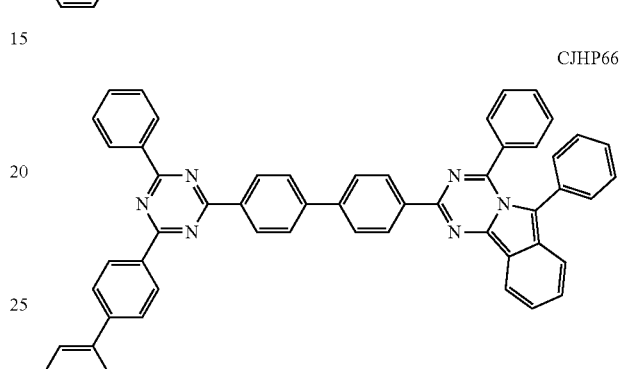
CJHP67
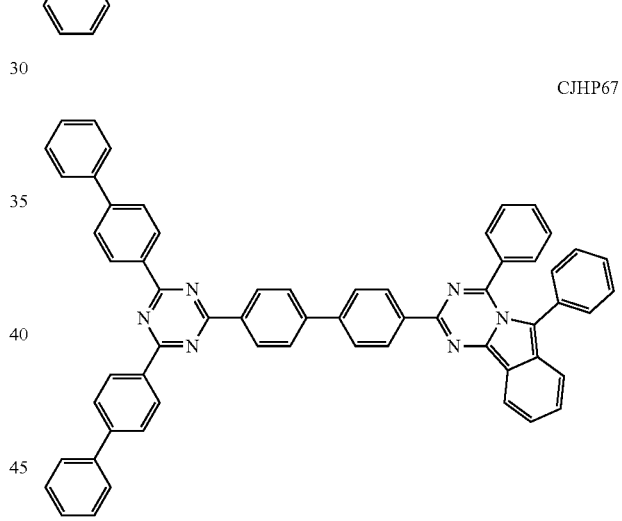
CJHP68
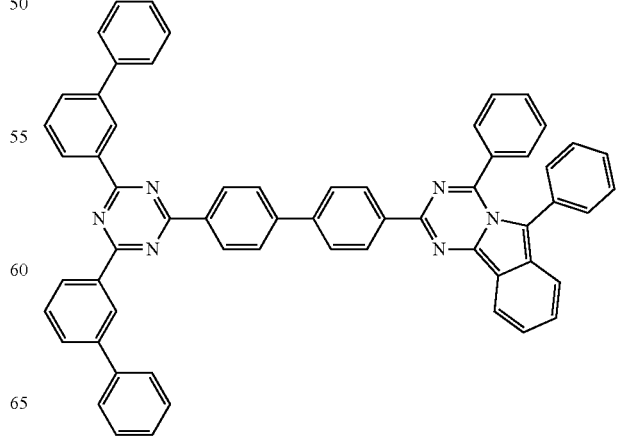

25
-continued
CJHP69
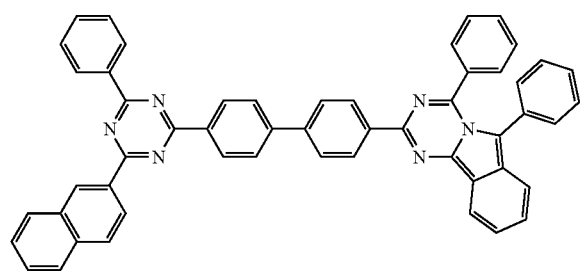
CJHP70
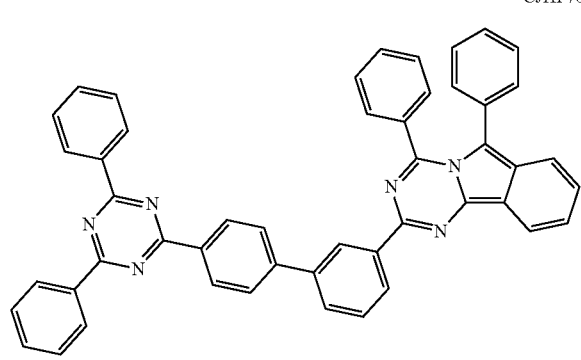
CJHP71
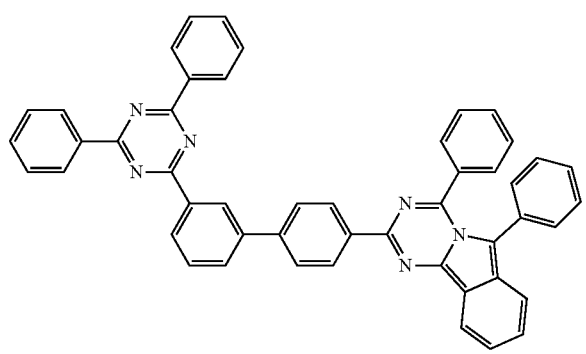
CJHP72
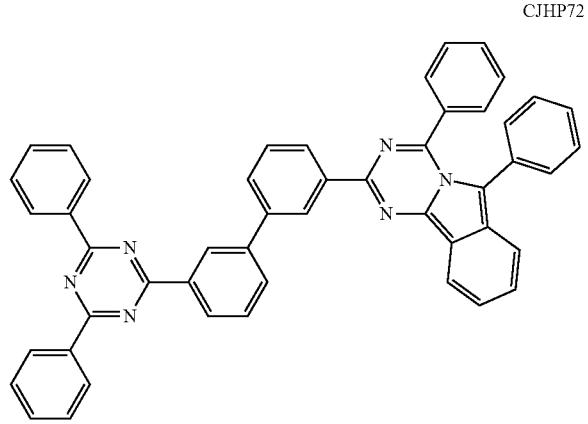
26
-continued
CJHP73
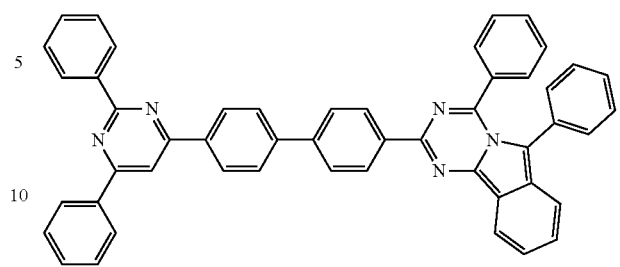
CJHP74
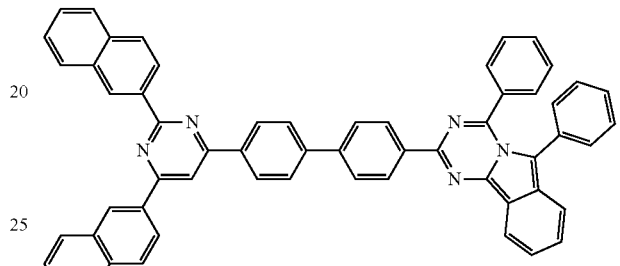
CJHP75
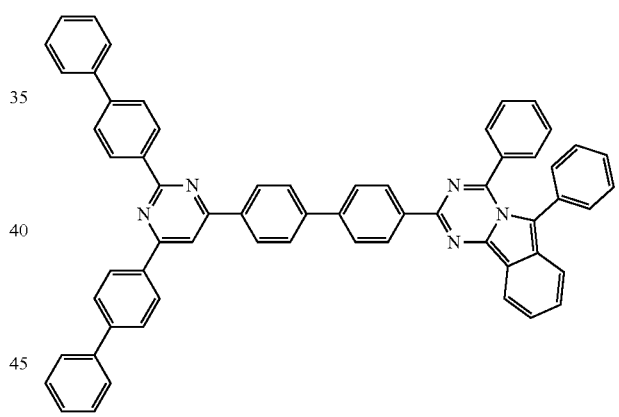
CJHP76
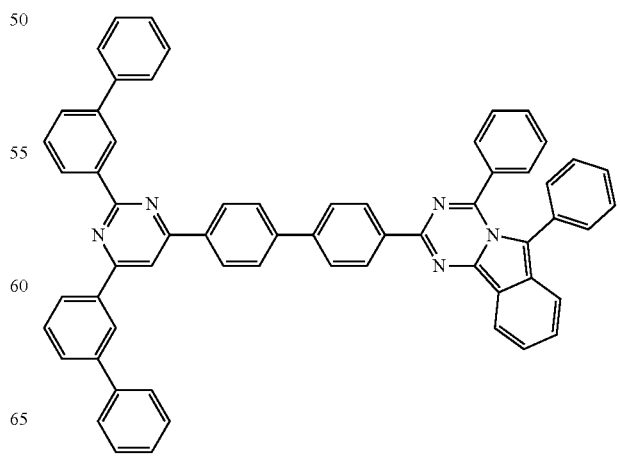

CJHP77
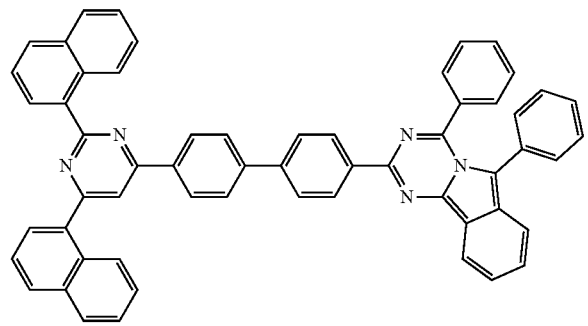
CJHP81
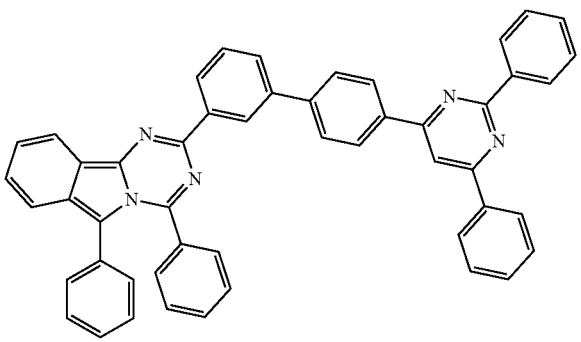
CJHP78
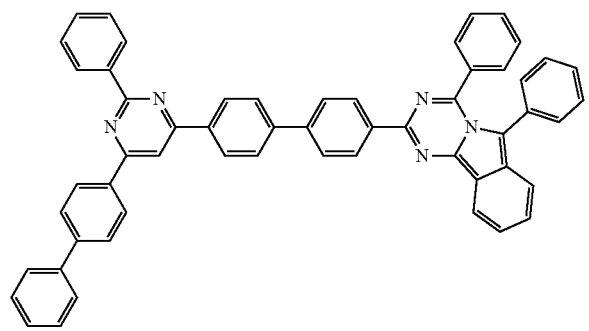
CJHP82
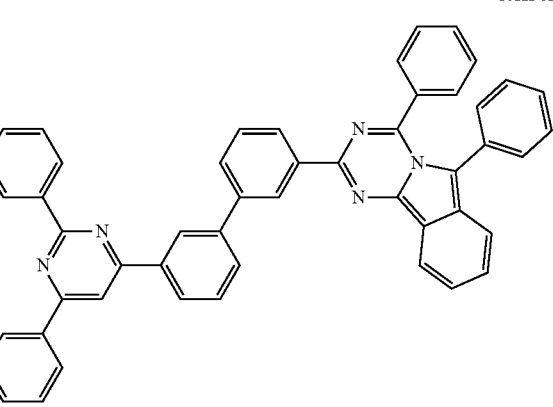
CJHP79
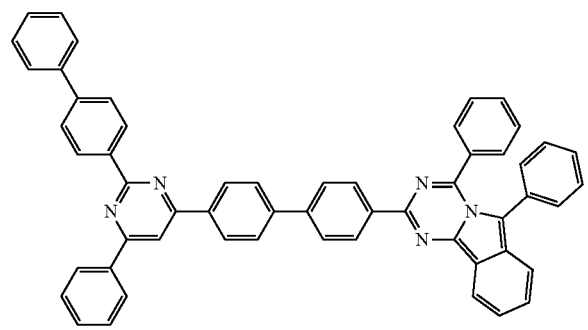
CJHP83
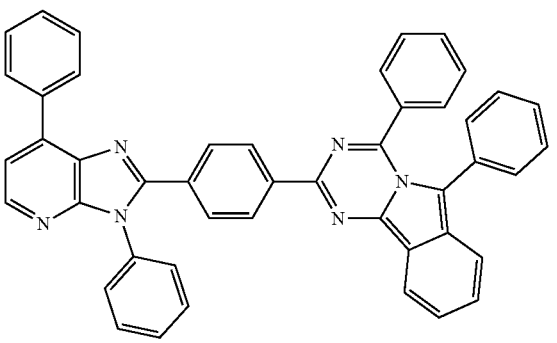
CJHP80
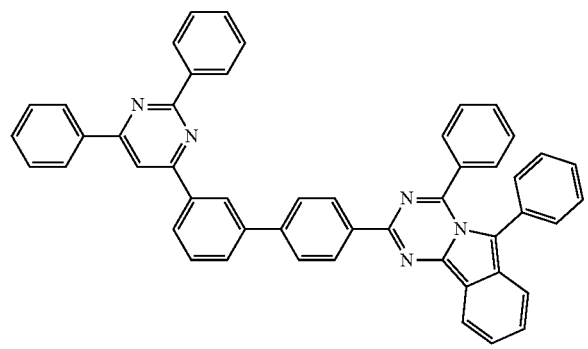
CJHP84
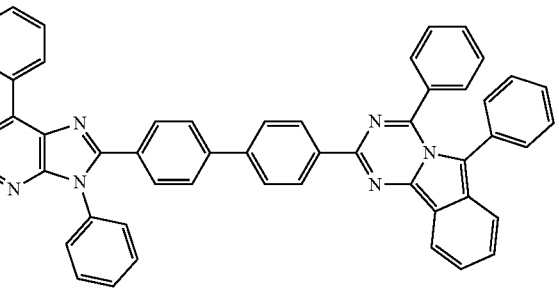

CJHP85
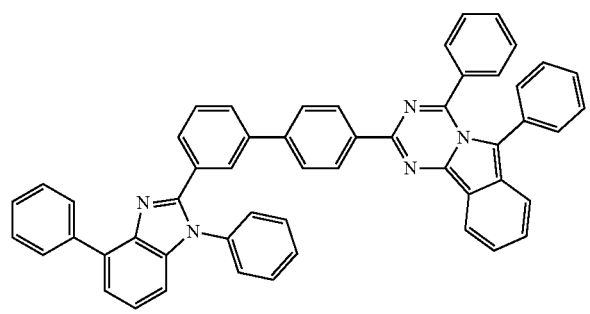
CJHP89
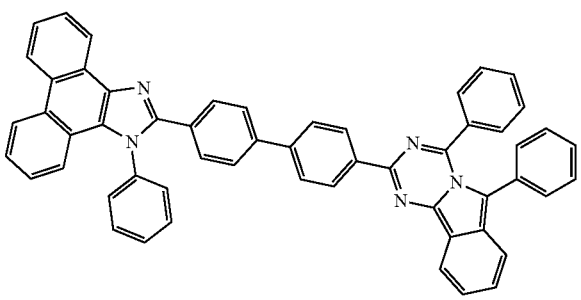
CJHP86
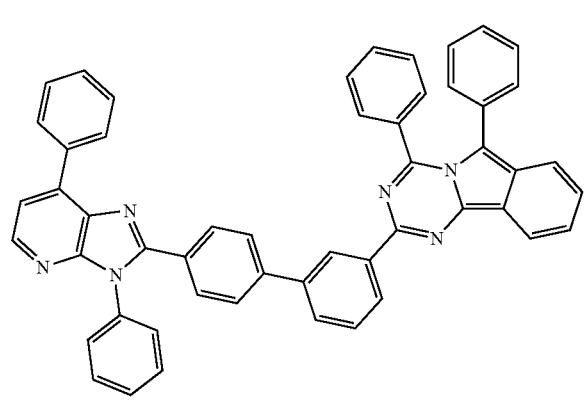
CJHP90
CJHP87
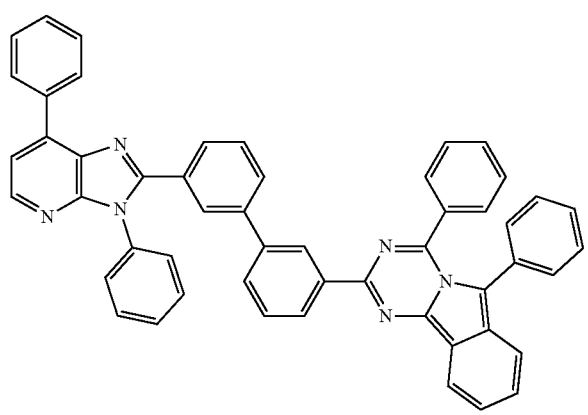
CJHP91
CJHP92
CJHP88
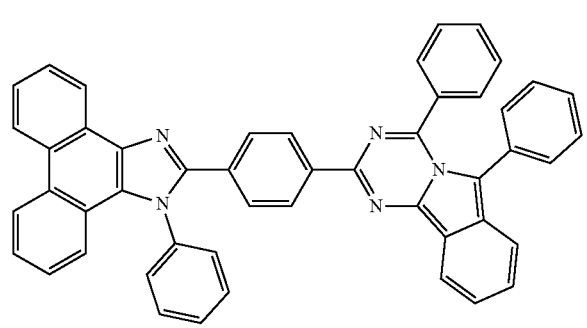
CJHP93
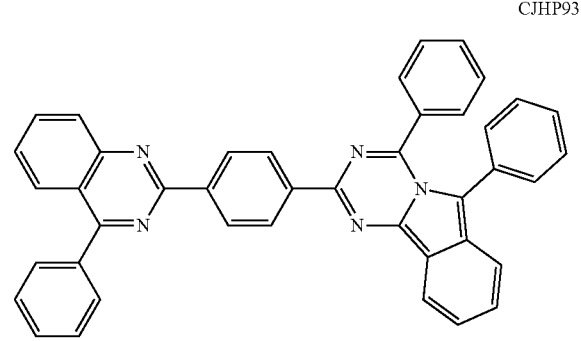

CJHP94
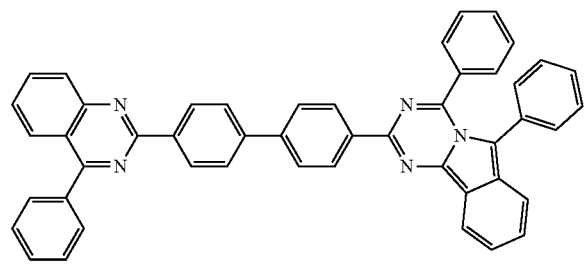
CJHP95
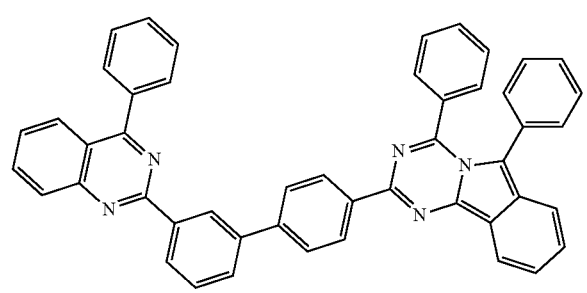
CJHP96
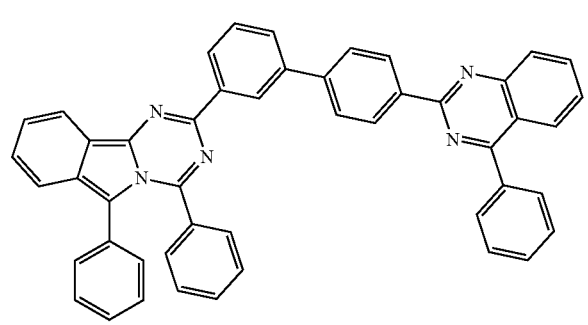
CJHP97
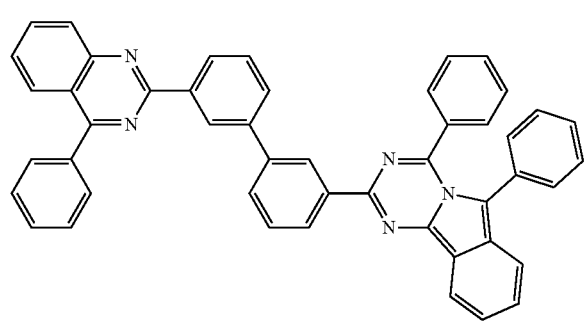
CJHP98
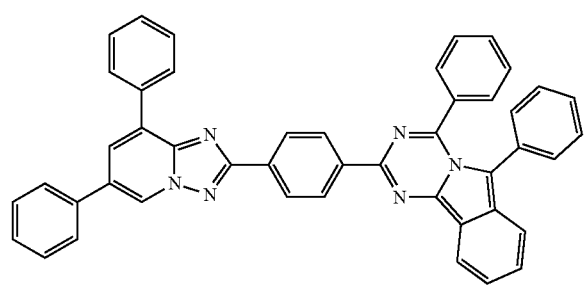
CJHP99
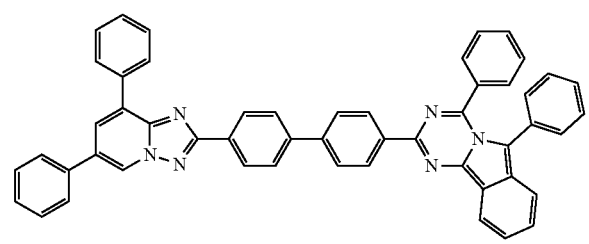
CJHP100
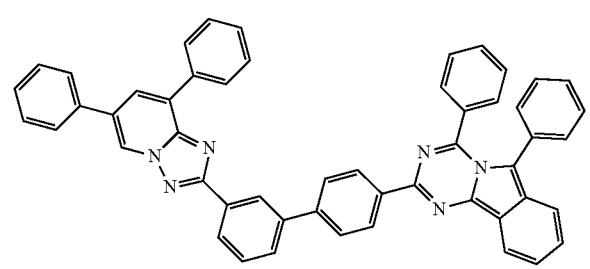
CJHP101
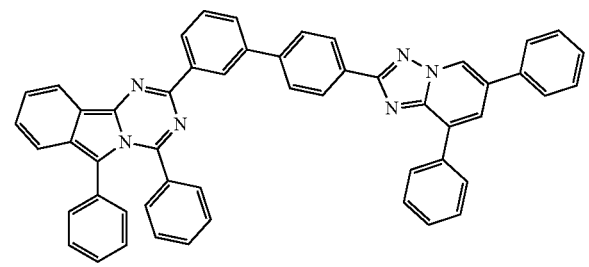
CJHP102
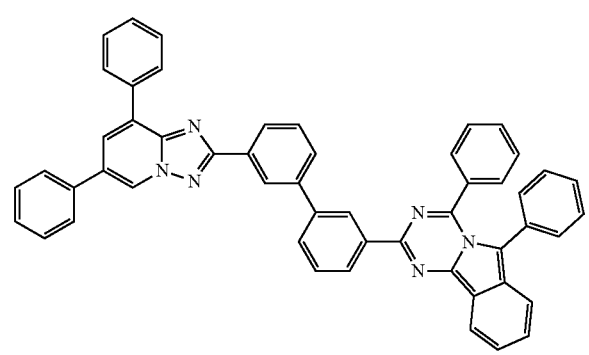
CJHP103
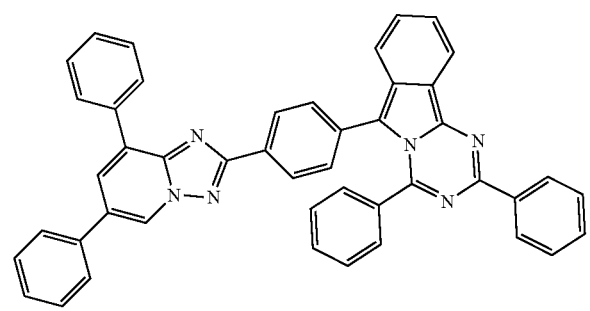

CJHP104
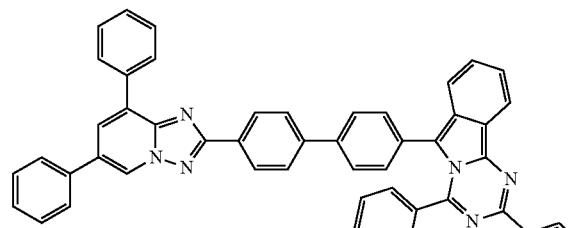
CJHP105
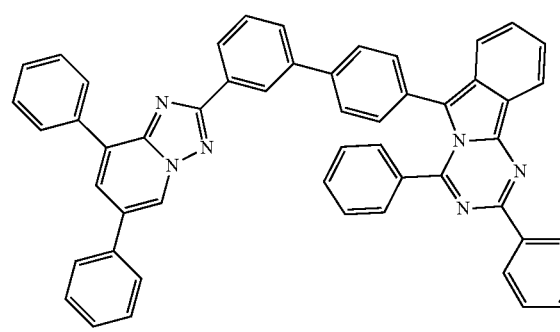
CJHP106
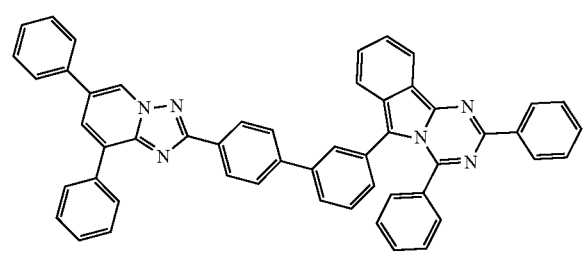
CJHP107
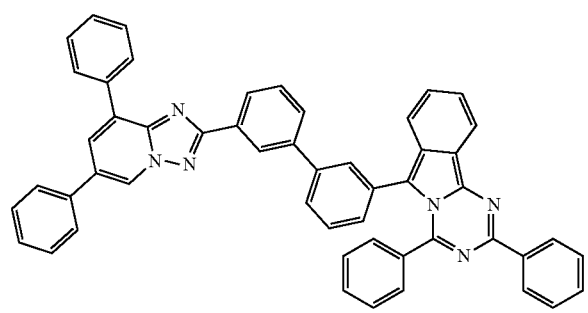
CJHP108
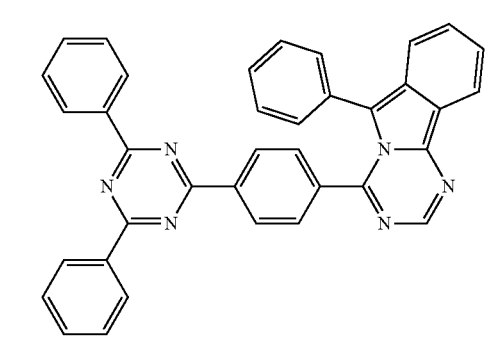
CJHP109
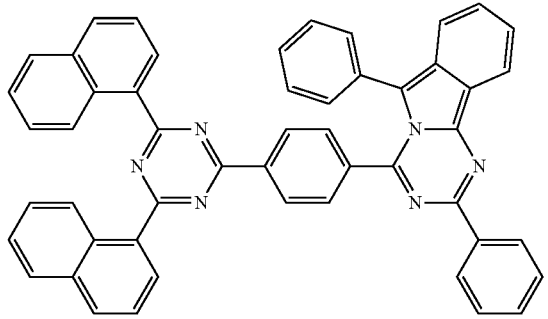
CJHP110
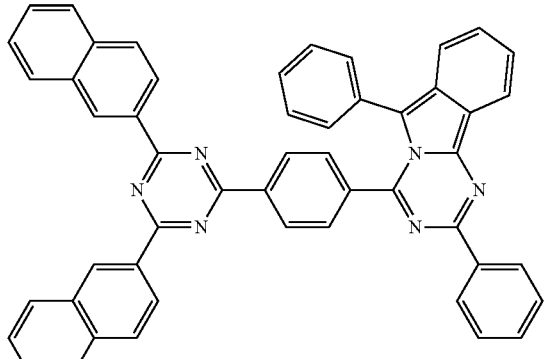
CJHP111
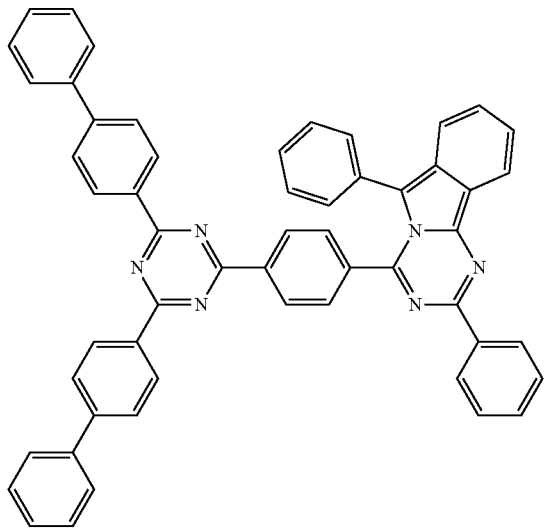

CJHP112
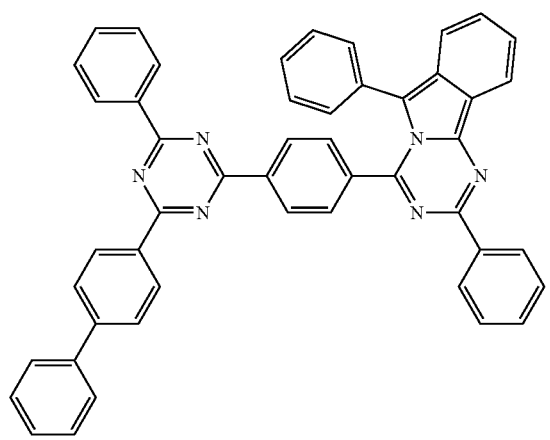
CJHP116
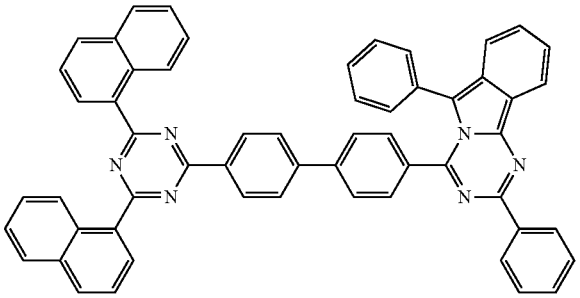
CJHP113
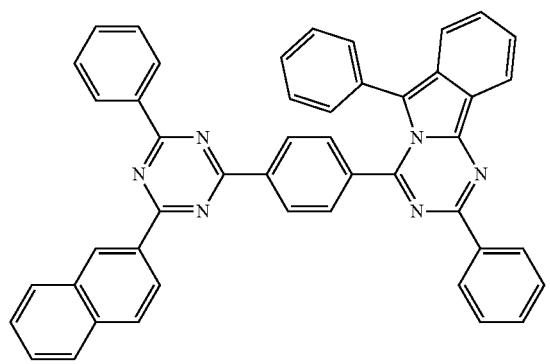
CJHP117
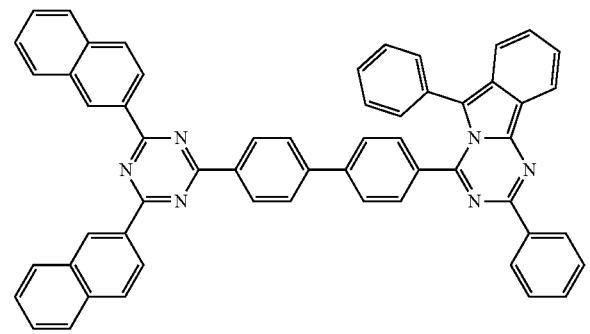
CJHP114
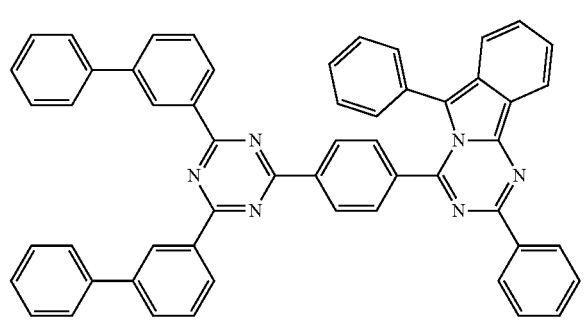
CJHP118
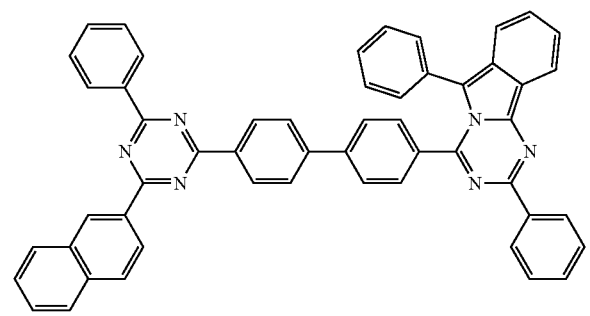
CJHP115
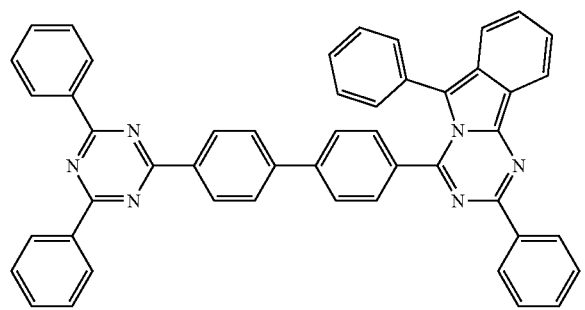
CJHP119
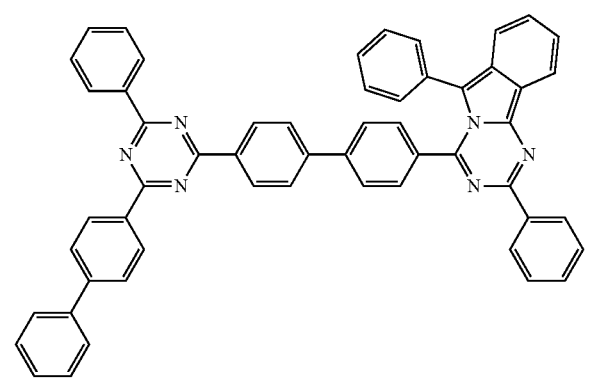

-continued
CJHP120
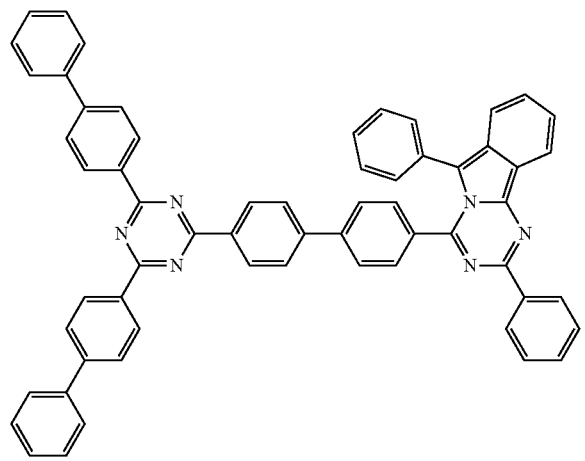
CJHP121
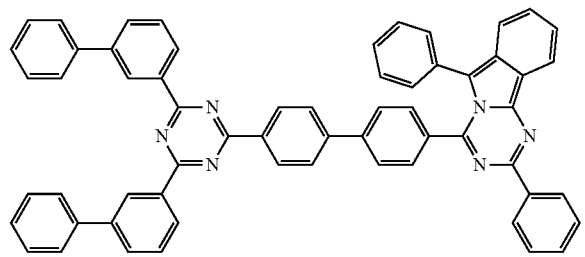
CJHP122
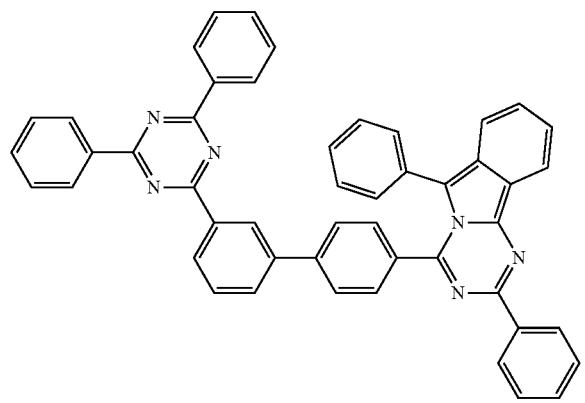
CJHP123
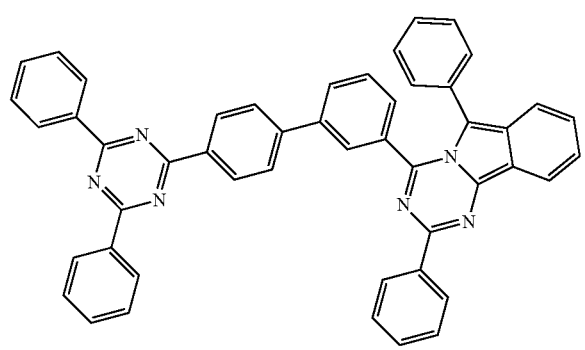
-continued
CJHP124
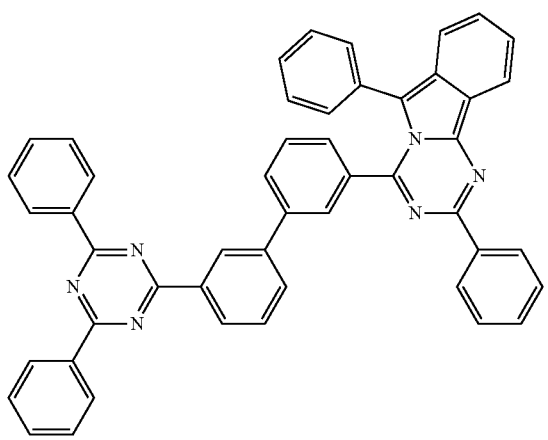
CJHP125
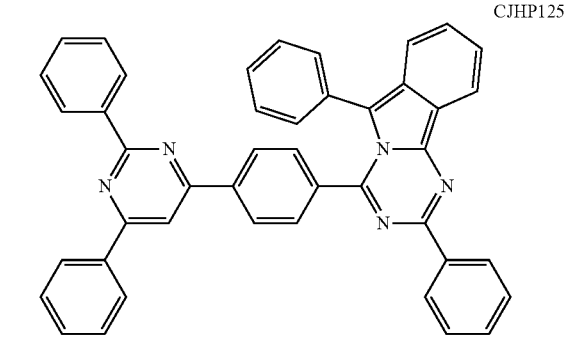
CJHP126
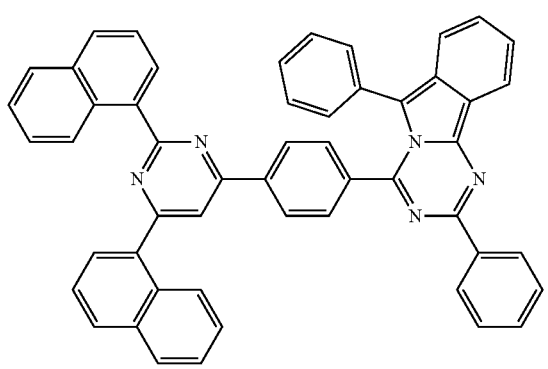
CJHP127
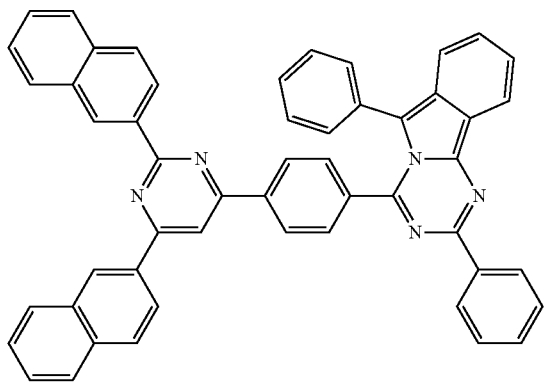

CJHP128
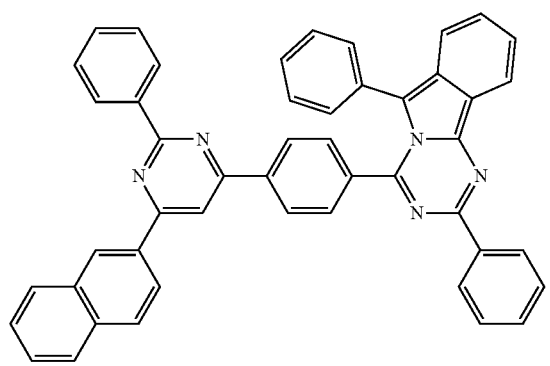
CJHP129
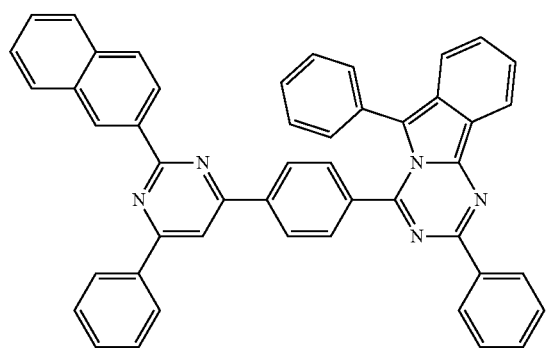
CJHP130
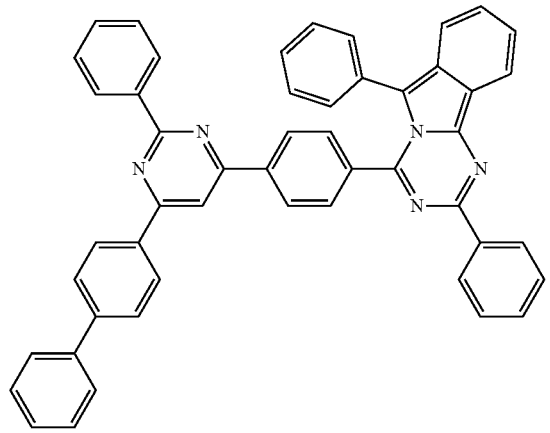
CJHP131
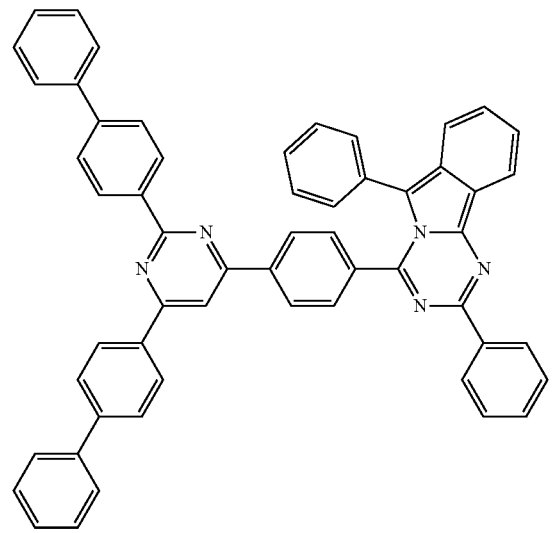
CJHP132
CJHP133
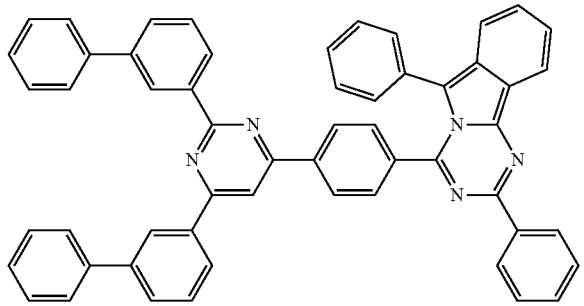
CJHP134
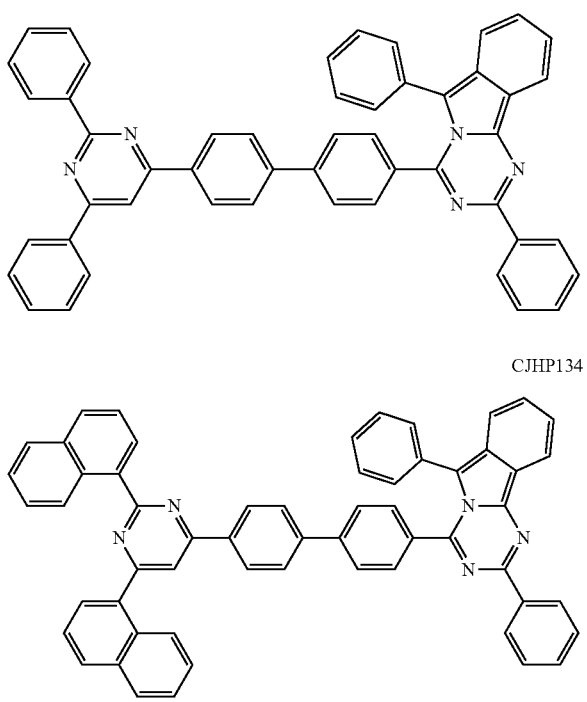

-continued
CJHP135
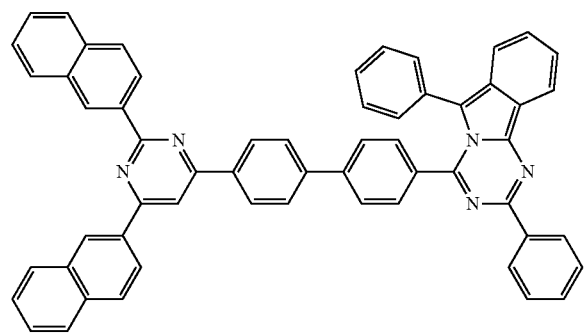
CJHP136
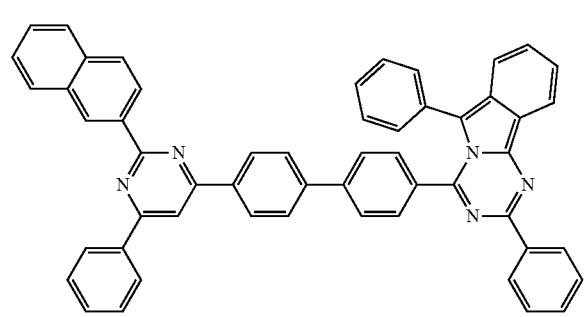
CJHP137
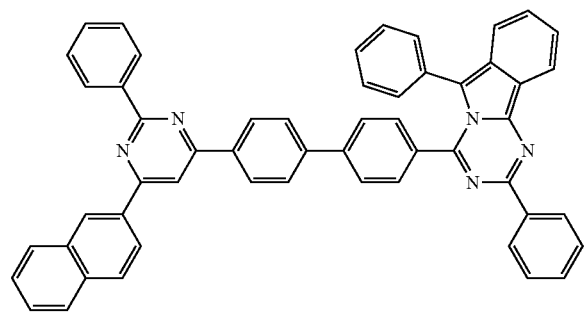
CJHP138
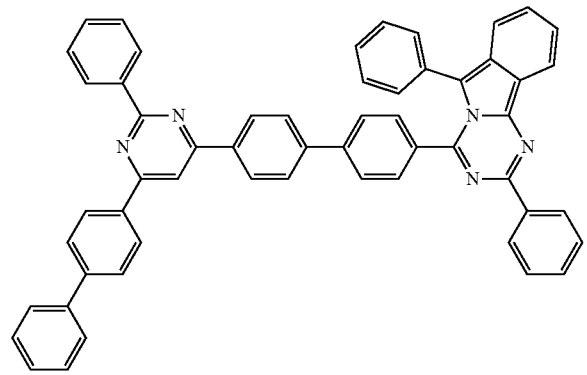
-continued
CJHP139
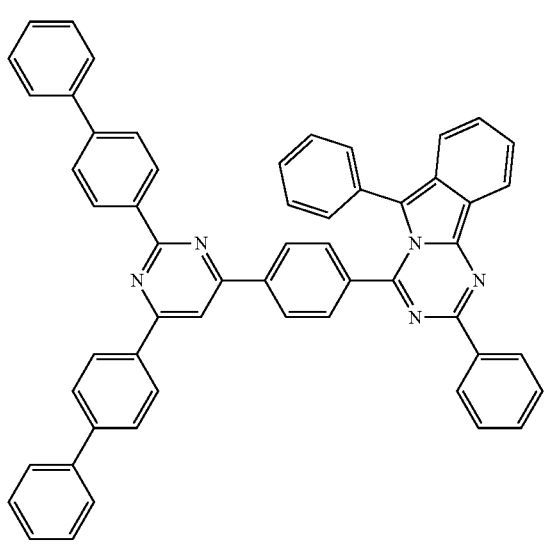
CJHP140
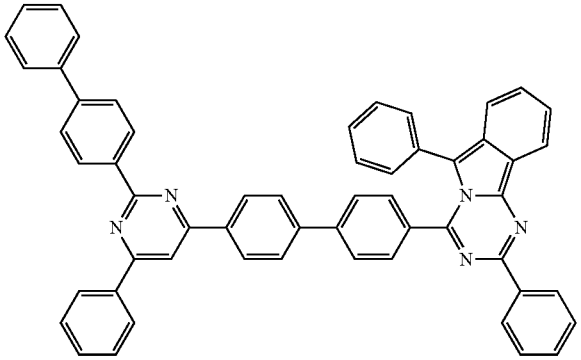
CJHP141
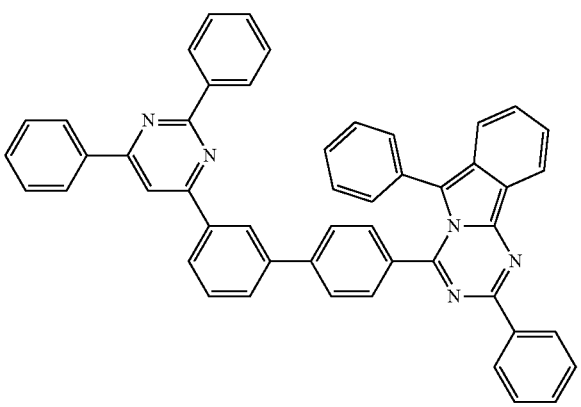

CJHP142
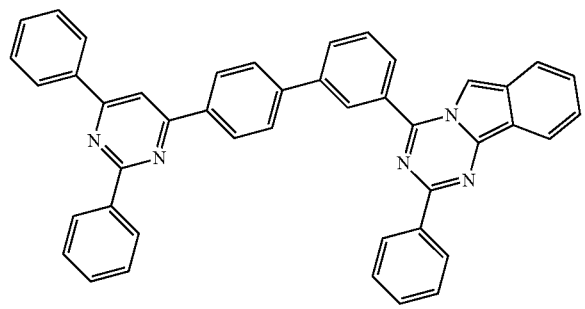
CJHP143
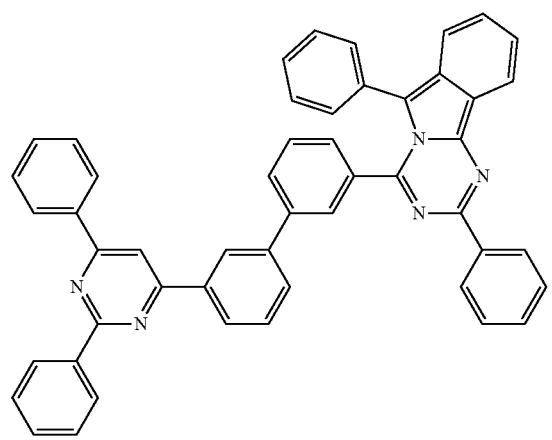
CJHP144
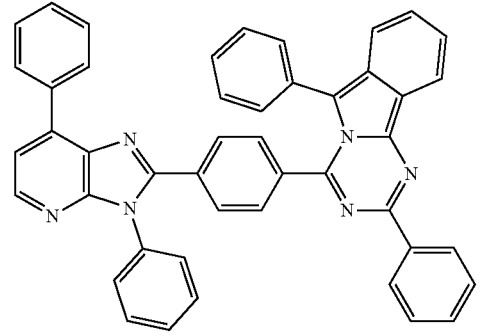
CJHP145
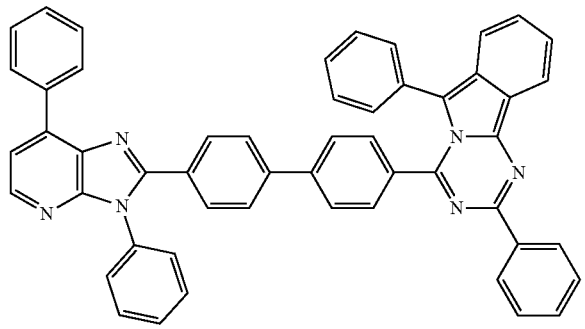
CJHP146
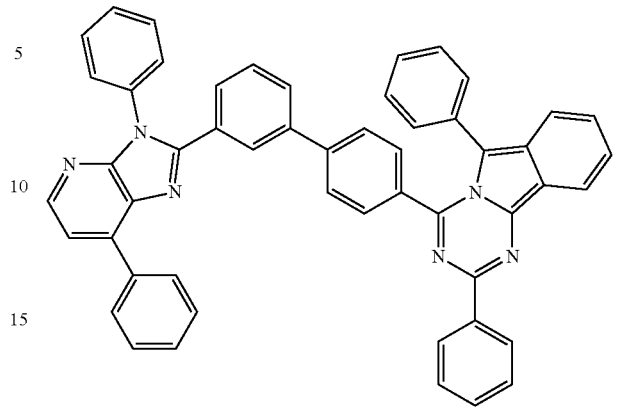
CJHP147
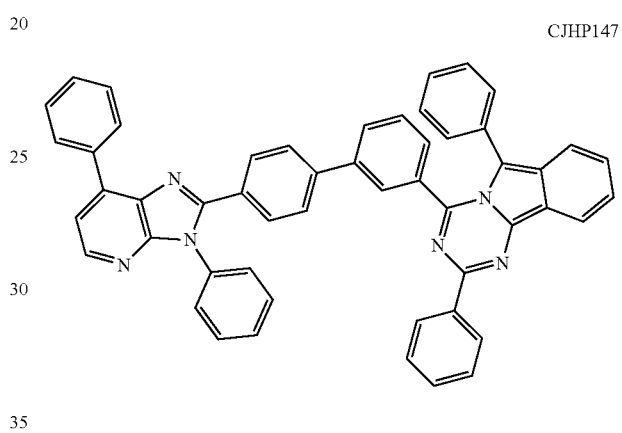
CJHP148
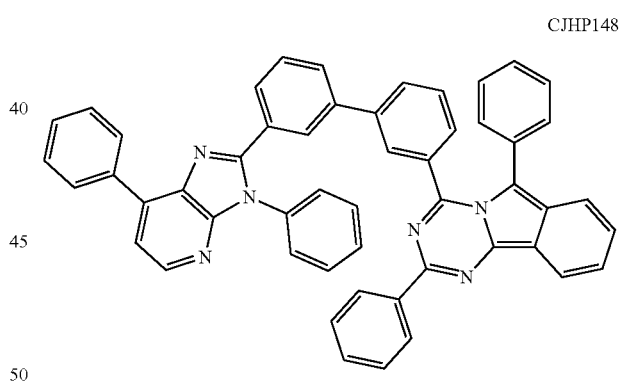
CJHP149
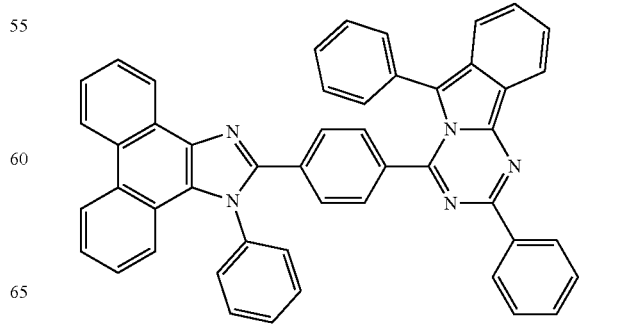

CJHP150
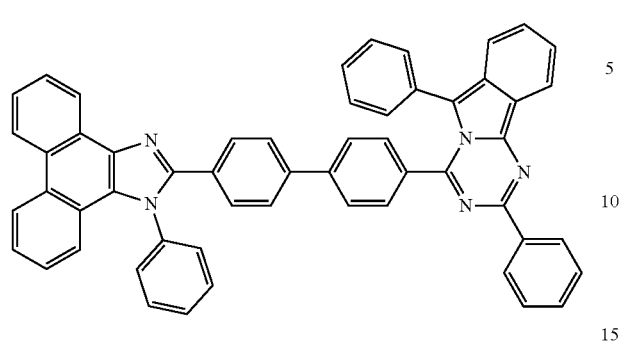
CJHP154
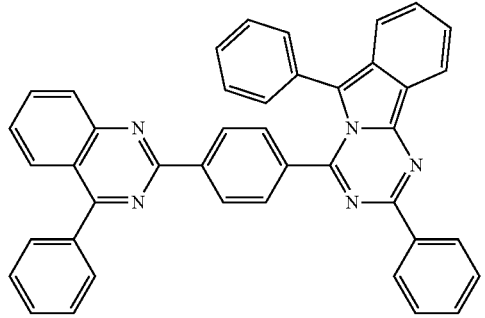
CJHP151
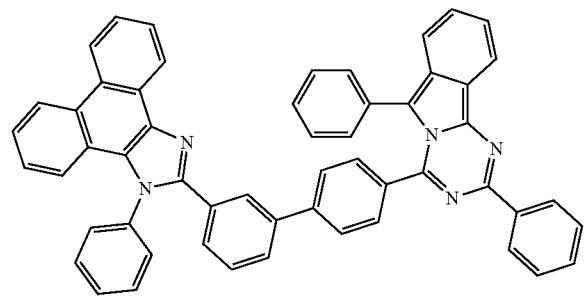
CJHP155
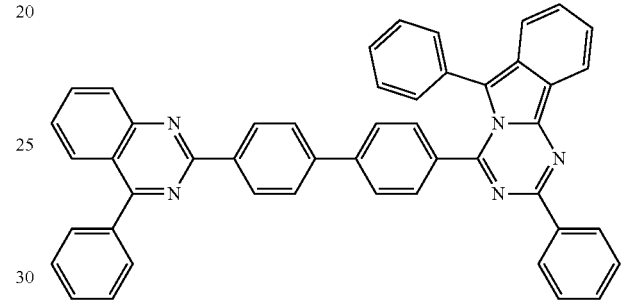
CJHP152
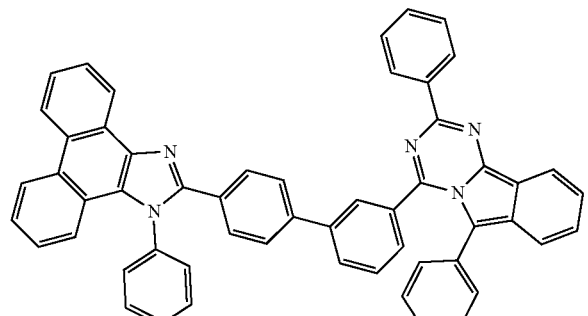
CJHP156
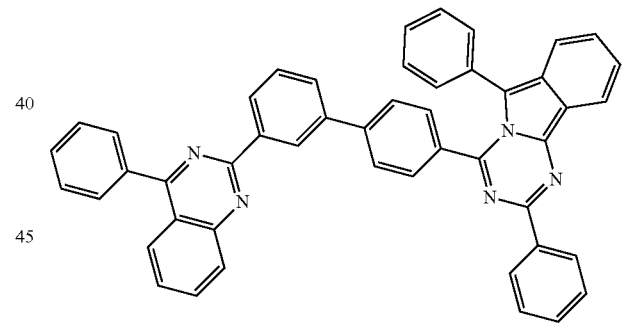
CJHP153
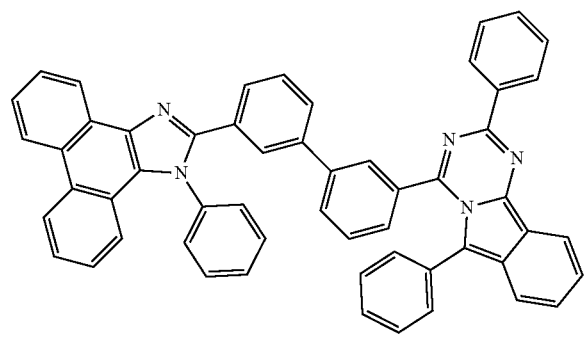
CJHP157
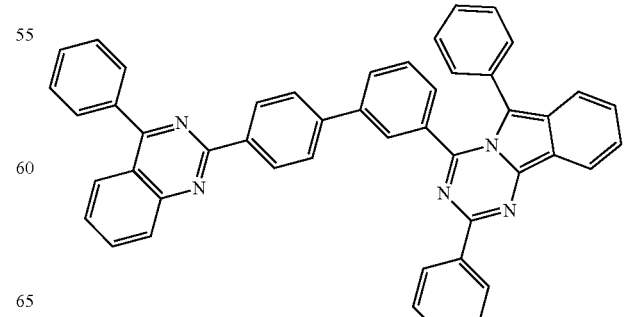

CJHP158
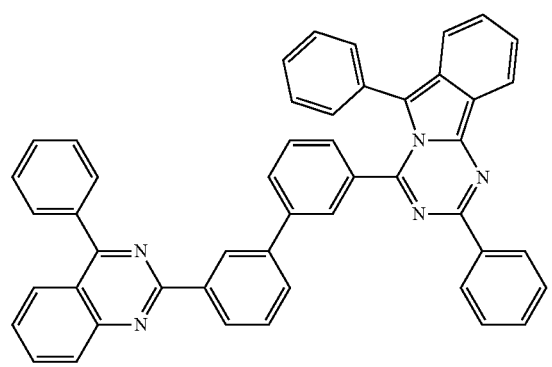
CJHP159
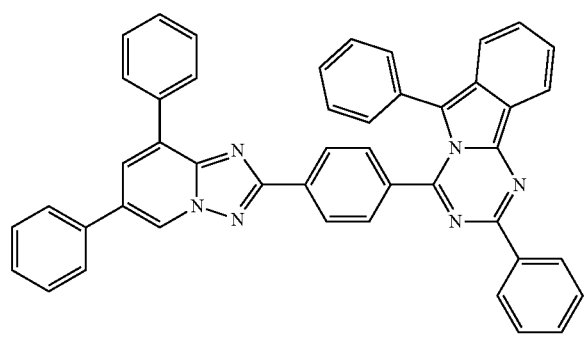
CJHP160
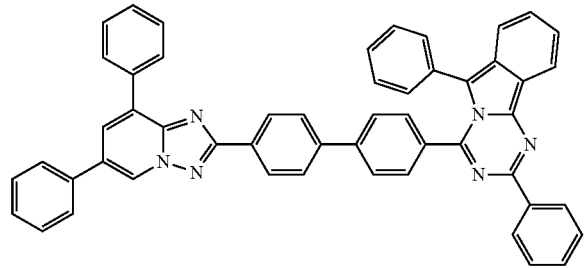
CJHP161
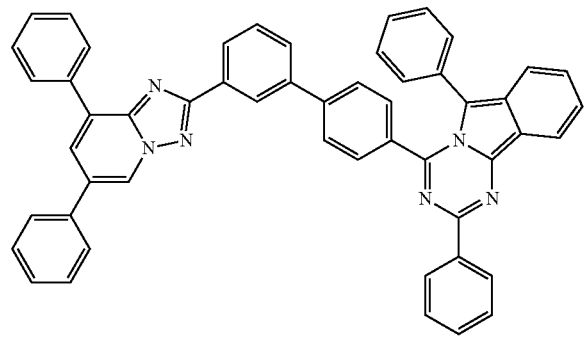
CJHP162
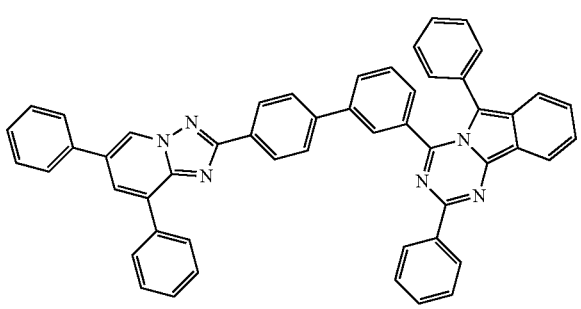
CJHP163
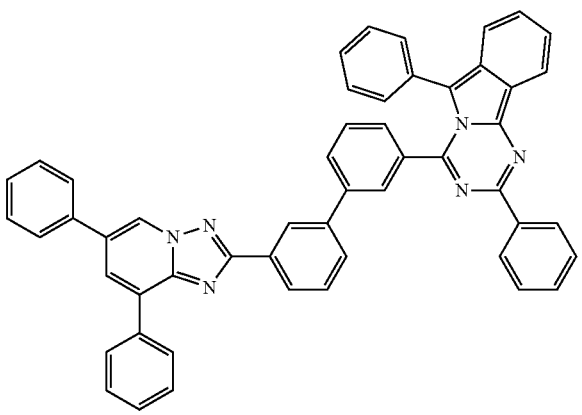
CJHP164
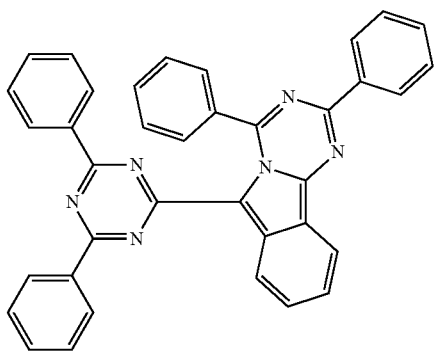
CJHP165
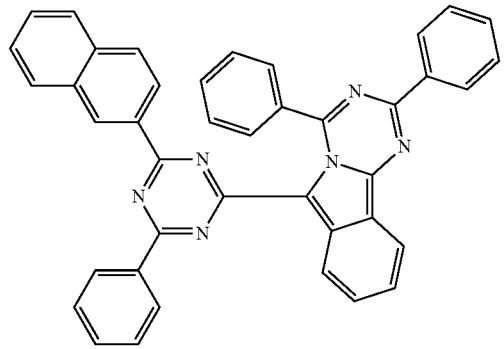

CJHP166
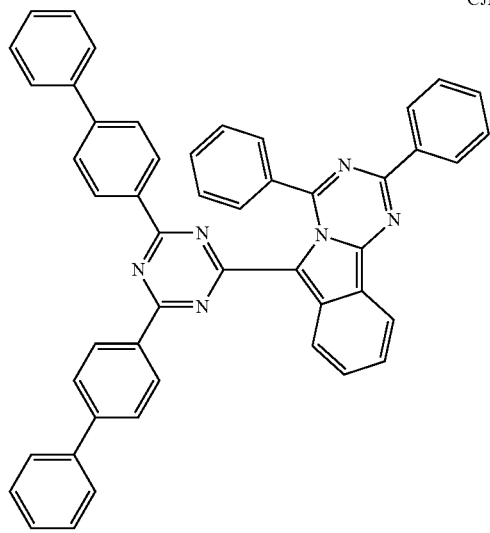
CJHP167
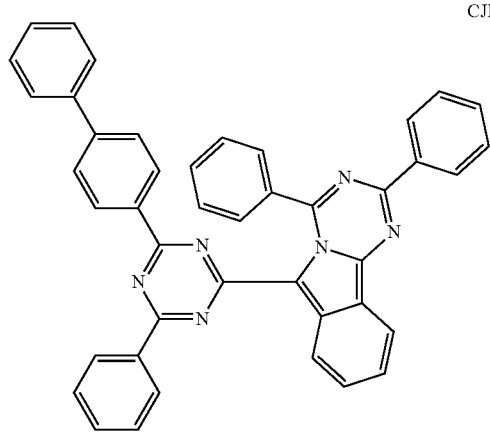
CJHP168
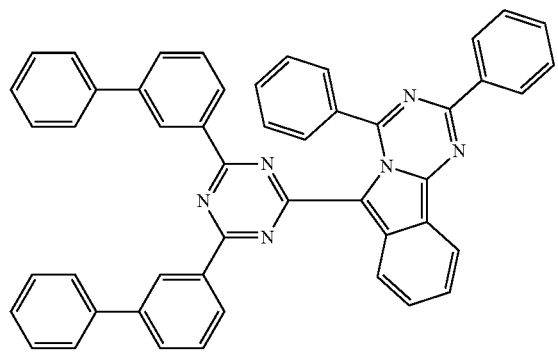
CJHP169
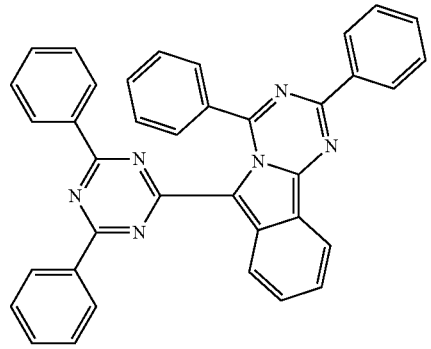
CJHP170
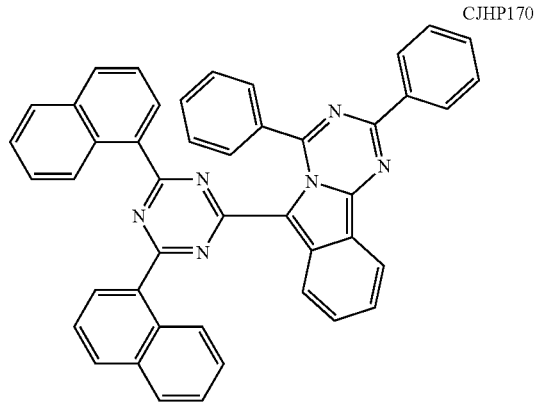
CJHP171
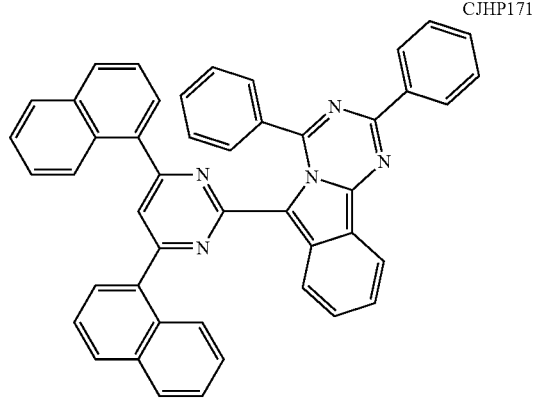
CJHP172
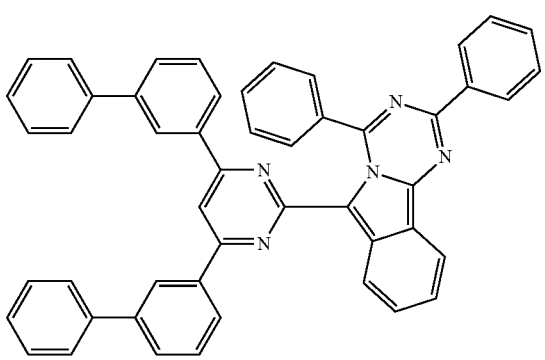

CJHP173
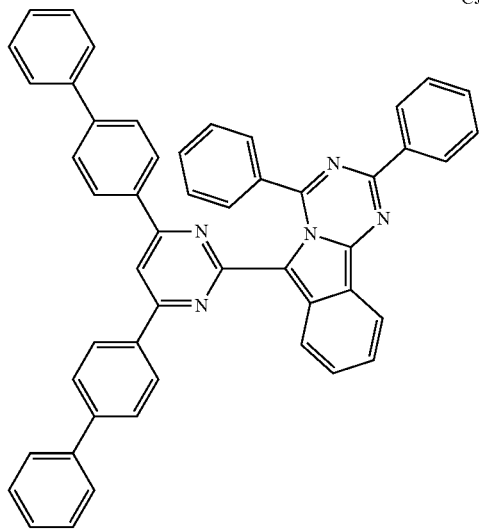
CJHP174
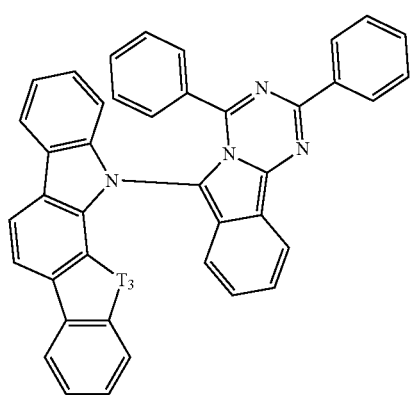
CJHP175
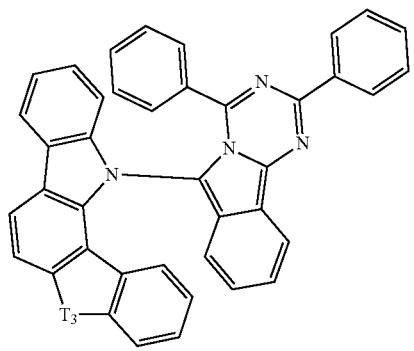
CJHP176
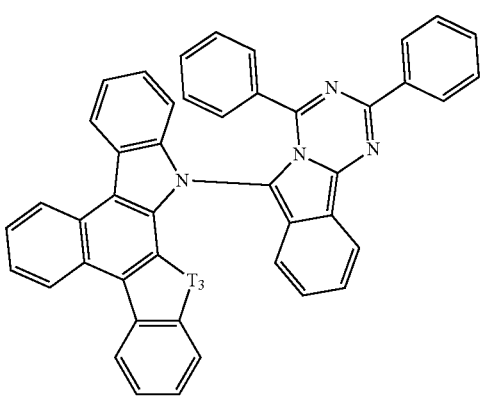
CJHP177
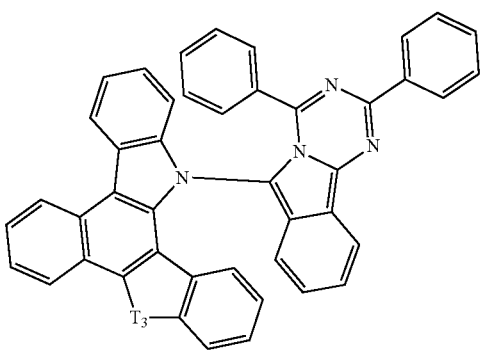
CJHP178
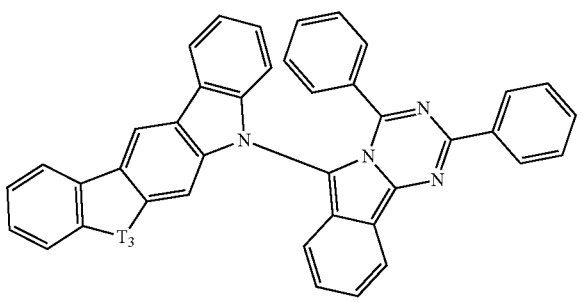
CJHP179
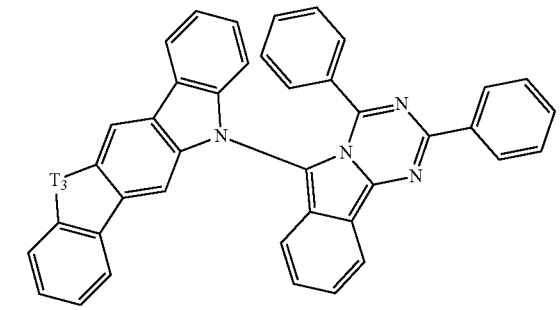

CJHP180
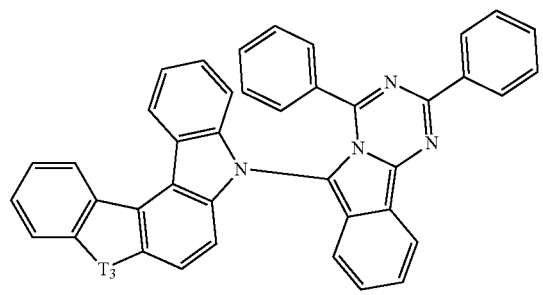
CJHP181
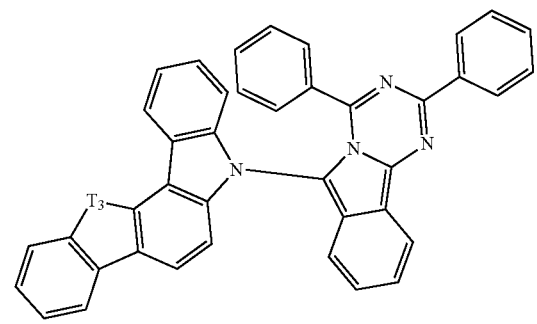
CJHP182
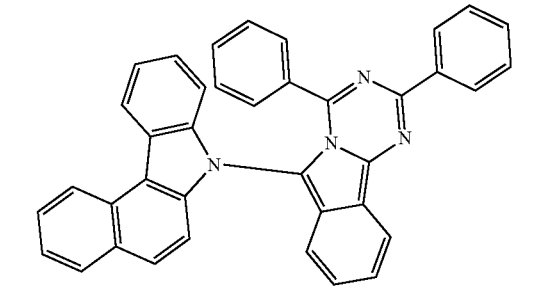
CJHP183
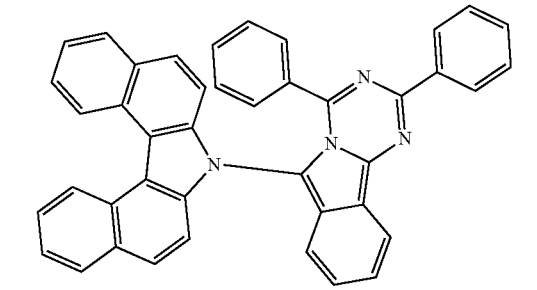
CJHP184
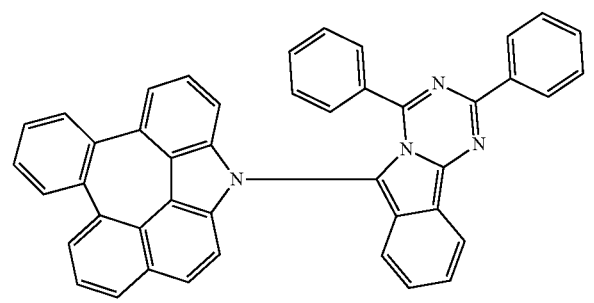
CJHP185
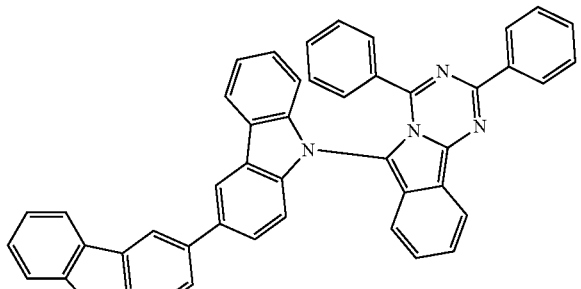
CJHP186
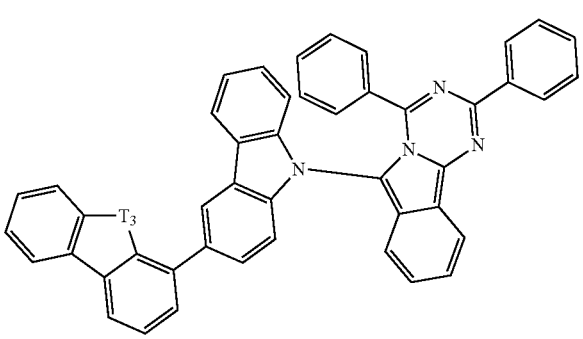
CJHP187
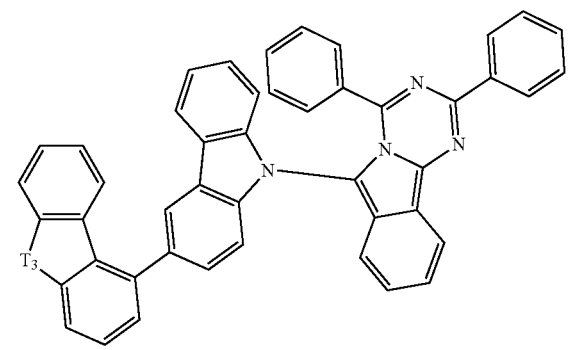
CJHP188
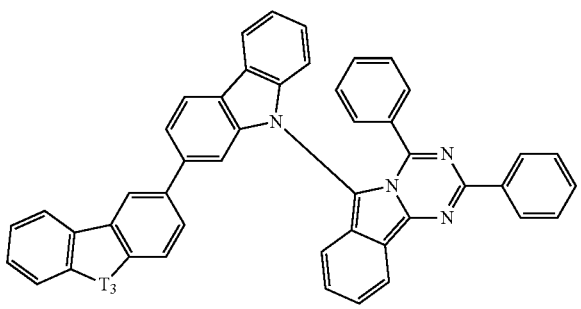

CJHP189
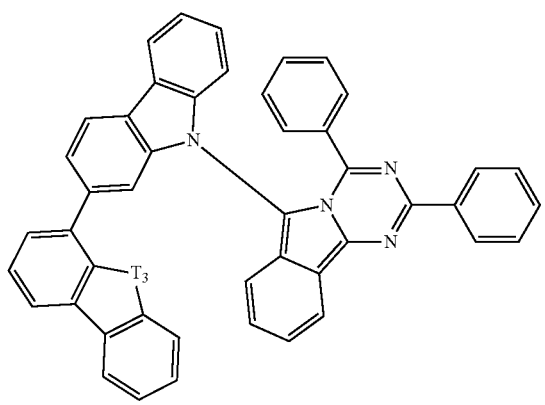
CJHP193
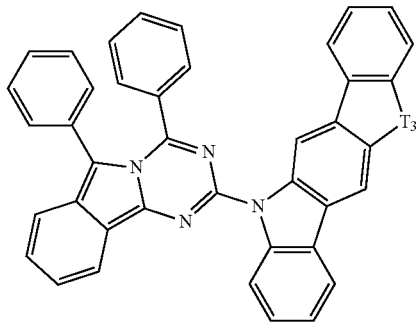
CJHP190
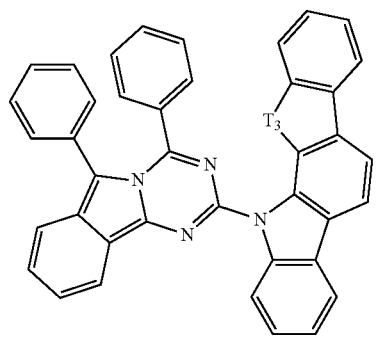
CJHP194
CJHP191
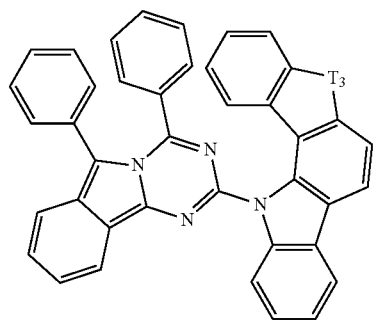
CJHP195
CJHP192
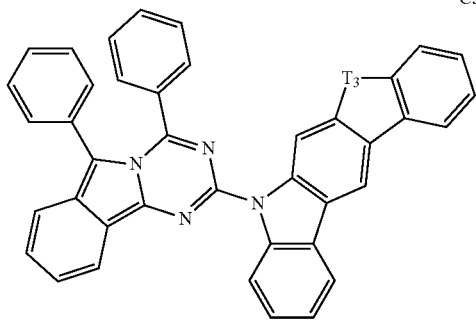
CJHP196
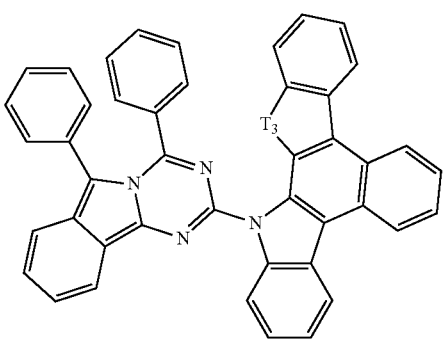

CJHP197
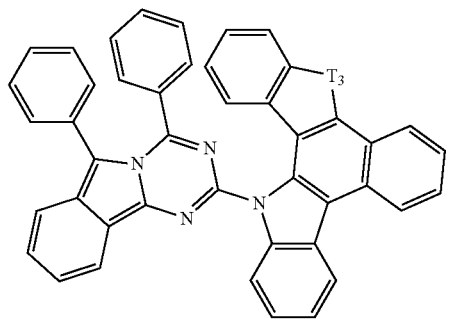
CJHP201
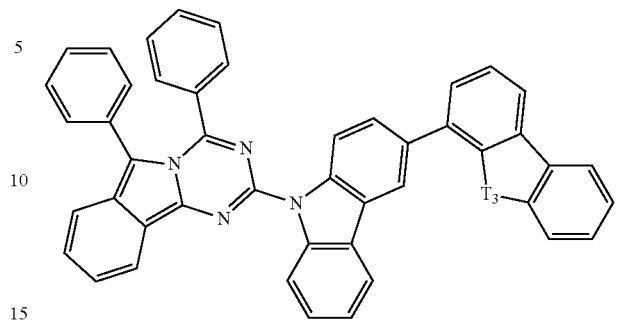
CJHP198
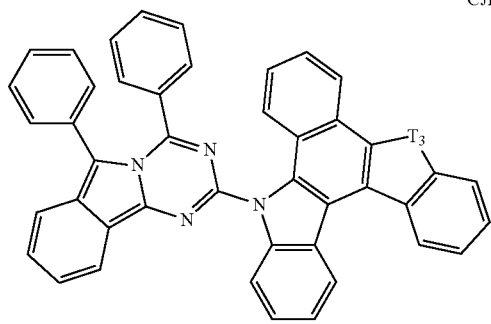
CJHP202
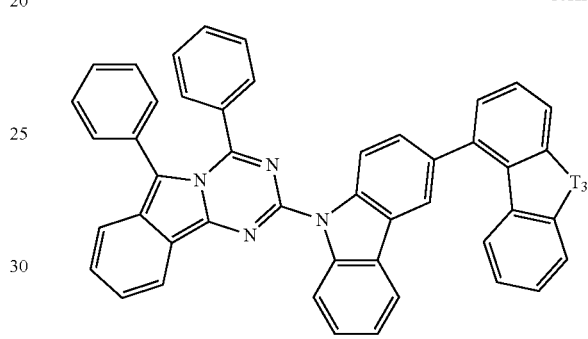
CJHP199
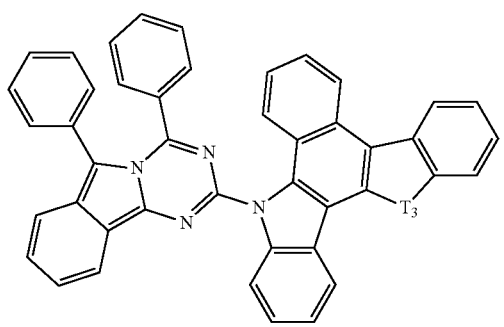
CJHP203
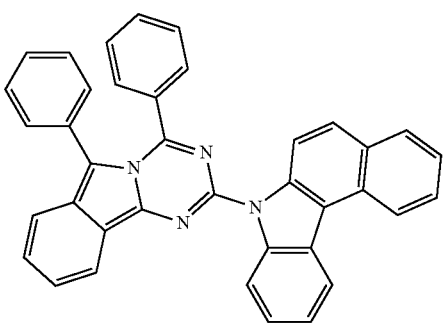
CJHP200
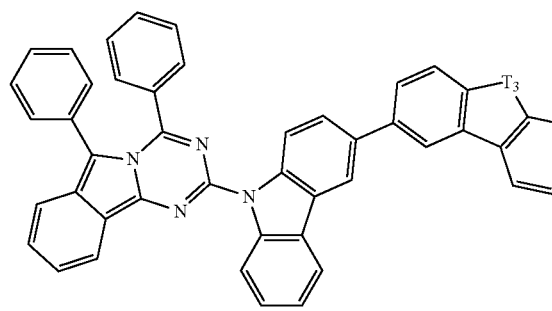
CJHP204
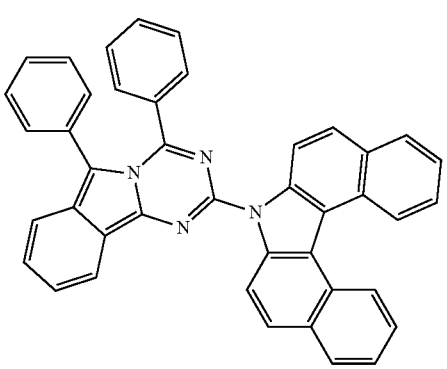

CJHP205
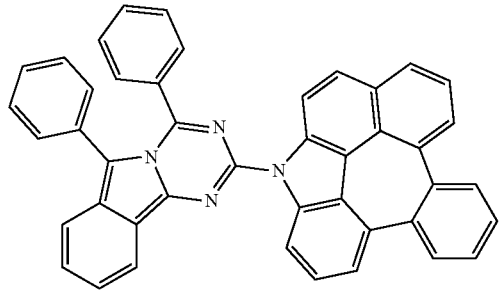
CJHP206
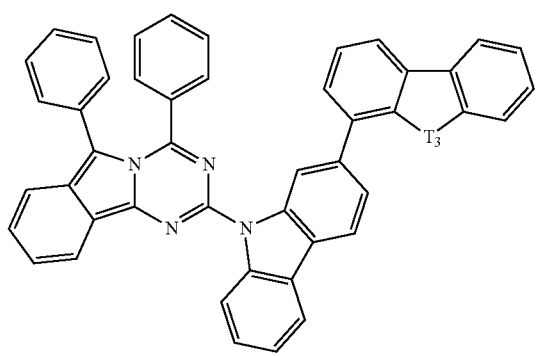
CJHP207
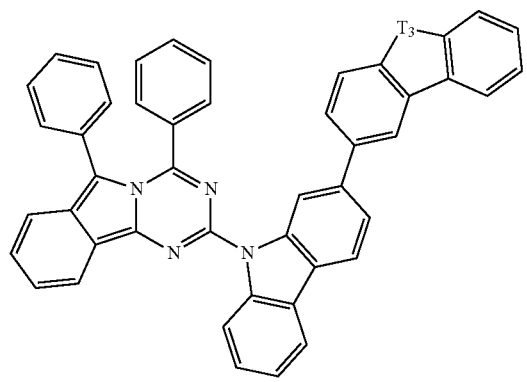
CJHP208
CJHP209
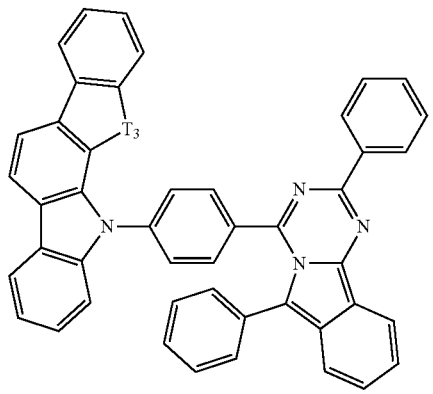
CJHP210
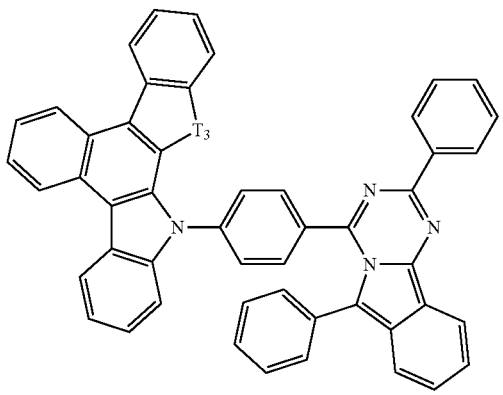
CJHP211
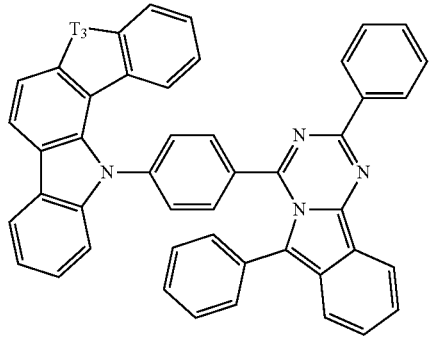
CJHP212
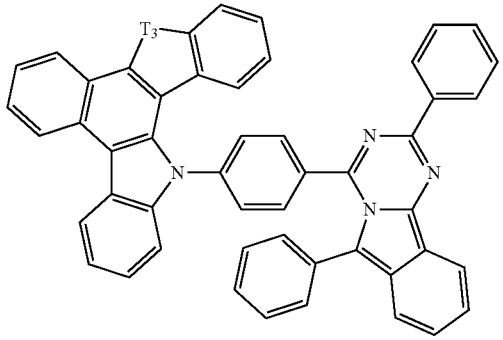

CJHP213
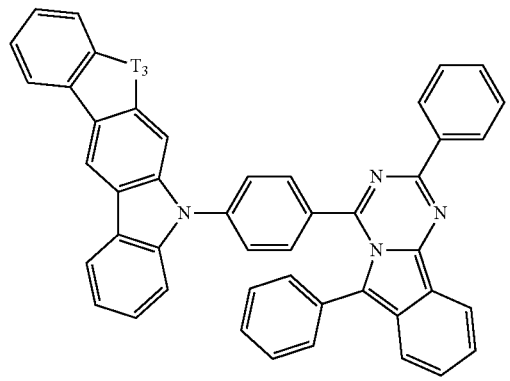
CJHP217
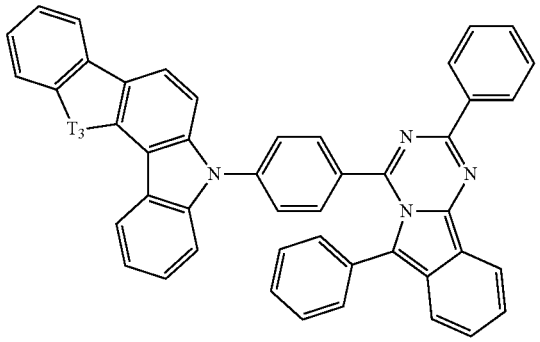
CJHP214
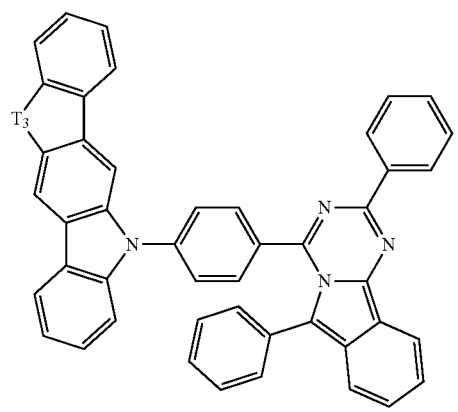
CJHP218
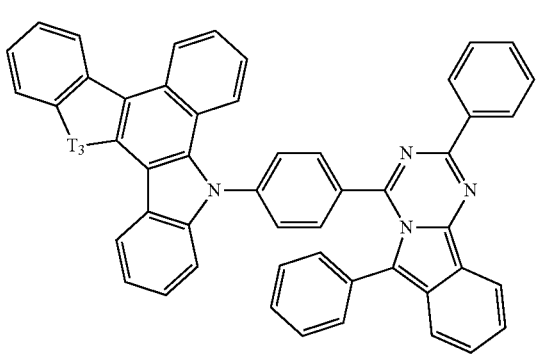
CJHP215
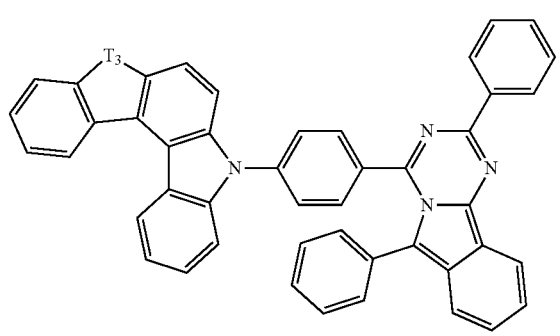
CJHP219
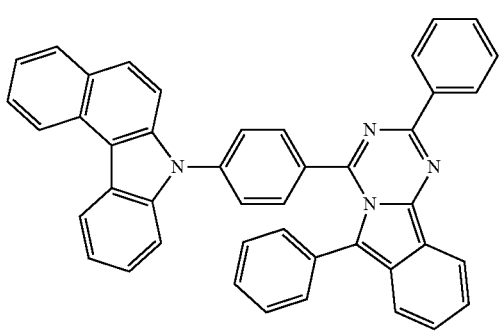
CJHP216
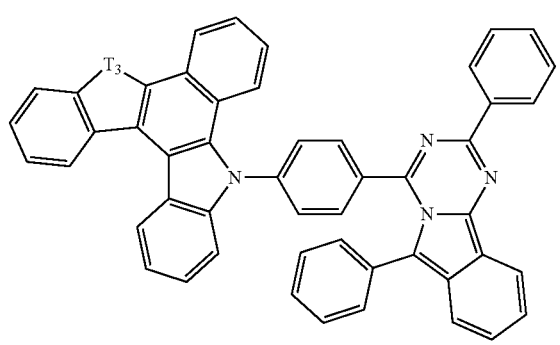
CJHP220
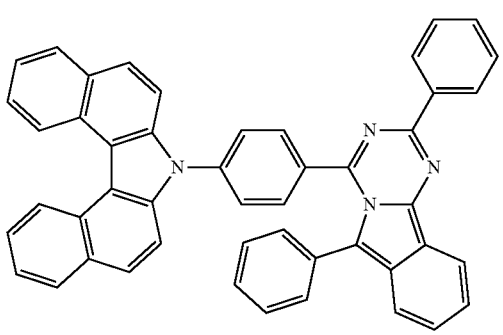

-continued
CJHP221
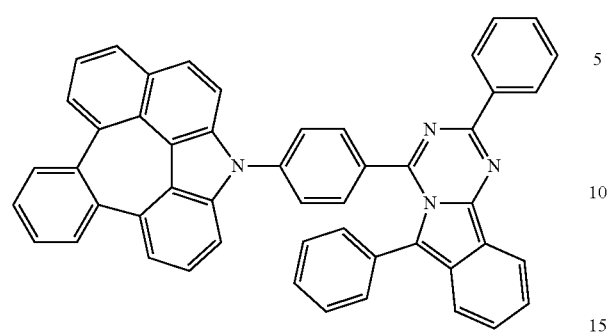
CJHP225
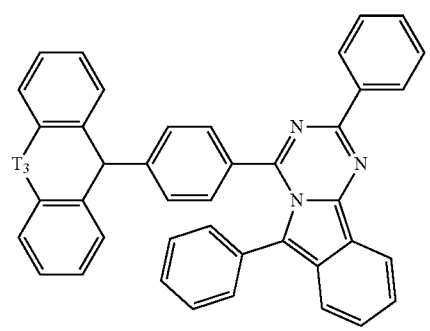
CJHP222
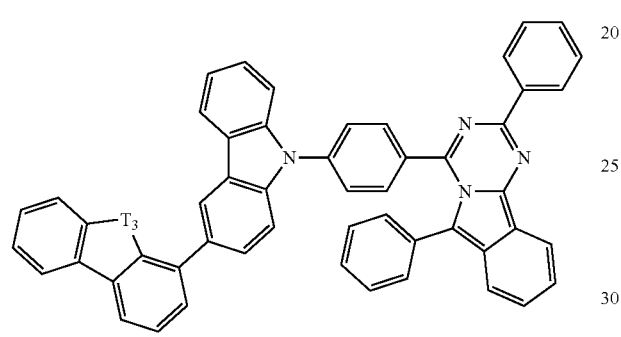
CJHP226
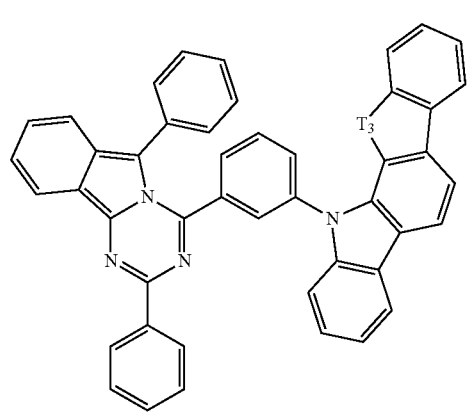
CJHP223
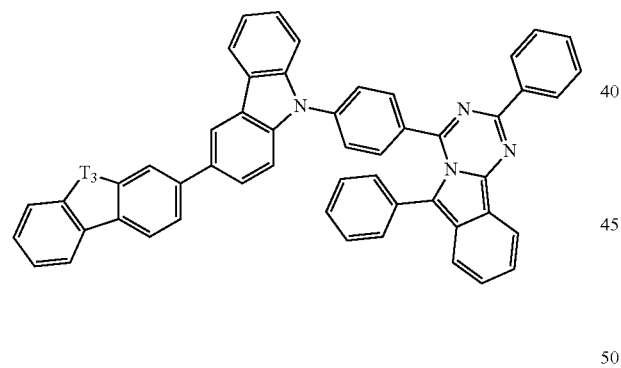
CJHP227
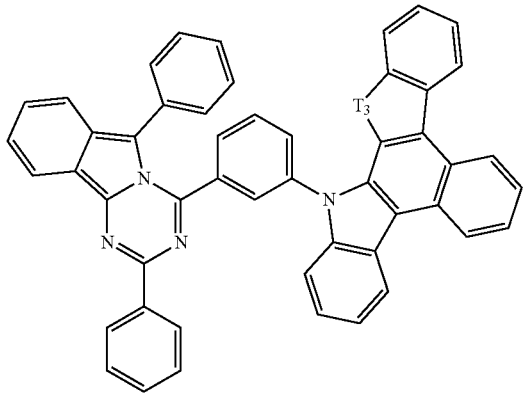
CJHP224
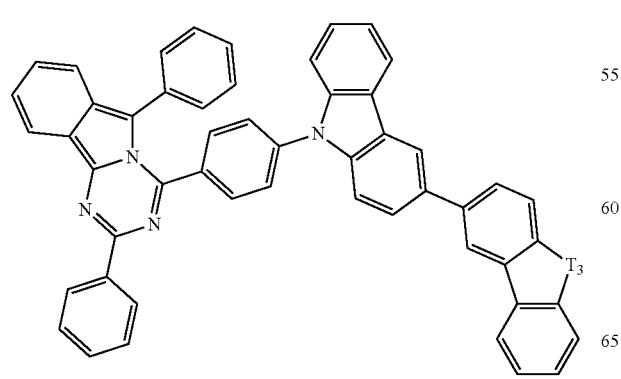
CJHP228
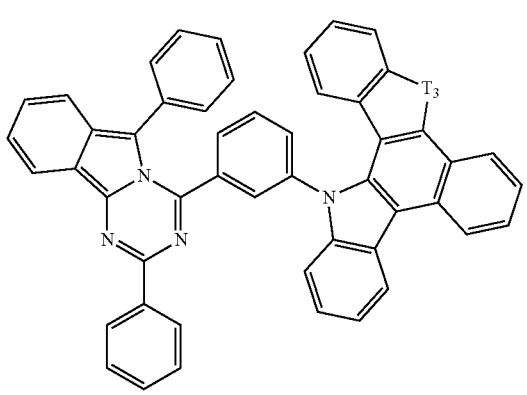

CJHP229
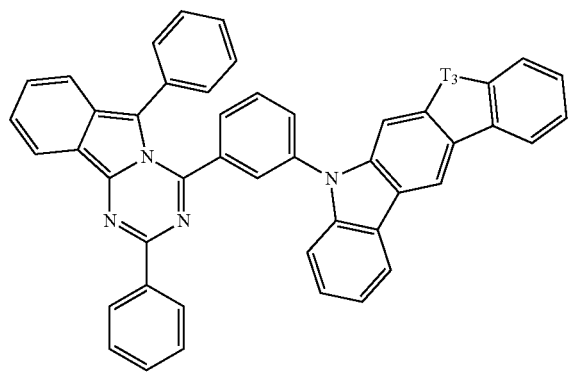
CJHP230
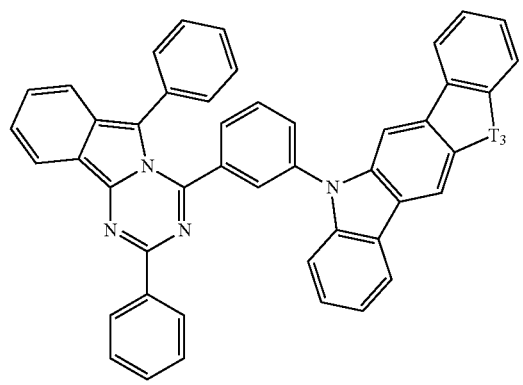
CJHP231
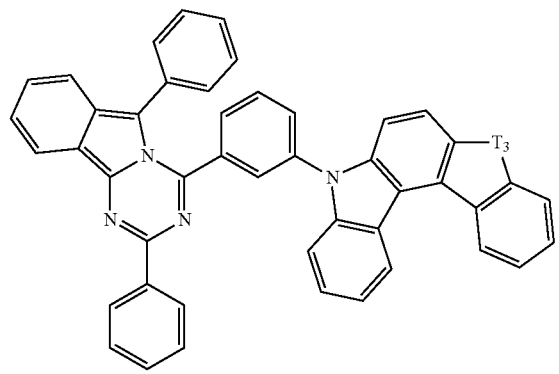
CJHP232
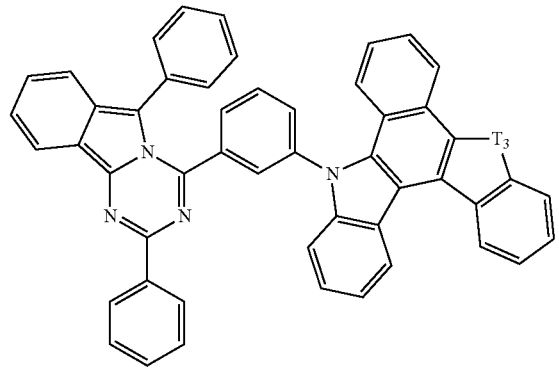
CJHP233
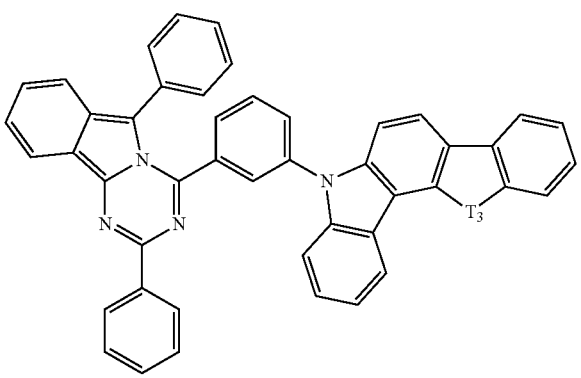
CJHP234
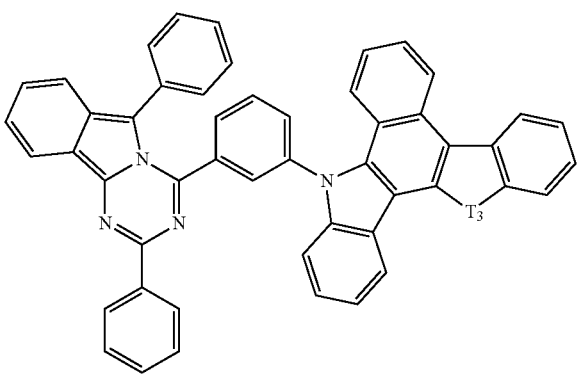
CJHP235
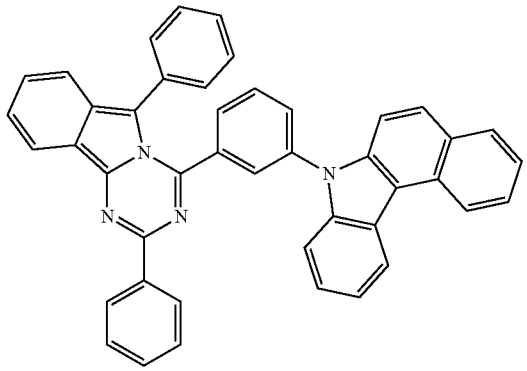
CJHP236
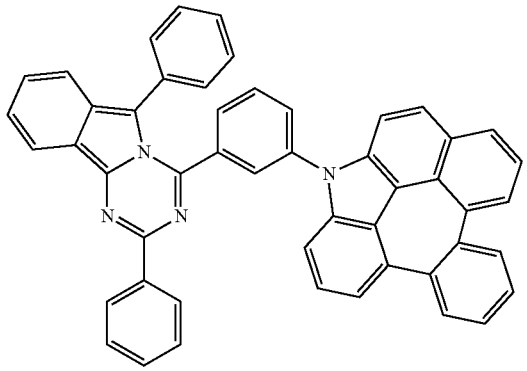

CJHP237
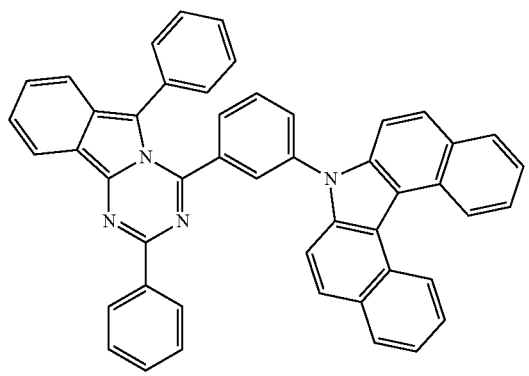
CJHP241
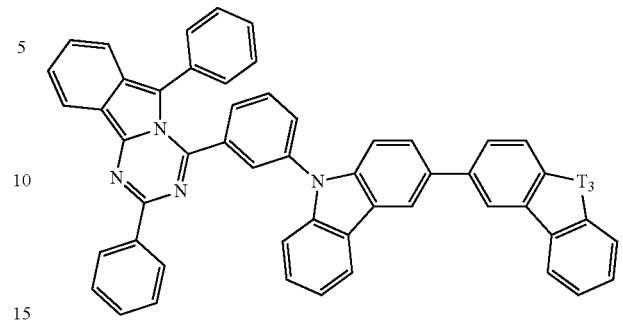
CJHP238
CJHP242
CJHP239
CJHP243
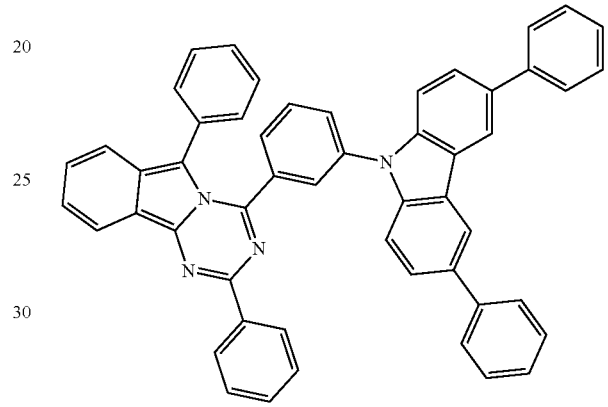
CJHP240
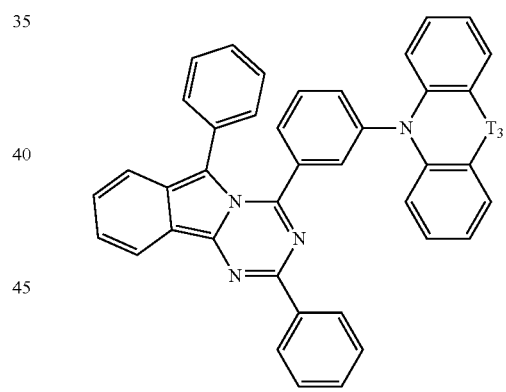
CJHP244
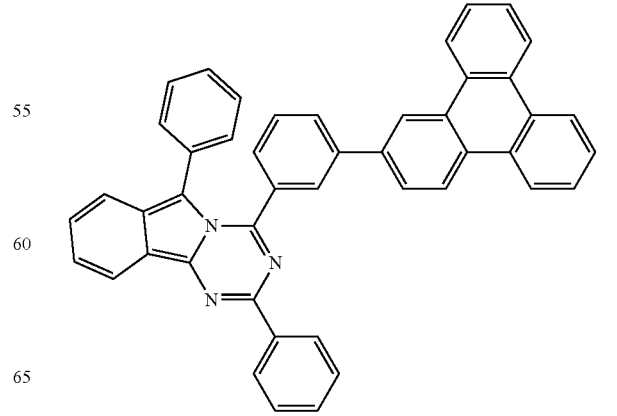

CJHP245
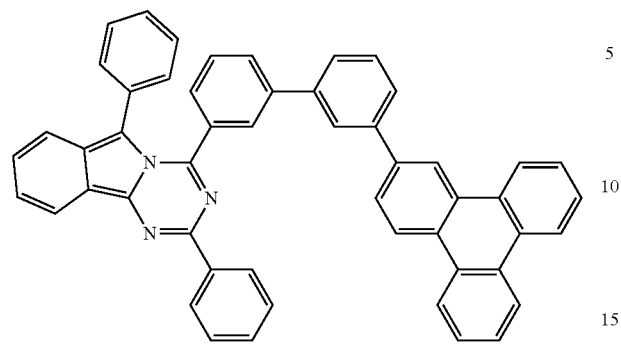
CJHP249
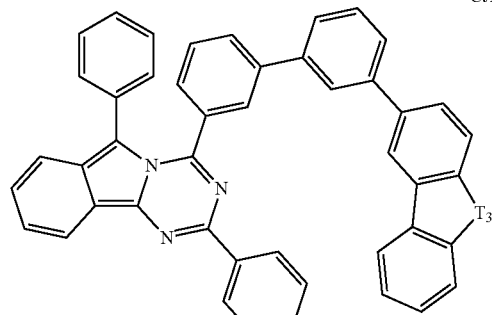
CJHP246
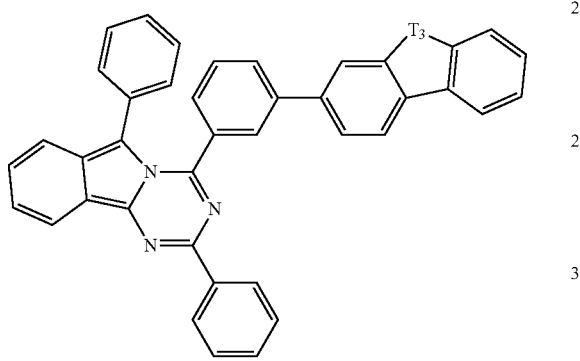
CJHP250
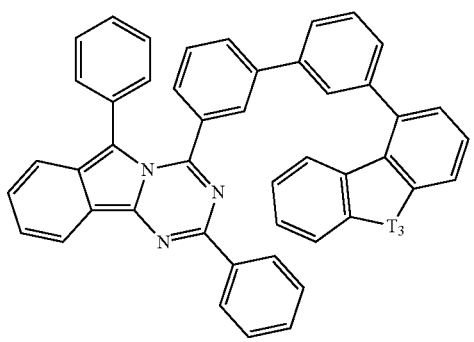
CJHP247
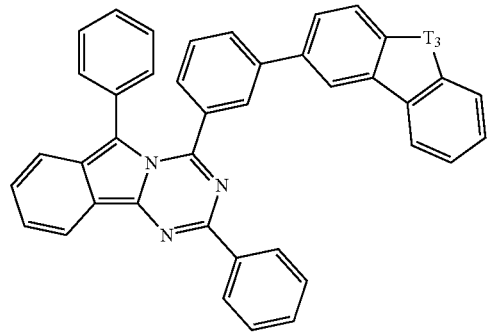
CJHP251
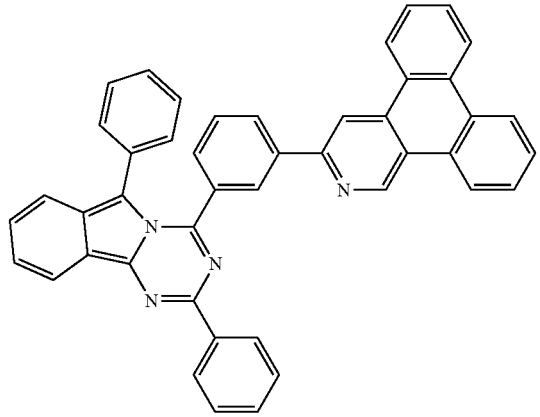
CJHP248
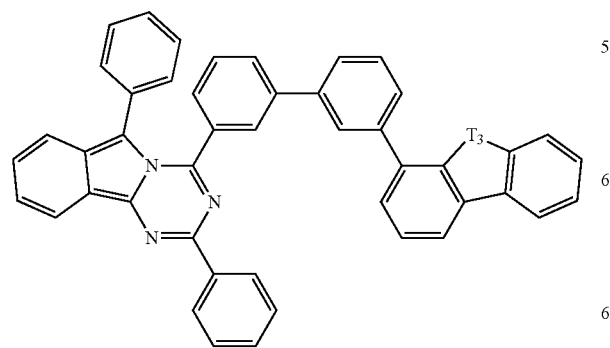
CJHP252
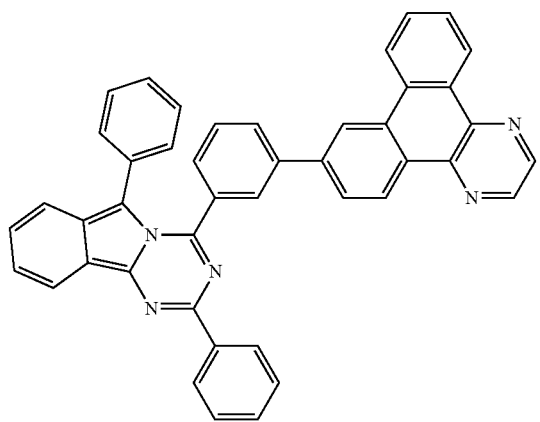

wherein T3 is *—O—*, *—S—* or one of the following strucutres:

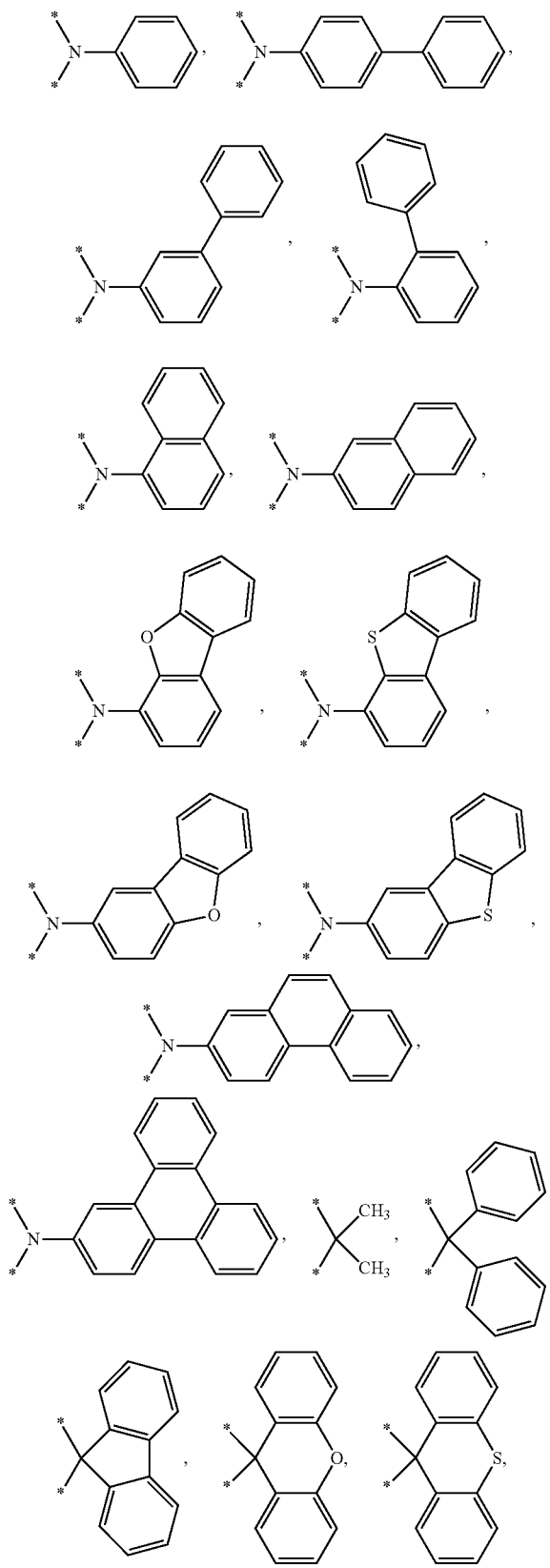

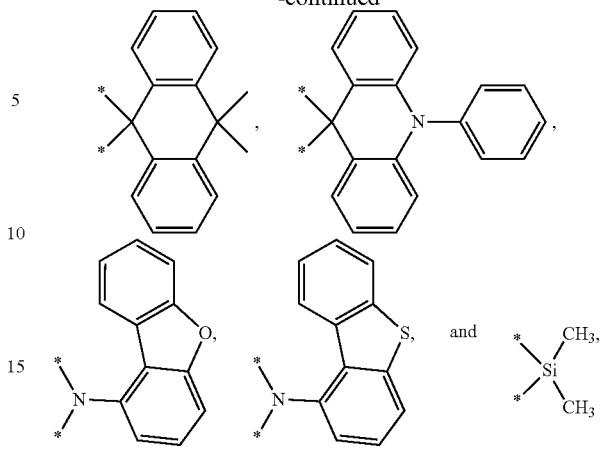

*— and —* indicate a connection bond.

The alkyl in the sense of the present invention means a monovalent functional group obtained by removing a hydrogen atom from a straight-chain or branched saturated hydrocarbon having 1 to 40 carbon atoms, and comprises, as non-limiting examples thereof, methyl, ethyl, n-propyl, isopropyl, n-butyl, isobutyl, sec-butyl, tert-butyl, 2-methylbutyl, n-pentyl, sec-pentyl, neopentyl, cyclopentyl, n-hexyl, neohexyl, cyclohexyl, n-heptyl, cycloheptyl, n-octyl, cyclooctyl, 2-ethylhexyl, and the like.

The alkoxy in the sense of the present invention is preferably alkoxy having 1-40 carbon atoms and refers to methoxy, trifluoromethoxy, ethoxy, n-propoxy, isopropoxy, n-butoxy, isobutoxy, sec-butoxy, tert-butoxy, n-pentyloxy, sec-pentyloxy, 2-methylbutoxy, n-hexyloxy, cyclohexyloxy, n-heptyloxy, cycloheptyloxy, n-octyloxy, cyclooctyloxy, 2-ethylhexyloxy, pentafluoroethoxy, 2,2,2-trifluoroethoxy, and the like.

The heteroalkyl in the sense of the present invention is preferably heteroalkyl having 1 to 40 carbon atoms, and comprises, as non-limiting examples thereof, alkoxy, alkylthio, fluorinated alkoxy, fluorinated alkylthio, particularly methoxy, ethoxy, n-propoxy, isopropoxy, n-butoxy, isobutoxy, sec-butoxy, tert-butoxy, methylthio, ethylthio, n-propylthio, isopropylthio, n-butylthio, isobutylthio, sec-butylthio, tert-butylthio, trifluoromethylthio, trifluoromethoxy, pentafluoroethoxy, pentafluoroethylthio, 2,2,2-trifluoroethoxy, 2,2,2-trifluoroethylthio, vinyloxy, vinylthio, propenyloxy, propenylthio, butenylthio, butenyloxy, pentenyloxy, pentenylthio, cyclopentenyloxy, cyclopentenylthio, hexenyloxy, hexenylthio, cyclohexenyloxy, cyclohexenylthio, ethynyloxy, ethynylthio, propynyloxy, propynylthio, butynyloxy, butynylthio, pentynyloxy, pentynylthio, hexynyloxy, and hexynylthio.

In general, the cycloalkyl and the cycloalkenyl of the present invention are preferably those having 3 to 40 carbon atoms, and comprise, as non-limiting examples thereof, cyclopropyl, cyclobutyl, cyclopentyl, cyclohexyl, norbornyl, adamantyl, cyclobutenyl, cyclopentenyl, cyclohexenyl, cycloheptyl, cycloheptenyl, and cyclooctenyl, wherein one or more —CH$_2$— groups may be substituted with the above groups. In addition, one or more hydrogen atoms may also be substituted with a deuterium atom, a halogen atom or a nitrile group.

The heterocycloalkyl of the present invention means a monovalent functional group obtained by removing a hydrogen atom from a non-aromatic hydrocarbon having 3 to 40 carbon atoms. In such a case, one or more carbons, preferably 1 to 3 carbons, in a ring are substituted with a hetero atom such as nitrogen, oxygen, or sulfur, and as non-limiting examples thereof, morpholine, pyran, piperazine, and the like.

The alkenyl of the present invention may be a monovalent functional group obtained by removing a hydrogen atom from a straight-chain or branched unsaturated hydrocarbon having one or more carbon-carbon double bonds and 2 to 40 carbon atoms. As non-limiting examples thereof, there are vinyl, allyl, isopropenyl, 2-butenyl, heptenyl, octenyl, and the like.

The alkynyl of the present invention refers to a monovalent functional group obtained by removing a hydrogen atom from a straight-chain or branched unsaturated hydrocarbon having one or more carbon-carbon triple bonds and 2 to 40 carbon atoms. As non-limiting examples thereof, there are ethynyl, propynyl, butynyl, pentynyl, hexynyl, heptynyl, octynyl, and the like.

The aryl of the present invention means a monovalent functional group obtained by removing a hydrogen atom from a single ring or an aromatic hydrocarbon combining two or more 6- to 60-carbon atom rings. In such a case, the two or more rings may be attached to each other or in a fused form. As non-limiting examples thereof, there are phenyl, naphthyl, anthryl, benzanthryl, phenanthryl, pyrenyl, chrysenyl, perylenyl, fluoranthenyl, tetracenyl, pentacenyl, benzopyrenyl, biphenyl, diphenyl, terphenyl, trimericphenyl, fluorenyl, spirobifluorenyl, dihydrophenanthryl, dihydropyrenyl, tetrahydropyrenyl, indenyl, cis- or trans-indenofluorenyl, cis- or trans-indenocarbazolyl, cis- or trans-indolocarbazolyl, trimeric indenyl, trimeric isoindenyl, spiro-trimeric indenyl, spiro-trimeric isoindenyl, furanyl, benzofuranyl, isobenzofuranyl, dibenzofuranyl thienyl, benzothienyl, isobenzothienyl, dibenzothienyl, pyrrolyl, indolyl, isoindolyl, carbazolyl, pyridyl, quinolyl, isoquinolyl, acridinyl, phenanthridinyl, benzo[5,6]quinolyl, benzo[6,7]quinolyl, benzo[7,8]quinolyl, phenothiazinyl, phenoxazine, pyrazolyl, indazolyl, imidazolyl, benzimidazolyl, naphthoimidazolyl, phenanthroimidazolyl, pyridoimidazolyl, pyrazinoimidazolyl, quinoxalimidazolyl, oxazolyl, benzoxazolyl, naphthooxazolyl, anthraoxazolyl, phenanthrooxazolyl, isoxazolyl, 1,2-thiazolyl, 1,3-thiazolyl, benzothiazolyl, pyridazinyl, hexaazabenzophenanthryl, benzopyrazinyl, pyrimidinyl, benzopyrimidinyl, quinoxalinyl, 1,5-diazanthroyl, 2,7-diazapyrenyl, 2,3-diazapyrenyl, 1,6-diazapyrenyl, 1,8-diazapyrenyl, 4,5-diazapyrenyl, 4,5,9,10-tetraazaperylenyl, pyrazinyl, phenazinyl, phenoxazinyl, phenothiazinyl, a fluorubin group, naphthyridinyl, azacarbazolyl, benzocarbazinyl, carbolinyl, phenanthrolinyl, 1,2,3-triazolyl, 1,2,4-triazolyl, benzotriazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,3,5-triazinyl, 1,2,4-triazinyl, 1,2,3-triazinyl, tetrazolyl, 1,2,4,5-tetrazinyl, 1,2,3,4-tetrazinyl, 1,2,3,5-tetrazinyl, purinyl, pteridinyl, indolizinyl and benzothiadiazolyl or groups derived from a combination of these systems.

The aryloxy, the arylboryl, the arylphosphoryl, and the aryloxyphosphinyl in the present invention refer to a monovalent functional group in which aryl having 6 to 60 carbon atoms is bonded to an oxygen atom, a boron atom, a phosphorus atom, oxyphosphinyl, and a nitrogen atom. As non-limiting examples, there are phenoxy, naphthoxy, diphenoxy, diphenylboryl, diphenylphosphoryl, diphenyloxyphosphinyl, diphenylamino, and the like.

The alkylsilyl in the present invention means silyl substituted with an alkyl having 1 to 40 carbon atoms, the arylsilyl means silyl substituted with an aryl having 6 to 60 carbon atoms, and the arylamino means an amine substituted with an aryl having 6 to 60 carbon atoms.

The arylene and the heteroarylene in the present invention mean a divalent functional group obtained by removing a hydrogen atom from the aryl having 6 to 60 carbon atoms or the heteroaryl having 2 to 60 carbon atoms. In such a case, as non-limiting examples thereof, there are phenylene, naphthylene, biphenylene, pyridylidene, and the like.

A second object of the present invention provides an organic electroluminescent material comprising the organic compound.

A third object of the present invention provides an organic electroluminescent element, comprising a first electrode, a second electrode, and one or more organic layers arranged between the first electrode and the second electrode. The organic layer comprises the organic compound.

The organic electroluminescent element comprises a cathode, an anode, and at least one emission layer. In addition to these layers, the element may further comprise other layers, for example, in each case, it may comprise one or more hole injection layers, hole transport layers, hole blocking layers, electron transport layers, electron injection layers, exciton blocking layers, electron blocking layers and/or charge generation layers. The organic layer containing the compound shown in the formula I is preferably an emission layer, an electron transport layer, and an electron transport auxiliary layer further stacked on the electron transport layer. In such a case, the compound shown in the formula I may be used as a host substance of the emission layer or a substance of an electron transport layer and an electron transport auxiliary layer. However, it should be noted that the presence of all these layers is not necessary. The organic electroluminescent element here may comprise one emission layer, or may comprise a plurality of emission layers. That is a plurality of luminescent compounds capable of emitting light are used in the emission layer. A system having three emission layers is particularly preferred, wherein the three layers respectively emit a blue light, a green light, and a red light. If more than one emission layer is present, at least one of these layers comprises the compounds of the present invention according to the present invention.

The present invention provides an organic electroluminescent element comprising the compound shown in the formula (I). Specifically, the organic electroluminescent element according to the present invention comprises a first electrode, a second electrode, and one or more organic layer arranged between the first electrode and the second electrode. In the one or more organic layer, at least one layer comprises the compound shown in the formula I. In such a case, the compound may be used alone or in combination of two or more. The one or more organic layers may be any one or more of a hole injection layer, a hole transport layer, an emission layer, an electron transport layer, and an electron injection layer. Preferably, the organic layer comprising the compound of the chemical formula I may be an emission layer, an electron transport layer, and an electron auxiliary layer, more preferably, an electron transport layer and an electron transport auxiliary layer.

The emission layer of the organic electroluminescent element according to the present invention may contain a host material. In such a case, the host material may comprise the compound of the formula (I). When such emission layer contains the compound shown in the formula (I), the hole transport ability increases, and the chance of combining a hole and an electron in the emission layer increases, such that an organic electroluminescent element having an excellent efficiency, service life, luminance, and driving voltage may be provided. In addition, the emission layer of the organic electroluminescent element of the present invention may comprise a compound other than the compound shown in the formula (I) as a host.

The electron transport layer of the organic electroluminescent element of the present invention may comprise an electron transport material. In such a case, the electron transport layer may comprise the compound shown in the formula (I). When the electron transport layer comprises the compound shown in the formula (I), the electron transport ability is enhanced by two electron-withdrawing groups, and the injected electrons may be smoothly transported to the emission layer, such that an organic electroluminescent element having an excellent efficiency, service life, luminance, and driving voltage may be provided. The electron transport auxiliary layer may be further stacked on the electron transport layer. In the case where the compound shown in the formula I is comprised in the transport auxiliary layer, the efficiency, service life, driving voltage, etc., of a blue organic electroluminescent element may be improved particularly due to an effect of preventing transition of an exciton from the emission layer and the electron transport layer by a high triplet energy level.

The structure of the organic electroluminescent element of the present invention is not particularly limited. As non-limiting examples, as shown in FIG. 1 and FIG. 2, the structure may comprises a substrate, an anode, a hole injection layer, a hole transport layer, an electron blocking layer, an emission layer, an electron transport layer, and a cathode sequentially stacked. An electron injection layer may be further stacked on the electron transport layer and a hole blocking layer may be further stacked on the emission layer. In addition, the organic electroluminescent element of the present invention may be of a structure with an insulating layer or an adhesive layer inserted between the electrode and an organic layer.

In the description of the present invention, unless otherwise specified, "a plurality of" means two or more. The terms "upper", "lower", etc., indicate the orientation or position relationships based on the orientations or position relationships shown in the drawings and are intended to facilitate the description of the present invention and simplify the description only, rather than indicate or imply that a device or element referred to must have a particular orientation or be constructed and operated in a particular orientation, and hence cannot be construed as limiting the present invention.

Further, the organic layer is an emission layer, an electron transport layer, an electron injection layer, an electron transport auxiliary layer or an electron blocking layer.

Further, the organic compound is a host substance of the emission layer.

The organic electroluminescent element of the present invention does not comprise an individual hole injection layer and/or a hole transport layer and/or a hole blocking layer and/or an electron transport layer and/or an electron injection layer, i.e., the case where the emission layer is directly adjacent to the hole injection layer or the anode, and/or the emission layer is directly adjacent to the electron transport layer or the electron injection layer or the cathode.

In the other layers of the organic electroluminescent device of the present invention, particularly in the hole injection layer and the hole transport layer, and the electron injection layer and the electron transport layer, all materials may be used in a manner generally used according to the prior art. A person of ordinary skill in the art will therefore be able to use all materials known for organic electroluminescent elements in combination with the emission layer according to the present invention without involving any inventive effort.

Furthermore, preference is given to the following organic electroluminescent device characterized in that one or more layers are applied by means of a sublimation method, wherein the material is applied by means of vapor deposition in a vacuum sublimation device at an initial pressure below $10^{-5}$ Pa, preferably below $10^{-6}$ Pa. However, the initial pressure may also be even lower, for example below $10^{-7}$ Pa.

Likewise, preference is given to the following organic electroluminescent device in which one or more layers are applied by means of an organic vapor deposition method or by means of carrier gas sublimation, wherein the material is applied at a pressure between $10^{-5}$ Pa and 1 Pa. A particular example of the method is an organic vapor jet printing method, in which the material is applied directly through a nozzle and is therefore structured.

Furthermore, preference is given to the following organic electroluminescent device in which one or more layers are produced from a solution by means of, for example, spin coating, or by means of any desired printing method such as screen printing, flexography, lithography, photo-initiated thermal imaging, heat transfer printing, inkjet printing, or nozzle printing. Soluble compounds are obtained, for example, by means of appropriate substitution. These methods are also particularly suitable for oligomers, dendrimers and polymers. In addition, a hybrid method is feasible, in which for example one or more layers are applied from a solution and one or more additional layers are applied by means of vapor deposition.

These methods are generally known to a person of ordinary skill in the art, and they may be applied to an organic electroluminescent element containing the compound according to the present invention without involving any inventive effort.

Therefore, the present invention also relates to a method for manufacturing the organic electroluminescent device according to the present invention, in which at least one layer is applied by means of a sublimation method, and/or characterized in that at least one layer is applied by means of an organic vapor deposition method or carrier gas sublimation, and/or characterized in that at least one layer is applied from a solution by means of spin coating or by means of a printing method.

In addition, the present invention relates to a compound comprising at least one of the present invention as indicated above. The same preference as indicated above for the organic electroluminescent element applies to the compound of the present invention. Particular, the compound may further preferably comprise other compounds. The compound according to the present invention is processed from a liquid phase, for example, by spin coating or a printing method, requiring a preparation of a compound according to the present invention. These preparations may be, for example, a solution, a dispersion, or an emulsion. For this purpose, a mixture of two or more solvents may be preferably used. Suitable and preferred solvents are, for example, toluene, anisole, o-xylene, m-xylene or p-xylene, methyl benzoate, mesitylene, tetralin, o-dimethoxybenzene, tetrahydrofuran, methyl tetrahydrofuran, tetrahydropyran, chlorobenzene, dioxane, phenoxytoluene, especially 3-phenoxytoluene, (−)-fenchone, 1,2,3,5-tetramethylbenzene, 1,2,4,5- tetramethylbenzene, 1-methylnaphthalene, 2-methylbenzothiazole, 2-phenoxyethanol, 2-pyrrolidone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indan, methyl benzoate, 1-methylpyrrolidone, p-methylisopropylbenzene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, or a mixture of these solvents.

In addition, the raw materials used in the present invention are commercially available unless otherwise specified. Any range disclosed in the invention includes end values and any value between the end values, or any subrange constituted by end values or any value between the endpoints.

Compared with the prior art, the beneficial effects of the present invention are:
when used for preparing an organic electroluminescent element, the organic compound of the present invention results in an excellent electron mobility, thermal stability, and luminescent property. The organic compound may be used in an organic layer of the organic electroluminescent element. The organic compound of the present invention has a relatively good film-forming property. When the organic compound is used in an electron transport layer and an electron transport auxiliary layer, an organic electroluminescent element with a lower driving voltage, a higher luminous efficiency, and a longer service life compared to a previous electron transport material may be manufactured, and moreover, a full-color display panel with an improved performance and service life may be further manufactured.

BRIEF DESCRIPTION OF THE DRAWINGS

In order to describe the technical solutions in examples of the present invention or the prior art more clearly, the drawings which need to be used in the description of the examples or the prior art will be simply introduced below. Obviously, the accompanying drawings in the following description show merely some examples of the present invention, and those of ordinary skill in the art may still derive other drawings according to these drawings without creative efforts.

LIST OF REFERENCE NUMERALS

Figure 1:
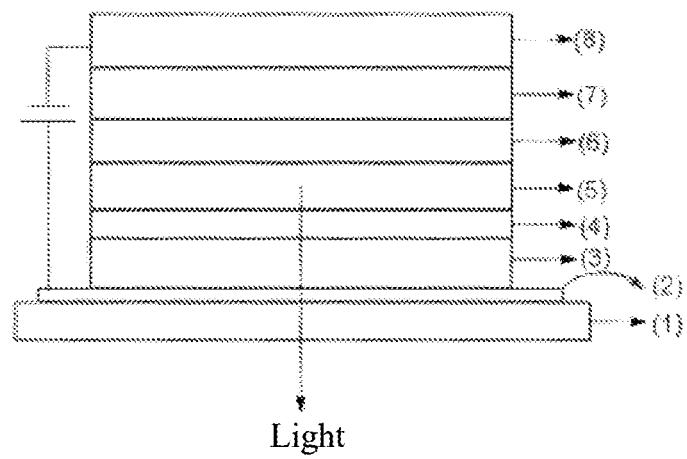
FIG. 1 is a schematic diagram of a bottom light emission example of an organic electroluminescent device of the present invention.
Figure 2:
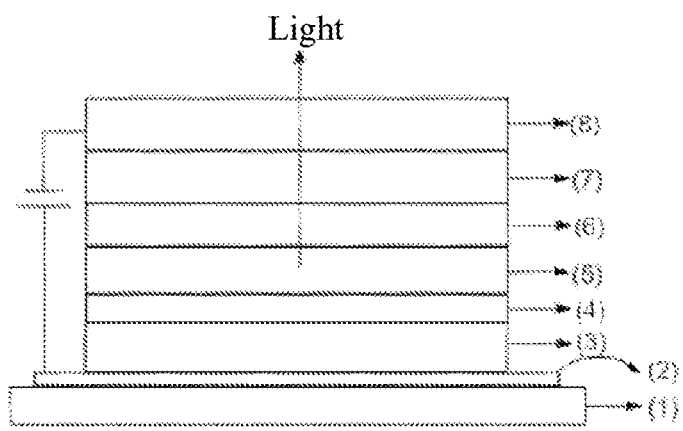
FIG. 2 is a schematic diagram of a top light emission example of an organic electroluminescent device of the present invention.

1—substrate, 2—anode, 3—hole injection layer, 4—hole transport layer/electron blocking layer, 5—emission layer, 6—hole blocking/electron transport layer, 7—electron injection layer, and 8—cathode.

DETAILED DESCRIPTION OF EMBODIMENTS

To make the objects, technical solutions, and advantages of the present invention clearer, the following describes in detail the technical solutions of the present invention. Apparently, the described examples are merely some rather than all of the examples of the present invention. All other embodiments obtained by a person of ordinary skill in the art based on the examples of the present invention without creative efforts should fall within the protection scope of the present invention.

A test instrument and method for testing performances of OLED materials and devices in the following examples are as follows:

Performance testing conditions for OLED:

Luminance and chromaticity coordinates: tested using a spectrum scanner PhotoResearch PR-715;

Current density and lighting voltage: tested using digital source meter Keithley 2420;

Power efficiency: tested using NEWPORT 1931-C.

Example 1

The method for preparing a compound of CJHP07 comprises the following steps:

Step 1: Preparation of Intermediate Int-1

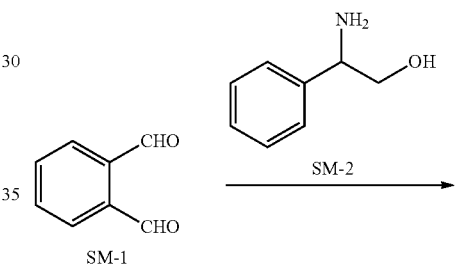

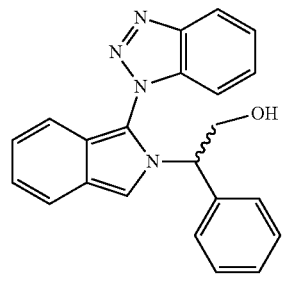

Int-1

50 mL of dichloromethane and 10.0 g of a 4 Å molecular sieve are added into 10.0 mmol of o-phthalaldehyde, 10.0 mmol of phenylglycinol, and 20.0 mmol of benzotriazole, the mixture is stirred and reacted at room temperature for 10 hours, the reaction solution is filtered, the filtrate is washed with 2 mol/L of an aqueous sodium hydroxide solution and a saturated salt solution, an organic phase is collected, dried, and filtered, the filtrate is concentrated under a reduced pressure to dryness, and the residue is separated and purified by a silica gel column to obtain a dark brown solid Int-1 with a yield of 59%.

Step 2: Preparation of Intermediate Int-2

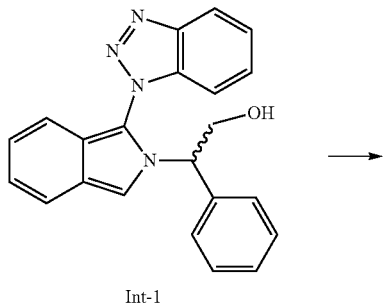

Int-1

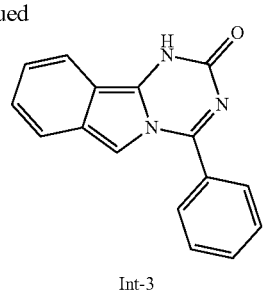

Int-3

10.0 mmol of the intermediate Int-2 is mixed with 35.0 g of urea, the mixture is heated to 150° C., and stirred and reacted for 2 hours, when the reaction solution is cooled to 80° C., 100 mL of a 10% sodium hydroxide aqueous solution is added, the mixture is stirred for 30 minutes and filtered, and the filter cake is washed with water to obtain a yellow solid Int-3 with a yield of 83%.

Step 4: Preparation of Intermediate Int-4

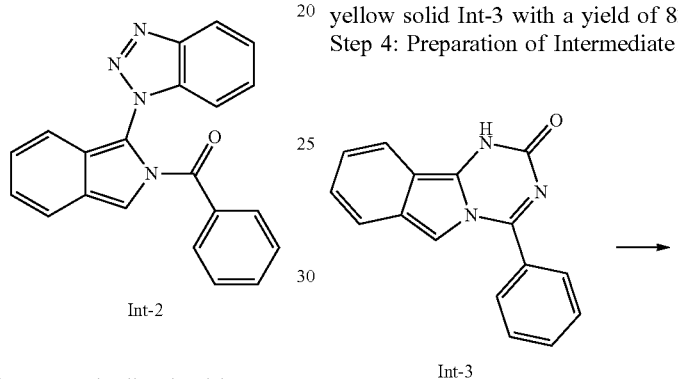

Int-3

Int-4

15.0 mmol of the intermediate Int-1 is dissolved in 100 mL of methanol, 0.1 mol of ammonium formate and 0.1 g of palladium/carbon are added, the mixture is stirred and reacted for 8 hours at room temperature, the obtained product is filtered, the filtrate is concentrated under a reduced pressure to dryness, 100 mL of dichloromethane is added for dissolution, the mixture is washed twice with water, an organic phase is collected, dried, and filtered, 2.5 g of triethylamine is added into the filtrate, 16.5 mmol of benzoyl chloride is slowly dropwise added, the mixture is stirred and reacted for 2 hours, 20 mL of a 10% sodium hydroxide aqueous solution is added, an organic phase is separated and then washed with a saturated salt solution and water, the organic phase is dried, filtered, and concentrated under a reduced pressure to dryness, and the residue is separated and purified by a silica gel column to obtain a yellow solid Int-2 with a yield of 78%.

Step 3: Preparation of Intermediate Int-3

10.0 mmol of the intermediate Int-3 is dissolved in 40 mL of phosphorus oxychloride, heated to reflux, and stirred and reacted for 8 hours, the reaction solution is cooled to room temperature, poured into 200 mL of ice/water, and filtered, and the filter cake is washed with water, and separated and purified by a silica gel column to obtain a yellow solid Int-4 with a yield of 76%.

Step 5: Preparation of Intermediate Int-5

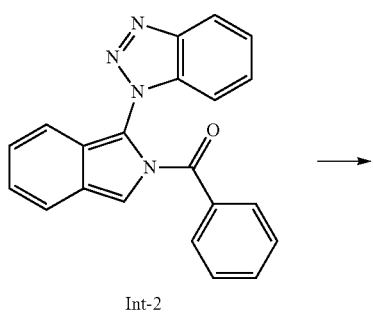

Int-2

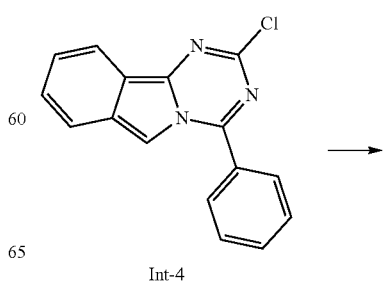

Int-4

Step 7: Preparation of Compound CJHP07

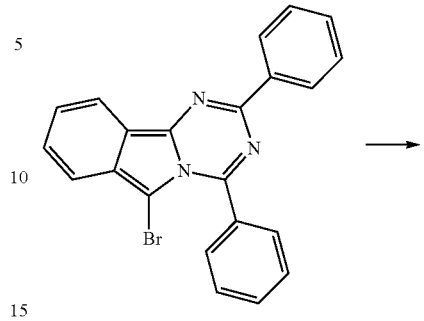

Int-6

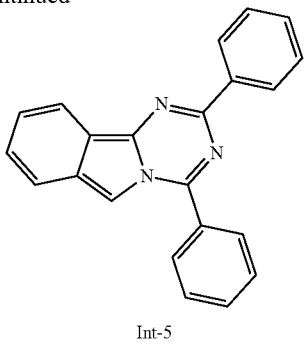

Int-5

40 mL of toluene, 10 mL of ethanol, and 5 mL of water are added into 9.5 mmol of phenylboronic acid, 8.6 mmol of the intermediate Int-4, 3.7 g (34.9 mmol) of sodium carbonate, and 5 mg of a Pd(PPh$_3$)$_4$ catalyst, the mixture is heated, refluxed, stirred, and reacted for 12 hours, the reaction solution is cooled to room temperature and extracted with ethyl acetate, the organic phase is dried and filtered, the filtrate is concentrated under reduced pressure to dryness, and the residue is separated and purified by a silica gel column to obtain a yellow solid Int-5 with a yield of 84%.

Step 6: Preparation of Intermediate Int-6

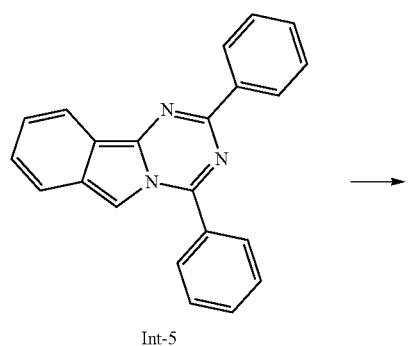

Int-5

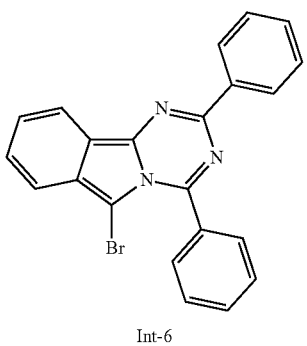

Int-6

10.0 mmol of the intermediate Int-5 is dissolved in 80 mL of dichloromethane, the mixture is cooled to 10° C. with an ice water bath, 11.0 mmol of NBS is added in batches, the mixture is stirred and reacted for 2 hours, 80 mL of water is added, the organic phase is separated out, dried, and filtered, the filtrate is concentrated under reduced pressure to dryness, and the residue is separated and purified by a silica gel column to obtain a yellow solid Int-6 with a yield of 96%.

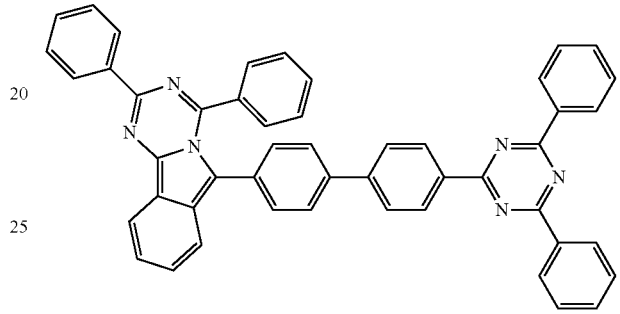

CJHP07

40 mL of toluene, 10 mL of ethanol, and 10 mL of water are added into 10.2 mmol of (4'-(4,6-diphenyl-1,3,5-triazin-2-yl)-[1,1'-biphenyl]-4-yl)boronic acid, 8.5 mmol of the intermediate Int-6, 3.6 g (34.0 mmol) of sodium carbonate, and 5 mg of a Pd(PPh$_3$)$_4$ catalyst, the mixture is heated, refluxed, stirred, and reacted for 12 hours, the reaction solution is cooled to room temperature and extracted with ethyl acetate, the organic phase is dried and filtered, the filtrate is concentrated under reduced pressure to dryness, the residue is purified by a silica gel column, and the obtained product is heated to boiling with ethanol and filtered while hot to obtain 4.9 g of a product CJHPO7 with a yield of 82.4%.

MS(MALDI-TOF): m/z 705.2782[M+H]+; 1HNMR (δ, CDCl3): 8.77-8.75 (4H, m); 8.51-8.48 (7H, m); 8.03-8.01 (4H, m); 7.92-7.90 (2H, m); 7.72-7.70 (3H, m); 7.56-7.45 (10H, m); and 7.38-7.35 (2H, m).

Example 2

Preparations of compounds CJHP01-CJHP06, CJHP08-CJHP48, and CJHP103-CJHP107 refer to the synthesis method of the compound CJHP07 in example 1. The differences lie in that the (4'-(4,6-diphenyl-1,3,5-triazin-2-yl)-[1,1'-biphenyl]-4-yl)boronic acid in step 7 of example 1 is replaced with different compounds according to actual needs, the mass amounts of the compounds are changed according to molar weights, and other experimental parameters are adjusted according to actual needs.

Example 3

The method for preparing a compound CJHP63 comprises the following steps:

Step 1: Preparation of Intermediate Int-7

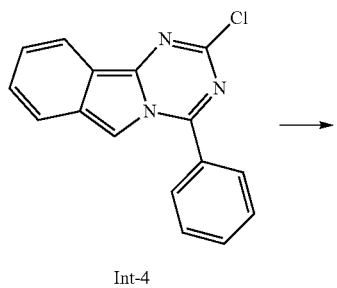

Int-4

10.0 mmol of the intermediate Int-4 prepared in step 4 of example 1 is dissolved in 80 mL of dichloromethane, the mixture is cooled to 0° C. with an ice water bath, 11.0 mmol of NBS is added in batches, the mixture is stirred and reacted for 2 hours, 80 mL of water is added, the organic phase is separated out, dried, and filtered, the filtrate is concentrated under reduced pressure to dryness, and the residue is separated and purified by a silica gel column to obtain a yellow solid Int-7 with a yield of 94%.

Step 2: Preparation of Intermediate Int-8

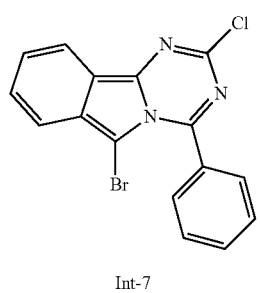

Int-7

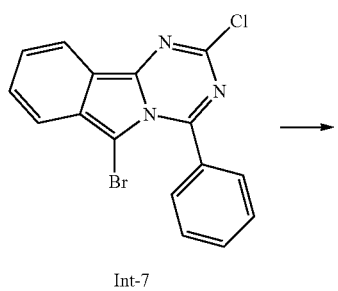

Int-7

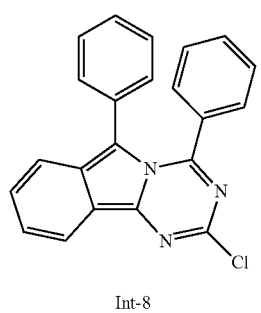

Int-8

50 mL of toluene, 20 mL of ethanol, and 20 mL of water are added into 11.0 mmol of phenylboronic acid, 10.0 mmol of the intermediate Int-7, 2.4 g (22.0 mmol) of sodium carbonate, and 5 mg of a Pd(PPh$_3$)$_4$ catalyst, the mixture is heated, refluxed, stirred, and reacted for 12 hours, the reaction solution is cooled to room temperature and extracted with ethyl acetate, the organic phase is dried and filtered, the filtrate is concentrated under reduced pressure to dryness, and the residue is separated and purified by a silica gel column to obtain a yellow solid Int-8 with a yield of 75%.

Step 3: Preparation of Compound CJHP63

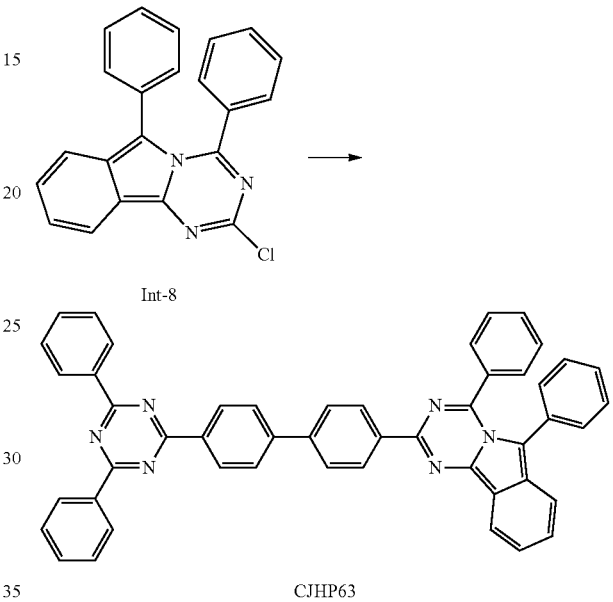

Int-8

CJHP63

40 mL of toluene, 10 mL of ethanol, and 5 mL of water are added into 9.5 mmol of (4'-(4,6-diphenyl-1,3,5-triazin-2-yl)-[1,1'-biphenyl]-4-yl)boronic acid, 8.6 mmol of the intermediate Int-8, 3.7 g (34.9 mmol) of sodium carbonate, and 5 mg of a Pd(PPh$_3$)$_4$ catalyst, the mixture is heated, refluxed, stirred, and reacted for 12 hours, the reaction solution is cooled to room temperature and extracted with ethyl acetate, the organic phase is dried and filtered, the filtrate is concentrated under reduced pressure to dryness, the residue is purified by a silica gel column, and the obtained product is heated to boiling with ethanol and filtered while hot to obtain 4.4 g of a product CJHP63 with a yield of 72.5%.

MS(MALDI-TOF): m/z 705.2786[M+H]+; 1HNMR (δ, CDCl3): 8.82-8.80 (4H, m); 8.51-8.48 (5H, m); 8.37-8.35 (2H, m); 7.92-7.88 (6H, m); 7.73-7.68 (5H, m); 7.53-7.45 (8H, m); and 7.36-7.34 (2H, m).

Example 4

Preparation methods of compounds CJHP49-CJHP62, and CJHP64-CJHP102 are the same as the preparation method of the compound CJHP6 in example 3. The differences lie in that the (4'-(4,6-diphenyl-1,3,5-triazin-2-yl)-[1,1'-biphenyl]-4-yl)boronic acid in step 3 of example 3 is replaced with different compounds according to actual needs, the mass amounts of the compounds are changed according to molar weights, and other experimental parameters are adjusted according to actual needs.

Example 5

The method for preparing a compound CJHP133 comprises the following steps:

Step 1: Preparation of Intermediate Int-11

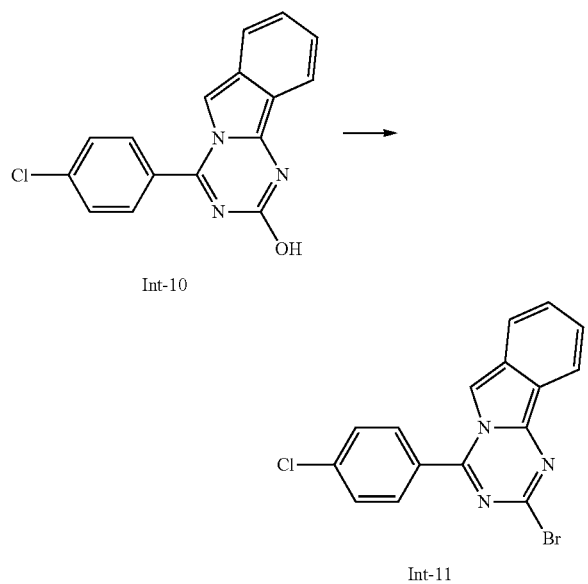

11.0 mmol of phosphorus pentabromide, 10.0 mmol of an intermediate Int-10 (obtained by only replacing benzoyl chloride with p-chlorobenzoyl chloride in step 2 referring to step 1 to step 3 of example 1), and 60 mL of toluene are heated, refluxed, stirred, and reacted for 6 hours, the reaction solution is cooled to room temperature and concentrated under reduced pressure to dryness, crushed ice is added to the residue, the residue is stirred and filtered, and the filter cake is washed with water to obtain an intermediate Int-11 as a yellow solid with a yield of 85%.

Step 2: Preparation of Intermediate Int-12

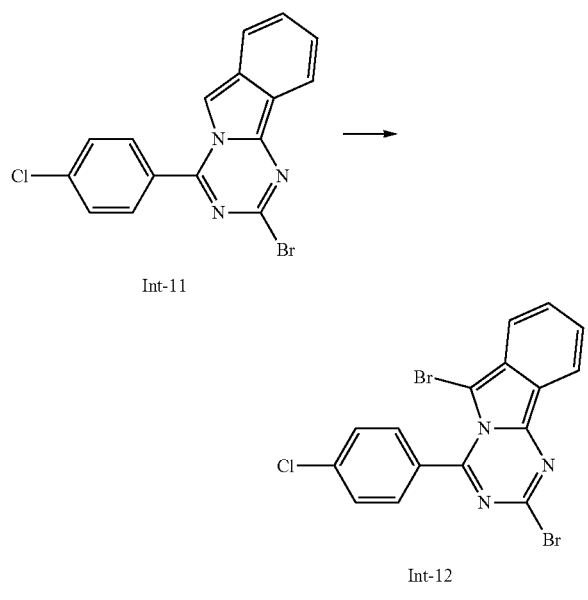

10.0 mmol of the intermediate Int-11 is dissolved in 100 mL of dichloromethane, 11.0 mmol of NBS is added in batches, the mixture is stirred and reacted for 5 hours, 80 mL of water is added, the organic phase is separated out, dried, and filtered, the filtrate is concentrated under reduced pressure to dryness, and the residue is separated and purified by a silica gel column to obtain a yellow solid Int-12 with a yield of 93%.

Step 3: Preparation of Intermediate Int-13

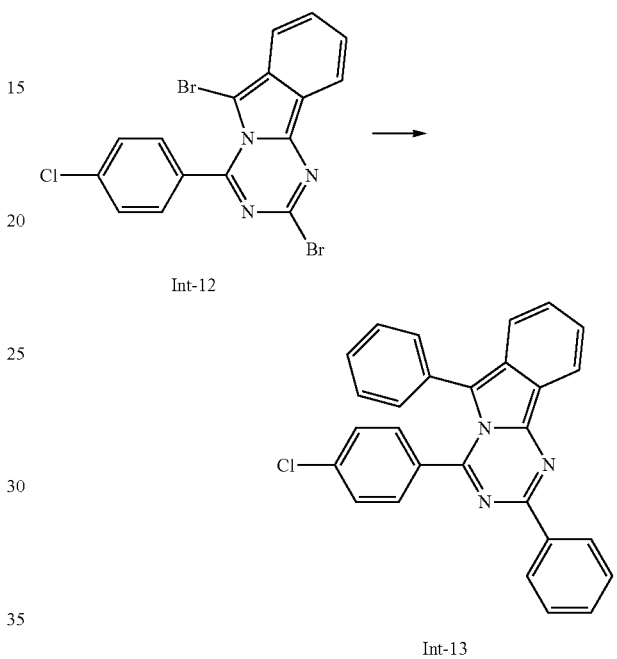

80 mL of toluene, 40 mL of ethanol, and 40 mL of water are added into 17.6 mmol of phenylboronic acid, 8.0 mmol of the intermediate Int-12, 3.8 g (36.0 mmol) of sodium carbonate, and 138.6 mg of a Pd(PPh$_3$)$_4$ catalyst, the mixture is heated, refluxed, stirred, and reacted for 12 hours, the reaction solution is cooled to room temperature, 20 mL of water is added for dilution, the solution is extracted with ethyl acetate, the organic phase is dried and filtered, the filtrate is concentrated under reduced pressure to dryness, and the residue is separated and purified by a silica gel column to obtain a compound Int-13 with a yield of 79%.

Step 4: Preparation of Compound CJHP133

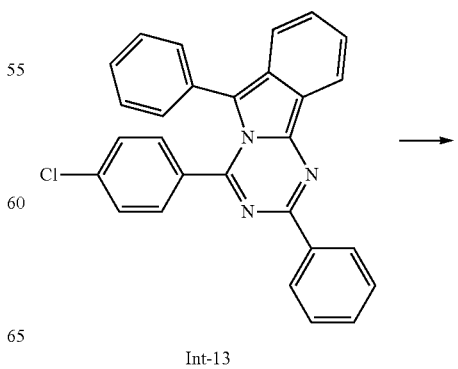

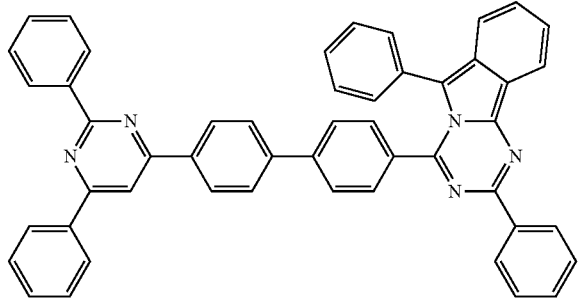

CJHP133

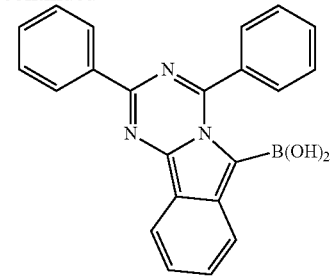

Int-14

80 mL of toluene, 40 mL of ethanol, and 40 mL of water are added into 9.6 mmol of (4-(2,6-diphenylpyrimidin-4-yl) phenyl)boronic acid, 8.0 mmol of the intermediate Int-13, 5.5 g (16.0 mmol) of potassium phosphate hydrate, and 185.0 mg of a Pd(PPh$_3$)$_4$ catalyst, the mixture is heated, refluxed, stirred, and reacted for 12 hours, the reaction solution is cooled to room temperature, 20 mL of water is added for dilution, the solution is extracted with ethyl acetate, the organic phase is dried and filtered, the filtrate is concentrated under reduced pressure to dryness, and the residue is separated and purified by a silica gel column to obtain a compound CJHIP133 with a yield of 83%.

MS(MALDI-TOF): m/z 704.2832[M+H]+; 1HNMR (δ, CDCl3): 8.33-8.26 (7H, m); 8.24-8.20 (4H, m); 8.03-8.02 (2H, m); 7.94-7.90 (2H, m); 7.76-7.65 (9H, m); and 7.57-7.32 (18H, m).

Example 6

Preparations of compounds CJHP108-CJHP132, and CJHP134-CJHP163 are the same as the method of the compound CJHP133 in example 5. The differences lie in that the (4-(2,6-diphenylpyrimidine-4-yl)phenyl)boronic acid in step 4 of example 5 is replaced with different compounds according to actual needs, the mass amounts of the compounds are changed according to molar weights, and other experimental parameters are adjusted according to actual needs.

Example 7

A preparation of a compound CJHP167 comprises the following steps:
Step 1: Preparation of Intermediate Int-14

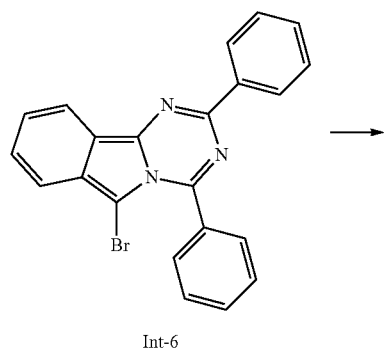

Int-6

Under the protection of nitrogen, 15.0 mmol of an intermediate Int-6 is dissolved in 80 mL of dry tetrahydrofuran, cooled with liquid nitrogen to −80° C., 7.2 mL of 2.5 M n-butyllithium n-hexane solution is added dropwise, the solution is stirred and reacted for 30 minutes, 20.0 mmol of a trimethyl borate solution is added dropwise and dissolved in an anhydrous tetrahydrofuran solution, the solution is stirred and reacted for 1 hour, the reaction solution is heated to room temperature, 20 mL of 2 N dilute hydrochloric acid is added, the solution is stirred and reacted for 1 hour, and extracted with ethyl acetate, the organic phase is collected, dried, and filtered, the filtrate is concentrated under reduced pressure to dryness, petroleum ether is added for dispersion, and the solution is filtered to obtain an intermediate Int-14 with a yield of 80%.

Step 2: Preparation of Compound CJHP167

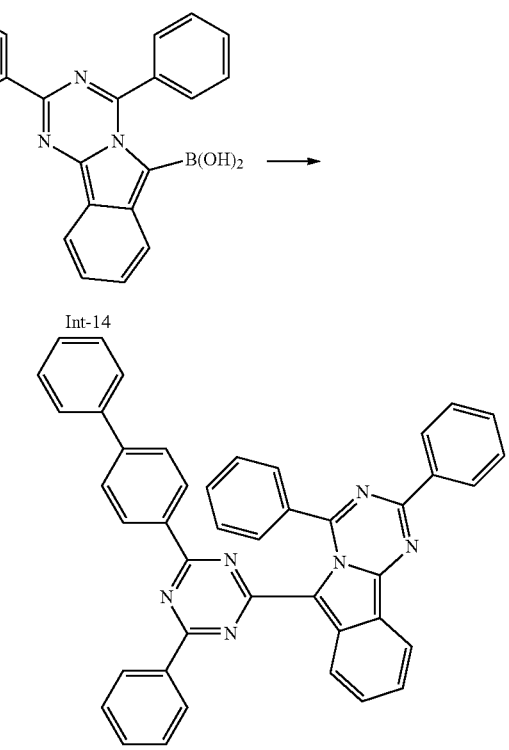

CJHP167

40 mL of toluene, 10 mL of ethanol, and 10 mL of water are added into 10.0 mmol of 2-([1,1'-biphenyl]-4-yl)-4-chloro-6-phenyl-1,3,5-triazine, 12.0 mmol of the intermediate Int-14, 3.2 g (30.0 mmol) of sodium carbonate, and 11.5 mg of a Pd(PPh3)4 catalyst, the mixture is heated, refluxed, stirred, and reacted for 12 hours, the reaction solution is cooled to room temperature and extracted with ethyl acetate, the organic phase is dried and filtered, the filtrate is concentrated under reduced pressure to dryness, the residue is purified by a silica gel column and recrystallized with dichloromethane-ethanol to obtain a product CJIP167 with a yield of 76%.

MS(MALDI-TOF): m/z 629.2472[M+H]+; 1HNMR (δ, CDCl3): 8.84-8.82 (2H, d); 8.62-8.59 (3H, m); 8.43-8.41 (4H, m); 7.92-7.89 (3H, m); 7.72-7.69 (2H, m); 7.58-7.52 (6H, m); and 7.42-7.23 (8H, m).

Example 8

Preparations of compounds CJHP164-CJHP166, and CJHP168-CJHP173 are the same as the preparation method of the compound CJHP167 in example 7. The differences lie in that the 2-([1,1'-biphenyl]-4-yl)-4-chloro-6-phenyl-1,3,5-triazine in step 2 of example 7 is replaced with different compounds according to actual needs, the mass amounts of the compounds are changed according to molar weights, and other experimental parameters are adjusted according to actual needs.

Example 9

Preparation of Compound CJHP176($T_3$=O):

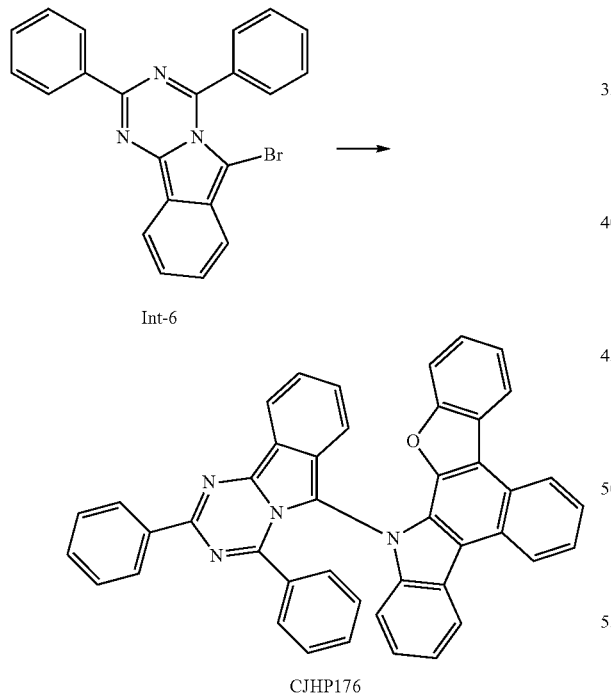

CJHP176

Under the protection of nitrogen, 60 mL of dried toluene is added into 11.0 mmol of the intermediate Int-6, 10.0 mmol of benzo[c]benzofuran[2,3-a]carbazole, 1.5 g of sodium tert-butoxide, 0.21 g of cuprous iodide, 0.7 mg of $Pd_2(dba)_3$ $CHCl_3$, and 0.1 mL of 10% tri-tert-butylphosphine toluene solution, the mixture is heated to 100° C., stirred, and reacted for 12 hours, the reaction solution is cooled to room temperature, 20 mL of water is added for dilution, the solution is extracted with ethyl acetate, the organic phase is dried and filtered, the filtrate is concentrated under reduced pressure to dryness, and the residue is separated and purified by a silica gel column and recrystallized with dichloromethane-tetrahydrofuran to obtain a product CJHP176 with a yield of 86%.

MS(MALDI-TOF): m/z 627.2171[M+H]+; 1HNMR (δ, CDCl3): 8.59-8.57 (2H, d); 8.52-8.45 (6H, m); 8.30-8.28 (3H, m); 7.89-7.88 (1H, m); 7.74-7.72 (2H, m); 7.64-7.58 (4H, m); 7.56-7.54 (3H, m); 7.52-7.47 (3H, m); 7.42-7.39 (1H, m); and 7.35-7.33 (1H, m).

Example 10

Preparations of compounds CJHP174, CJHP175, CJHP177-CJHP189, and CJHP209-CJHP243 are the same as the preparation method of the compound CJHP176 in example 9. The differences lie in that the intermediate Int-6 and benzo[c]benzofuran[2,3-a]carbazole in example 9 are replaced with different compounds according to actual needs, the mass amounts of the compounds are changed according to molar weights, and other experimental parameters are adjusted according to actual needs.

Example 11

Preparation of Compound CJHP204:

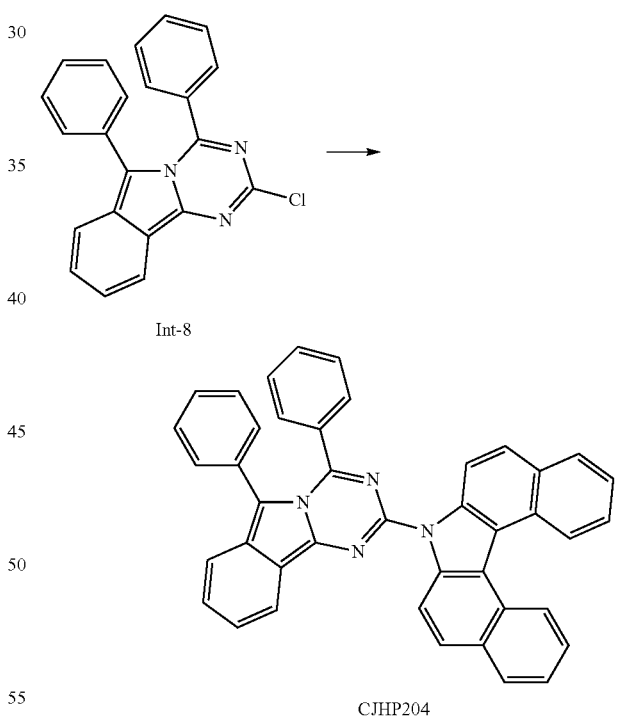

CJHP204

Under the protection of nitrogen, 10.0 mmol of dibenzo[c,g]carbazole is dissolved in 60 mL of N,N-dimethylformamide, the mixture is cooled to 0° C. with an ice water bath, 11.0 mmol of a 65% sodium hydride oil dispersion solid is added in batches, the mixture is stirred and reacted for 1 hour, 12.0 mmol of an intermediate Int-8 solid is added, the mixture is stirred and reacted for 2 hours, the reaction solution is heated to room temperature, stirred, and reacted for 12 hours, the reaction solution is poured into 200 mL of ice water and filtered, and the filter cake is washed with water, and separated and purified by a silica gel column to obtain a product CJHP204 with a yield of 87%.

MS(MALDI-TOF): m/z 587.2251[M+H]+; 1HNMR (δ, CDCl3): 8.49-8.46 (5H, m); 8.15-8.13 (4H, d); 7.98-7.97 (2H, m); 7.92-7.90 (2H, m); 7.68-7.59 (9H, m); 7.48-7.44 (2H, m); and 7.35-7.33 (2H, m).

Example 12

Preparations of compounds CJHP190-CJHP203, and CJHP205-CJHP208 are the same as the preparation method of the compound CJHP204 in example 11. The differences lie in that the dibenzo[c,g]carbazole in example 11 is replaced with different compounds according to actual needs, the mass amounts of the compounds are changed according to molar weights, and other experimental parameters are adjusted according to actual needs.

Example 13

Preparation of compound CJHP244:

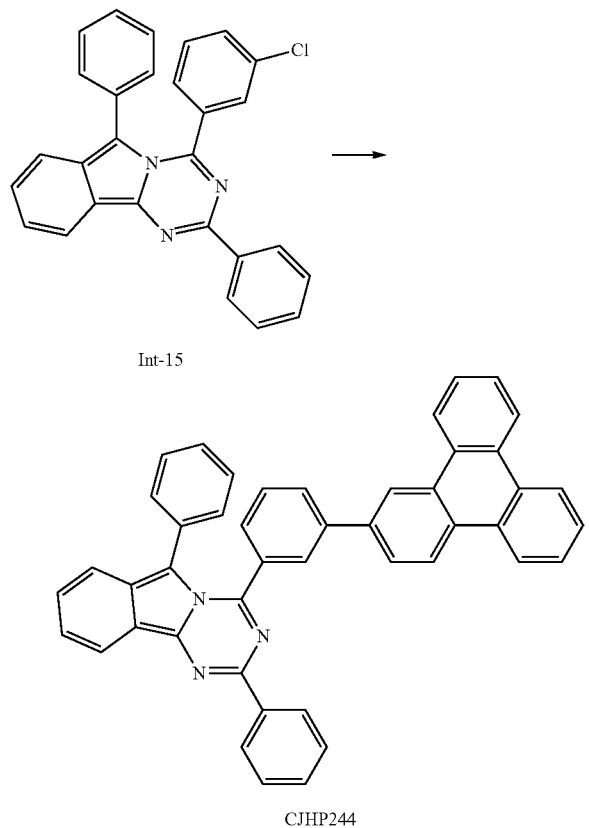

60 mL of toluene, 30 mL of ethanol, and 20 mL of water are added into 9.6 mmol of 2-benzophenanthryl boric acid, 8.0 mmol of the intermediate Int-15 (prepared referring to the synthesis method from step 1 to step 3 in example 5), 2.2 g (20.0 mmol) of sodium carbonate, and 92.4 mg of a Pd(PPh$_3$)$_4$ catalyst, the mixture is heated, refluxed, stirred, and reacted for 12 hours, the reaction solution is cooled to room temperature, 20 mL of water is added for dilution, the solution is extracted with dichloromethane, the organic phase is dried and filtered, the filtrate is concentrated under reduced pressure to dryness, and the residue is separated and purified by a silica gel column to obtain a compound CJHP244 with a yield of 78%.

MS(MALDI-TOF): m/z 624.2425[M+H]+; 1HNMR (δ, CDCl3): 9.21 (1H, s); 8.75-8.69 (4H, m); 8.35-8.31 (5H, m); 8.26-8.25 (1H, d); 7.96-7.95 (1H, d); 7.83-7.79 (3H, m); 7.70-7.63 (7H, m); 7.59-7.55 (3H, m); 7.51-7.48 (2H, m); and 7.44-7.38 (2H, m).

Example 14

Preparations of compounds CJHP245-CJHP252 are the same as the preparation method of the compound CJHP244 in example 13. The differences lie in that the 2-benzophenanthryl boric acid in example 13 is replaced with different compounds according to actual needs, the mass amounts of the compounds are changed according to molar weights, and other experimental parameters are adjusted according to actual needs.

Test Example 1

The compounds prepared in examples 1-14 are refined by sublimation to prepare an organic electroluminescent element. A specific preparation method is as follows:
(1) an ITO-coated glass substrate is ultrasonically washed with distilled water, ultrasonically washed with an isopropanol and an acetone/ethanol mixed solvent, baked in a clean environment to be completely dried, irradiated with an ultraviolet light cleaning machine for 10 minutes, cleaned by UV for 5 minutes, and transferred to a vacuum evaporation machine.
(2) the treated ITO electrode is sequentially stacked with HT002 (BaYi Space, 300 Å)/HT022 (BaYi Space, 2100 Å)/HT001 (BaYi Space, 100 Å)/AND+5% DA021 (BaYi Space, 300 Å)/each of compounds CJHPO1-CJHP252 (300 Å)/LiF(10 Å)/Al(1500 Å) to manufacture an organic electroluminescent element.

Comparative Example 1

Except that as an electron transport layer substance, Alq3(8-hydroxyquinoline aluminum) is used to replace compounds CJHPO1-CJHP252, the operation is the same as that in test example 1 to prepare an organic electroluminescent element.

Comparative Example 2

Except that as an electron transport layer substance, compounds CJHPO1-CJHP252 are not used, the operation is the same as that in test example 1 to prepare an organic electroluminescent element.

Structural formulas of AND and Alq3 are as shown below.

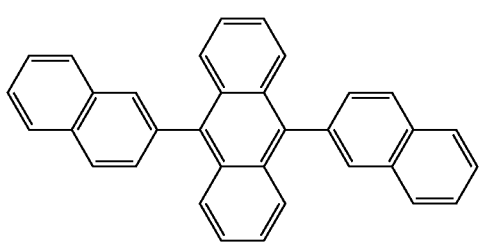

ADN

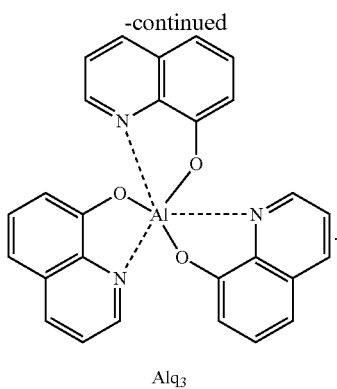

Alq3

The driving voltage, current efficiency, and luminescent peak of the organic electroluminescent elements prepared in test example 1 and comparative examples 1-2 are measured when a current density is 10 mA/cm². The test results of some of the compounds and the organic el ectrolumine scent elements prepared in comparative examples 1-2 are shown in Table 1.

TABLE 1

| Test compounds | Driving voltage (V) | Strongest luminescent peak (nm) | Current efficiency (cd/A) |
|---|---|---|---|
| CJHP07 | 3.83 | 464 | 7.55 |
| CJHP40 | 4.52 | 465 | 7.07 |
| CJHP63 | 3.54 | 463 | 7.96 |
| CJHP99 | 3.71 | 465 | 7.80 |
| CJHP133 | 3.96 | 464 | 7.29 |
| CJHP167 | 4.60 | 464 | 6.85 |
| CJHP176 (T$_3$=S) | 4.48 | 464 | 6.72 |
| CJHP204 | 4.55 | 466 | 7.16 |
| CJHP244 | 3.69 | 466 | 7.74 |
| Comparative example 1 | 4.77 | 463 | 5.82 |
| Comparative example 2 | 4.92 | 466 | 6.45 |

It can be seen from Table 1 that compared with the organic electroluminescent element using Alq3 in the electron transport layer and the organic electroluminescent element without the electron transport layer, the organic electroluminescent elements using the compounds prepared according to the present invention in the electron transport layer show excellent performance in terms of driving voltage, current efficiency, and strongest luminescent peak.

The test results of the other compounds are basically the same as data in Table 1 and not listed again for a reason of a limited space.

Test Example 2

The compounds prepared in examples 1-14 are respectively refined by sublimation. The following organic electroluminescent elements are manufactured.
(1) an ITO-coated glass substrate is ultrasonically washed with distilled water, ultrasonically washed with an isopropanol and an acetone/ethanol mixed solvent, baked in a clean environment to be completely dried, irradiated with an ultraviolet light cleaning machine for 10 minutes, cleaned by UV for 5 minutes, and transferred to a vacuum evaporation machine.
(2) the treated ITO electrode is sequentially stacked with HT002 (BaYi Space, 300 Å)/HT022 (BaYi Space, 2100 Å)/HT001 (BaYi Space, 100 Å)/each of compounds CJIP01-CJHP252+2% RD018 (BaYi Space, 300 Å)/50% CJHP63+50% Liq(300 Å)/LiF(10 Å)/Al(1500 Å) to manufacture an organic electroluminescent element.

Comparative Example 3

Except that as a host substance of an emission layer, RH03 is used to replace compounds CJHIP01-CJHP252, the operation is the same as that in test example 2 to prepare an organic electroluminescent element.

A structure of the RH03 is as follows:

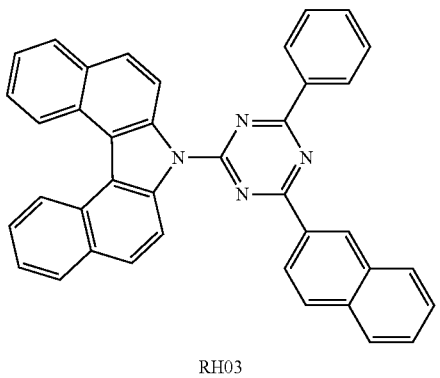 [SMILES: c1ccc(-c2nc(-c3ccc4ccccc4c3)nc(-n3c4ccc5ccccc5c4c4c5ccccc5ccc43)n2)cc1 ; "RH03"]

RH03

The driving voltage, current efficiency, and luminescent peak of the organic electroluminescent elements respectively manufactured in test example 2 and comparative example 3 are measured when a current density is 10 mA/cm². The test results of some of the compounds and comparative examples 3 are shown in Table 2.

TABLE 2

| Test compounds | Driving voltage (V) | Strongest luminescent peak (nm) | Current efficiency (cd/A) |
|---|---|---|---|
| CJHP07 | 4.20 | 624 | 26.39 |
| CJHP63 | 4.14 | 625 | 26.88 |
| CJHP133 | 4.10 | 624 | 25.92 |
| CJHP167 | 4.18 | 624 | 26.75 |
| CJHP176 (T$_3$=O) | 4.11 | 624 | 26.96 |
| CJHP196 (T$_3$=O) | 4.05 | 625 | 27.97 |
| CJHP204 | 4.08 | 624 | 27.05 |
| CJHP205 | 4.06 | 624 | 27.26 |
| CJHP241(T$_3$=N—Ph) | 4.13 | 624 | 26.84 |
| CJHP244 | 4.15 | 625 | 26.80 |
| Comparative example 3 | 4.22 | 624 | 25.24 |

It can be seen from Table 2 that compared with the organic electroluminescent element using RH03 in the host of the emission layer, the organic electroluminescent elements using the compounds prepared according to the present invention in the host of the emission layer show excellent performance in terms of driving voltage, current efficiency, and strongest luminescent peak.

The test results of the other compounds are basically the same as data in Table 2 and not listed again for a reason of a limited space.

Based on the above analysis, the organic electroluminescent elements produced using the compounds of the present invention may be used in a plane luminophor such as a mobile phone, a wall-mounted television, a flat-panel display, and a lighting device, a backlight of a copying machine, a printer, and a liquid crystal display, a light source of a measuring instrument, a display panel, a marker lamp, and the like.

The foregoing descriptions are merely specific embodiments of the present invention, but the protection scope of the present invention is not limited thereto. Any modification or replacement easily conceived by those skilled in the art within the technical scope of the present invention should fall within the protection scope of the present invention. Therefore, the protection scope of the present invention shall be the protection scope of the claims.

What is claimed is:

1. An organic compound, wherein the compound has a structural formula as shown in a formula (I):

Formula (I)

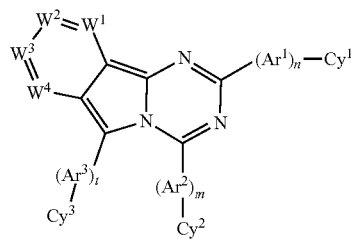

wherein $W^1$-$W^4$ are the same or different from each other and are each independently selected from $CR^1$;

the $R^1$ is selected from hydrogen;

$Ar^1$, $Ar^2$, and $Ar^3$ are single bond, $C_6$-$C_{60}$ arylene;

$Cy^1$, $Cy^2$, and $Cy^3$ are each independently selected from $C_6$-$C_{60}$ aryl or $C_2$-$C_{60}$ heteroaryl;

m, n, and t represent integers of 0-5.

2. The organic compound according to claim 1, wherein the $Cy^1$, the $Cy^2$, and the $Cy^3$ are selected from one of pyrimidine, pyrazine, triazine, imidazole, benzimidazole, phenanthroimidazole, imidazopyridine, triazolopyridine, and quinazoline.

3. An organic compound, wherein the organic compound is one of CJHP01-CJHP252 and has a specific structural formula shown as follows:

CJHP01

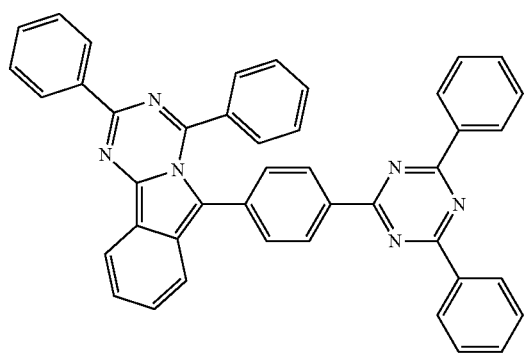

CJHP02

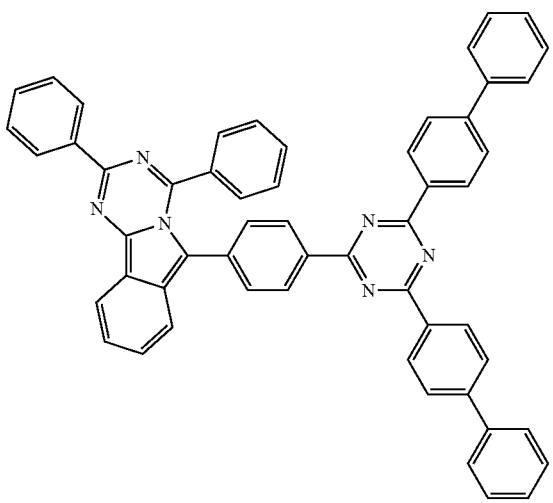

CJHP03

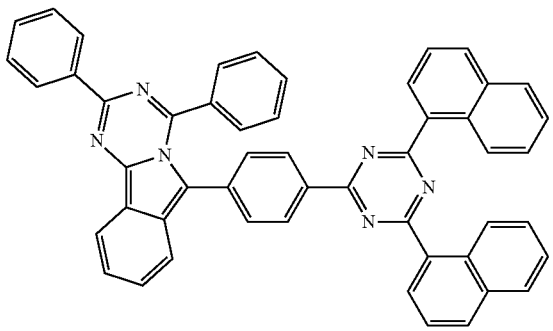

CJHP04

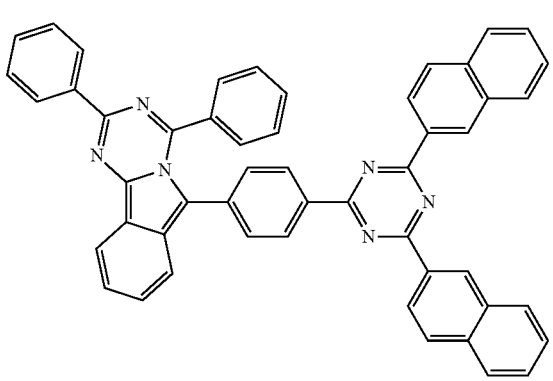

CJHP05

CJHP06
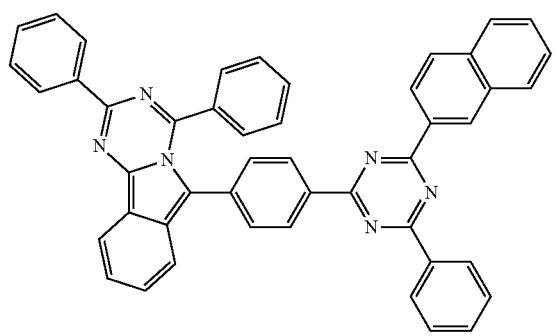
CJHP07
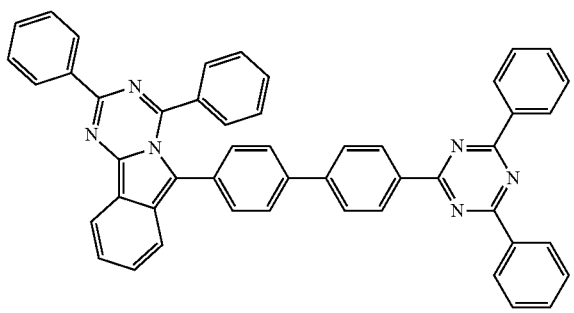
CJHP08
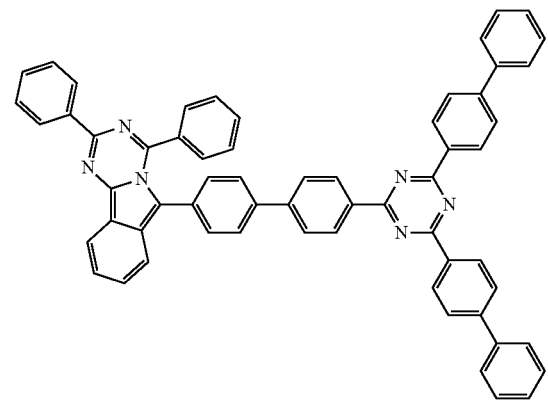
CJHP09
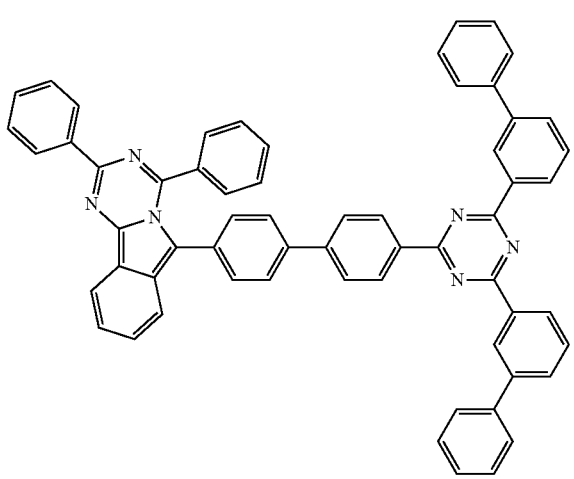
CJHP10
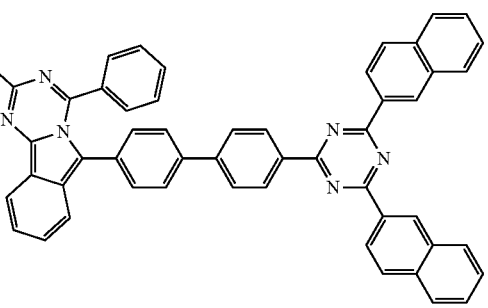
CJHP11
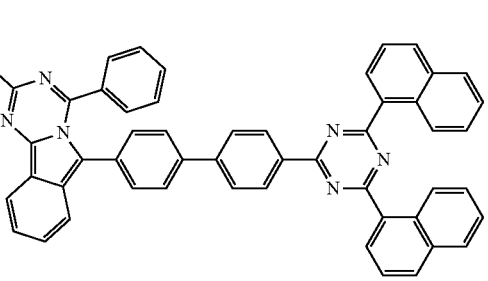
CJHP12
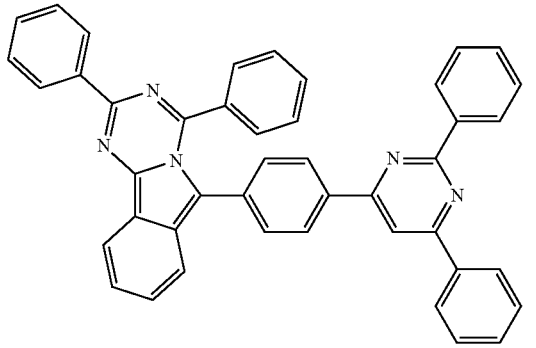
CJHP13
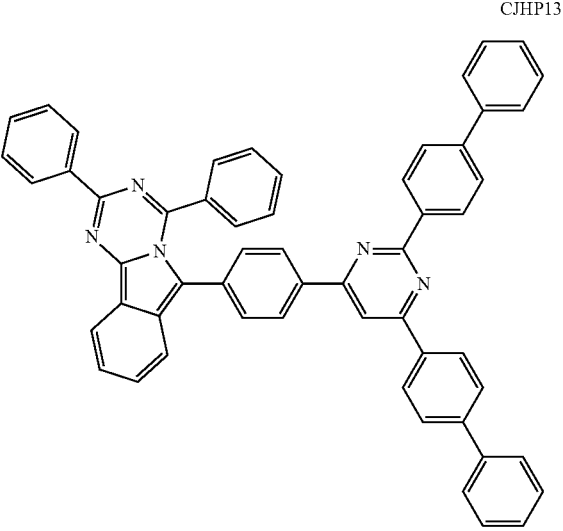

CJHP14
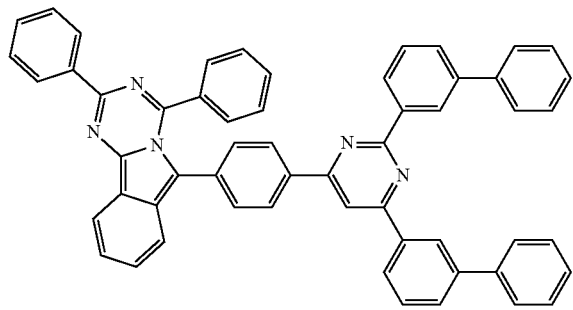
CJHP15
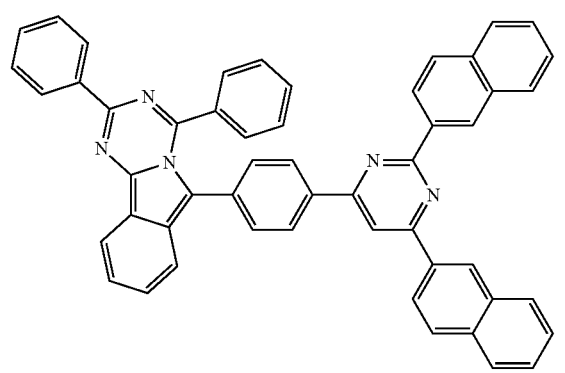
CJHP16
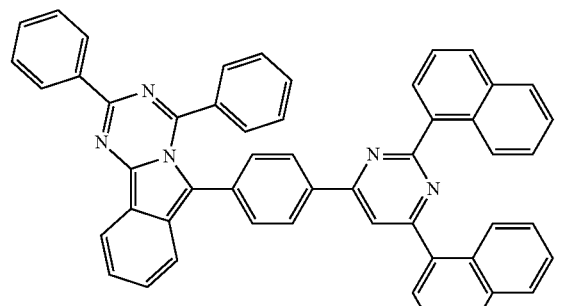
CJHP17
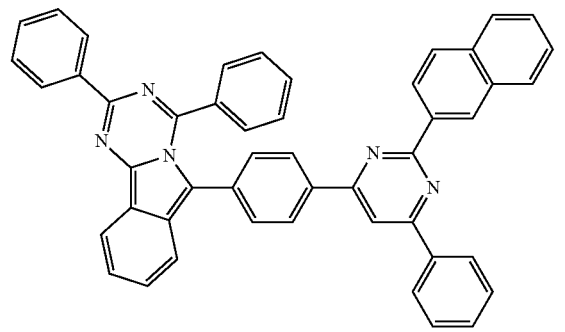
CJHP18
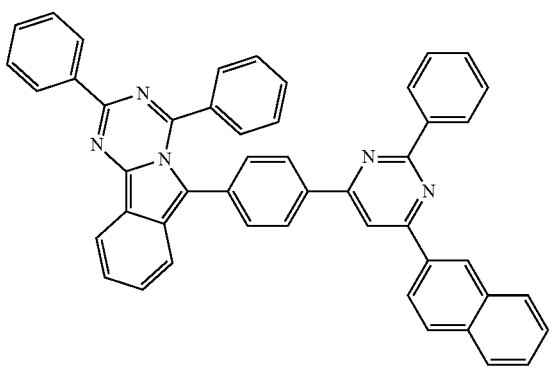
CJHP19
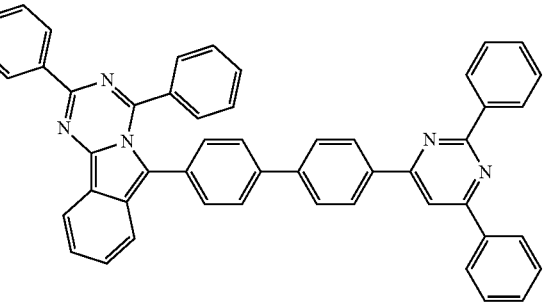
CJHP20
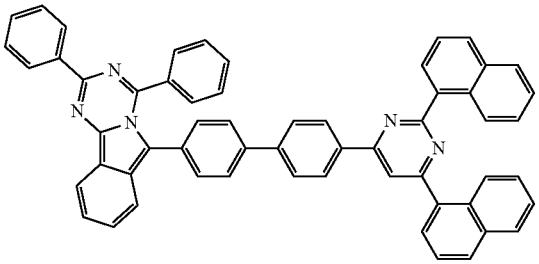
CJHP21
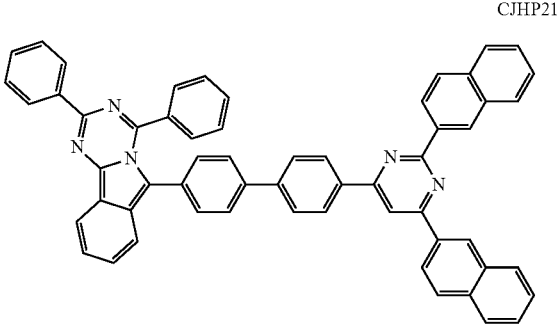

-continued
CJHP22
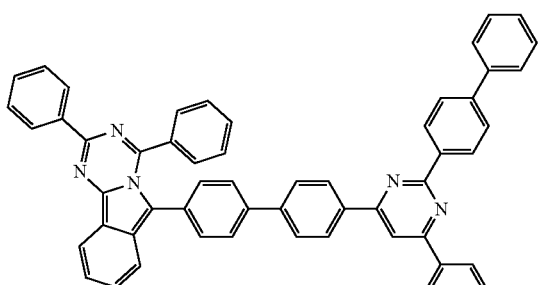
CJHP23
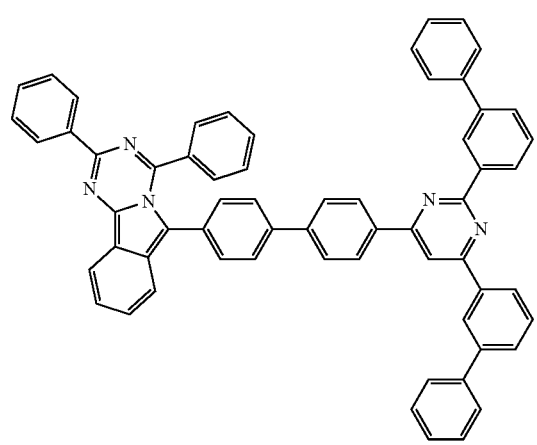
CJHP24
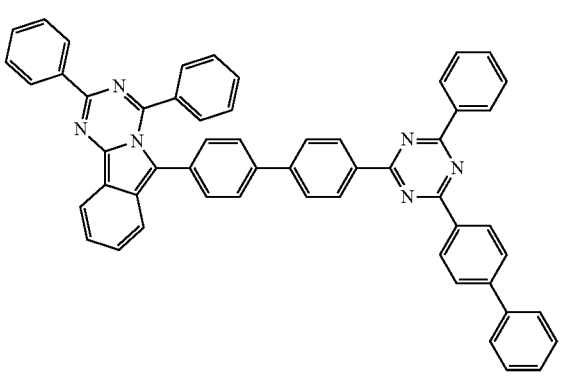
CJHP25
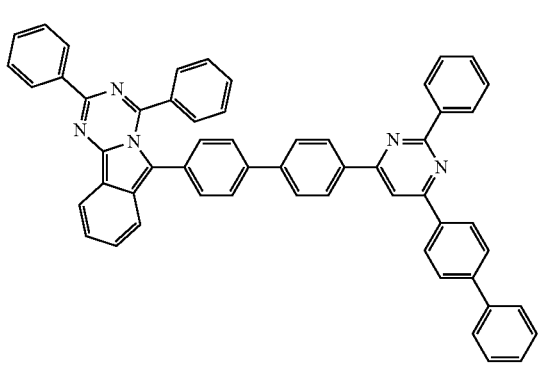
-continued
CJHP26
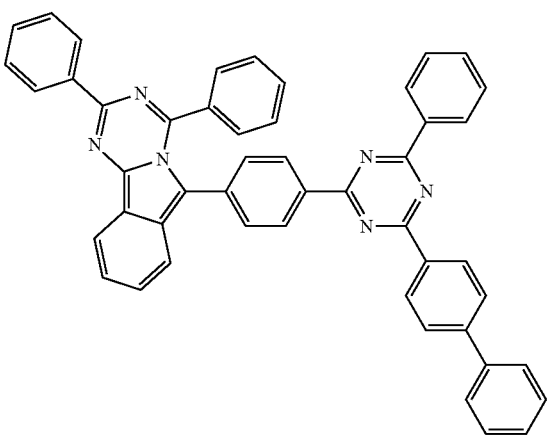
CJHP27
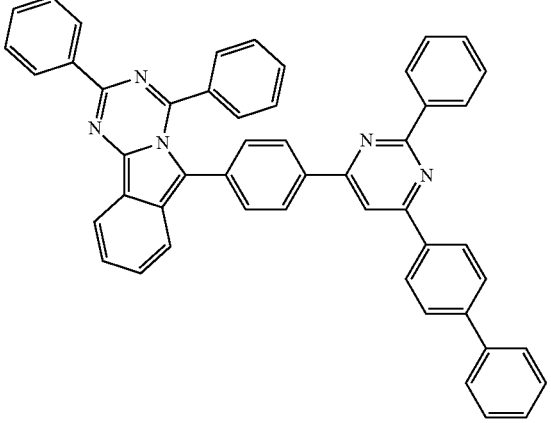
CJHP28
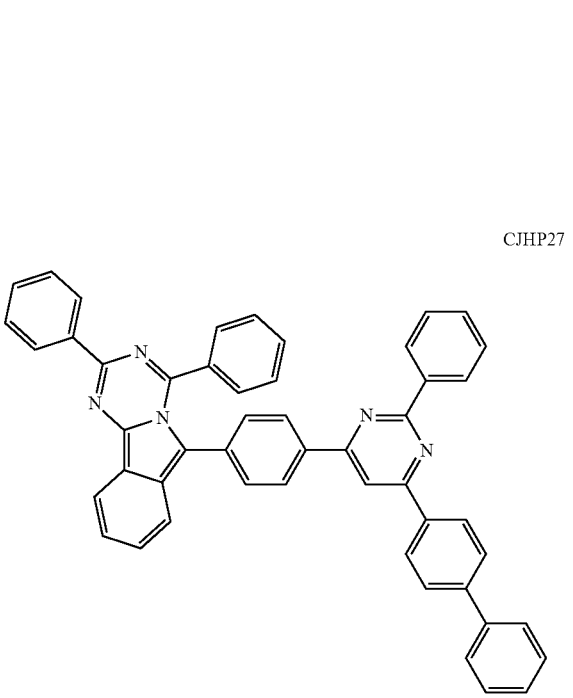

-continued
CJHP29
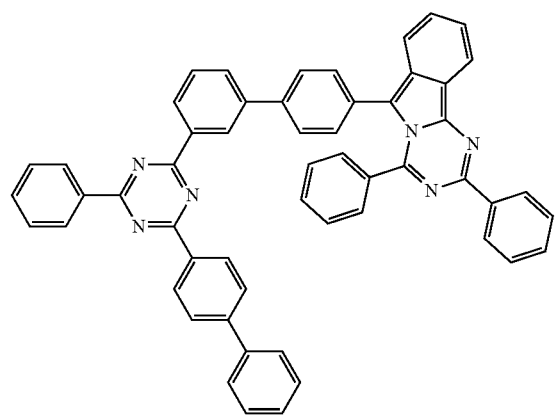
CJHP30
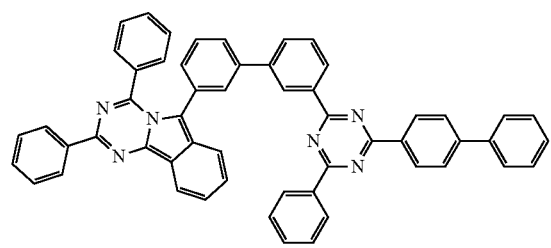
CJHP31
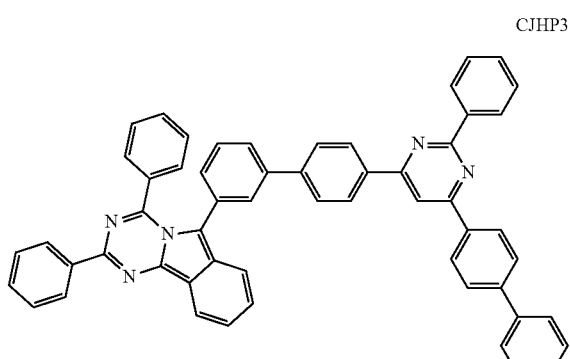
CJHP32
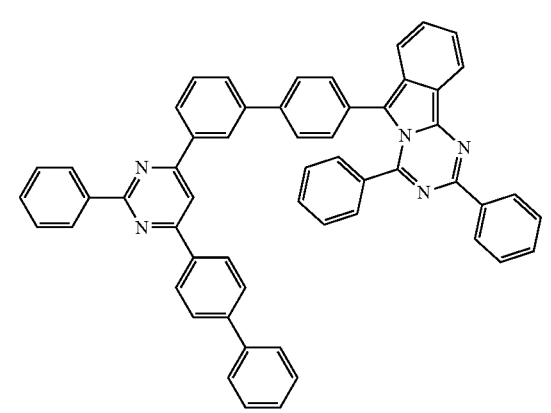
-continued
CJHP33
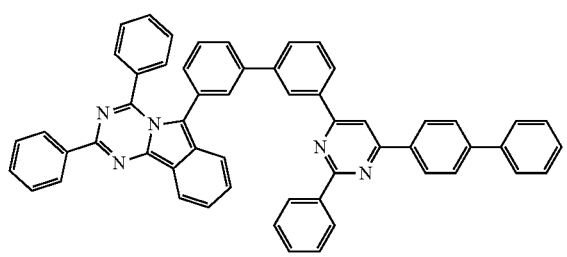
CJHP34
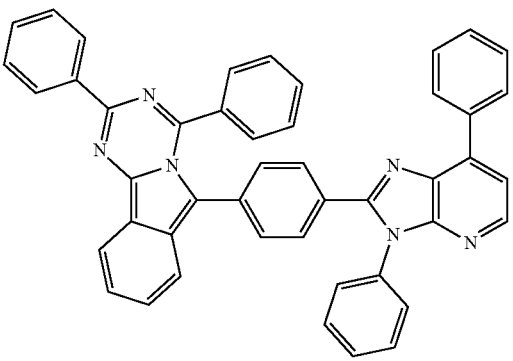
CJHP35
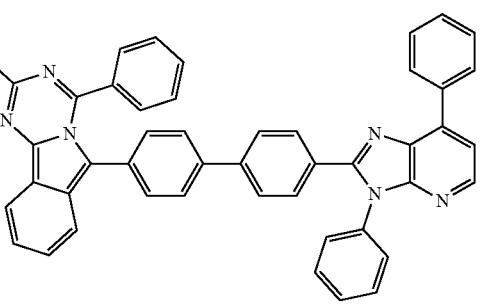
CJHP36
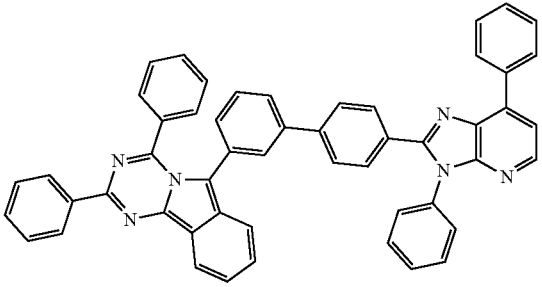

CJHP37
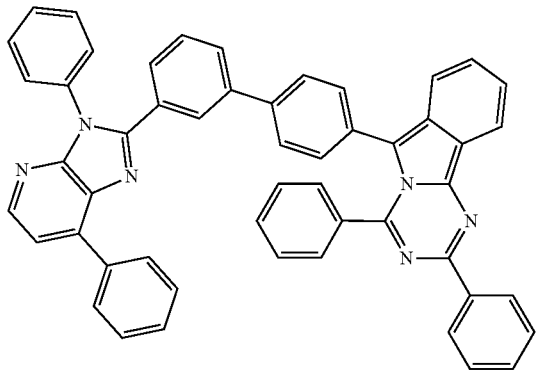
CJHP41
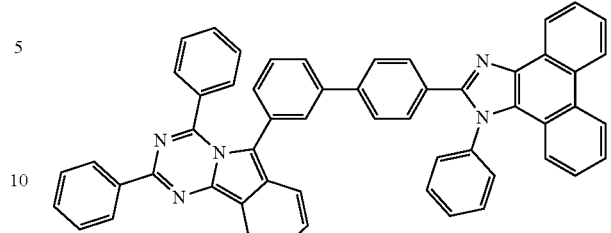
CJHP38
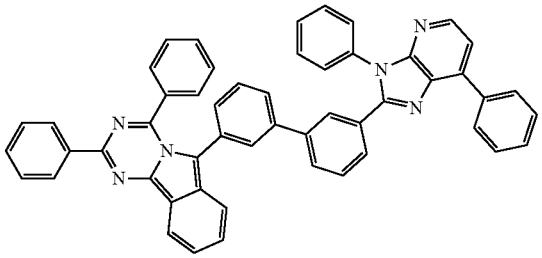
CJHP42
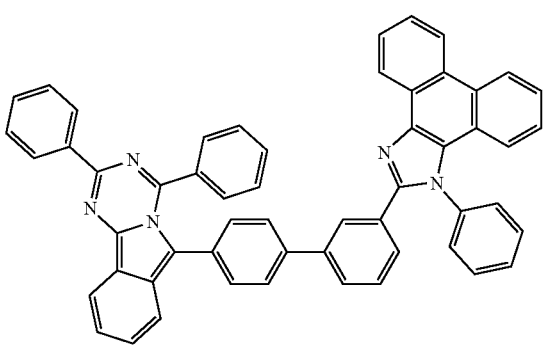
CJHP39
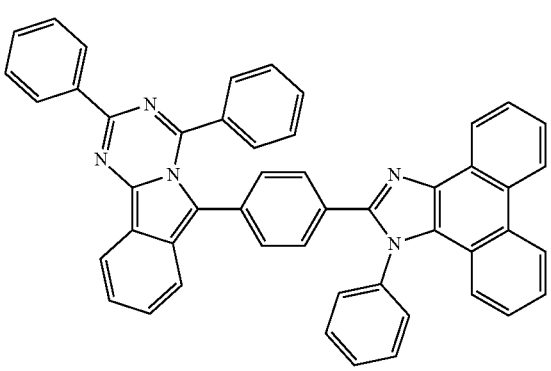
CJHP43
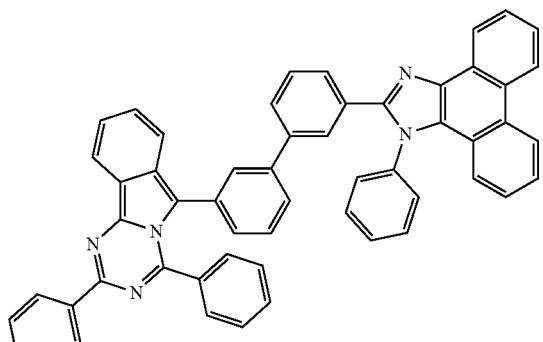
CJHP40
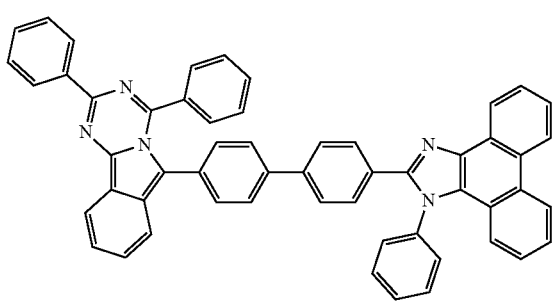
CJHP44
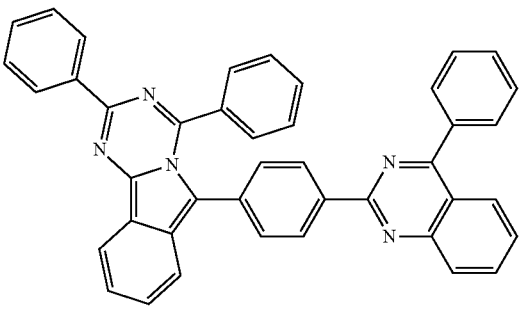

-continued
CJHP45
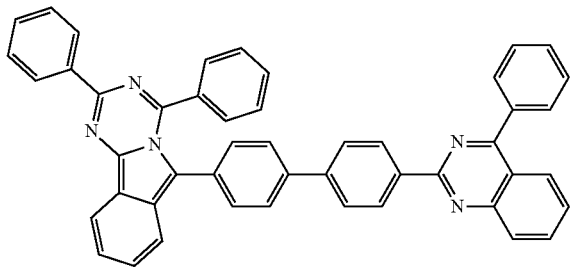
CJHP46
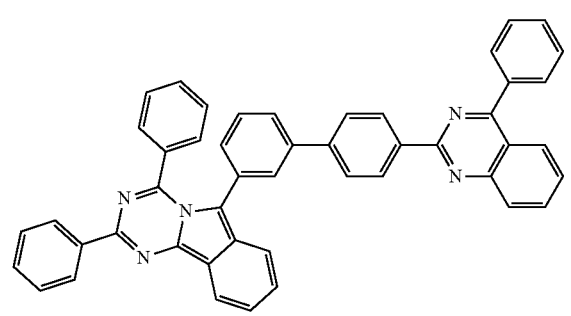
CJHP47
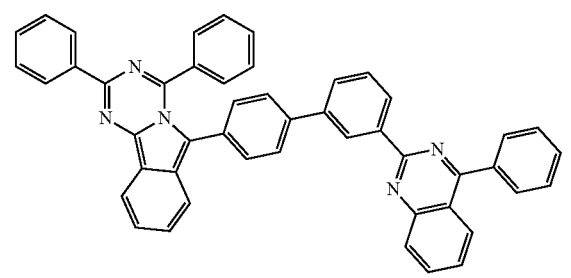
CJHP48
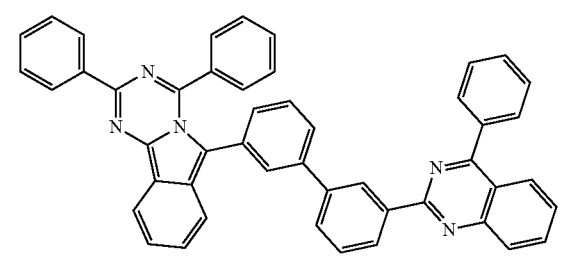
CJHP49
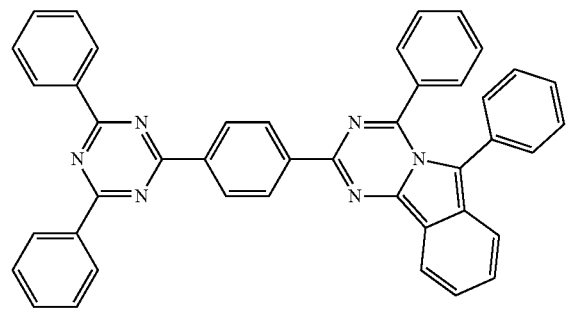
-continued
CJHP50
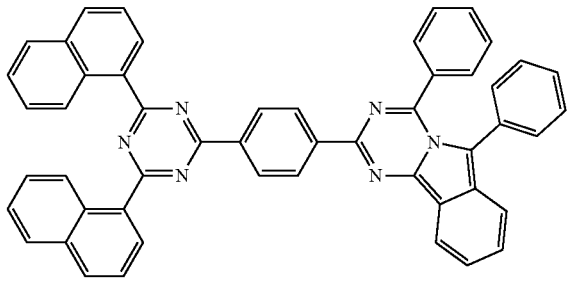
CJHP51
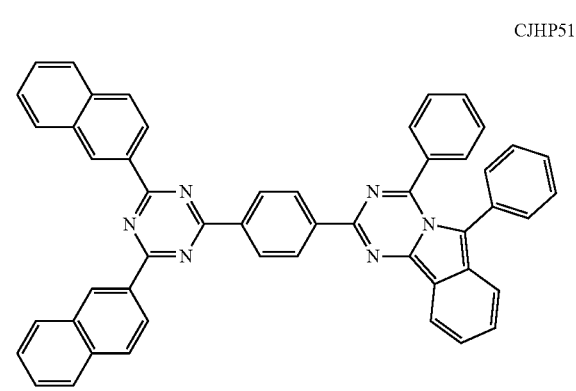
CJHP52
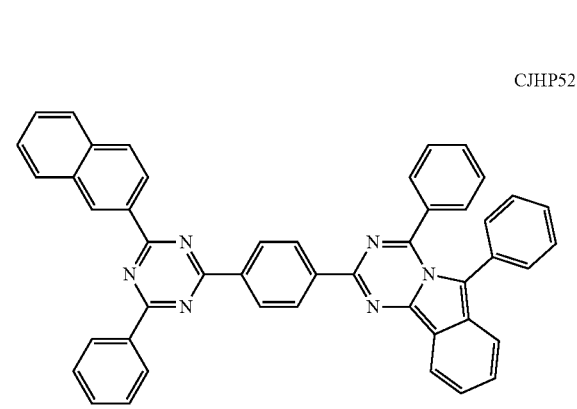
CJHP53
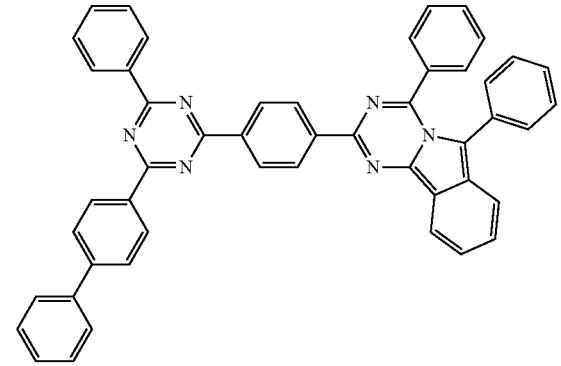

CJHP54
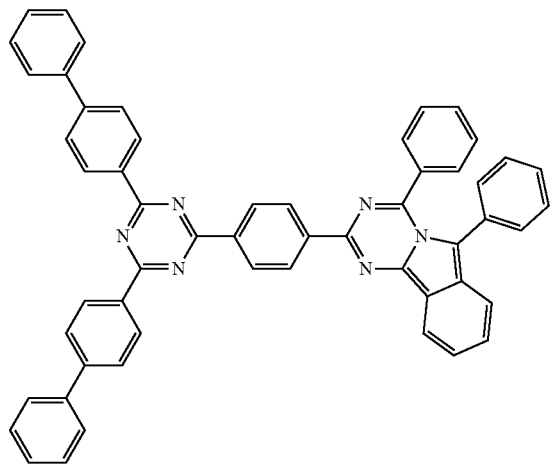
CJHP55
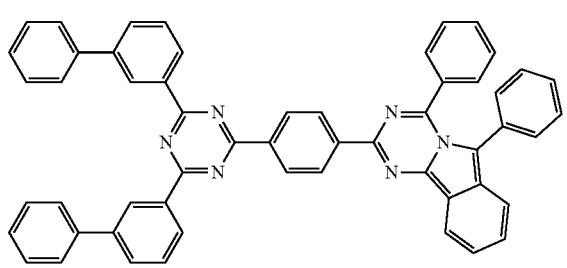
CJHP56
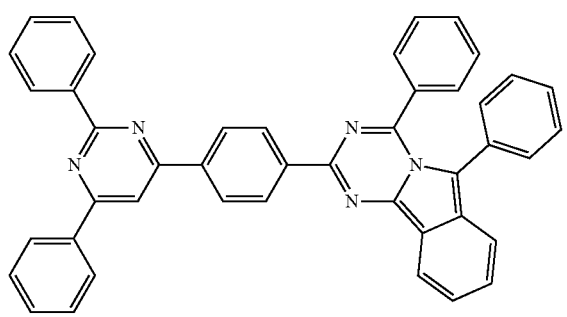
CJHP57
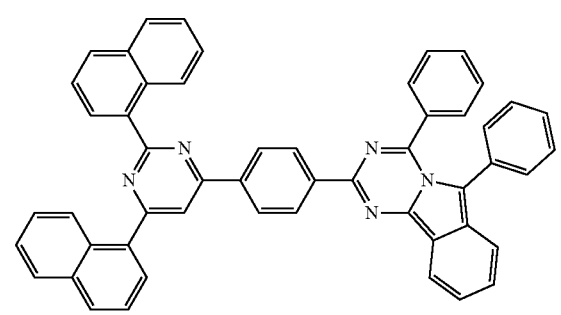
CJHP58
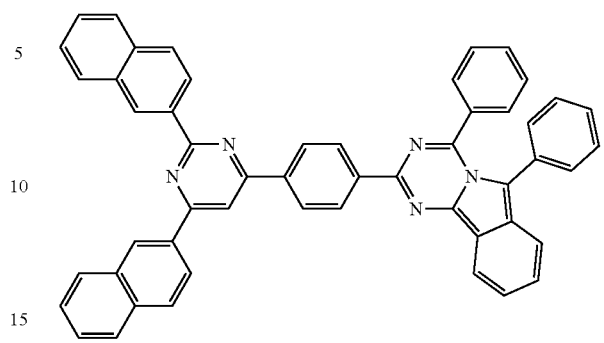
CJHP59
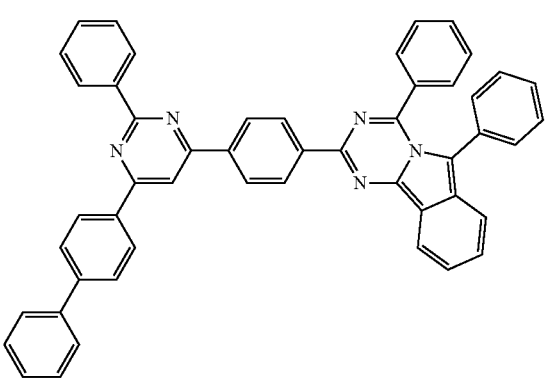
CJHP60
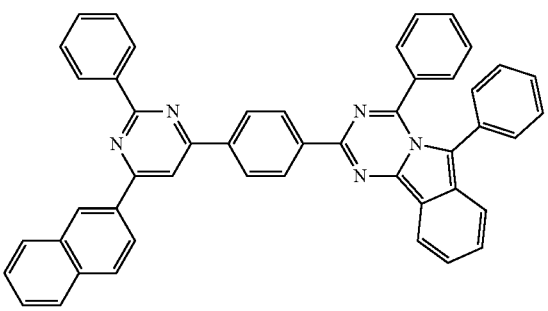
CJHP61
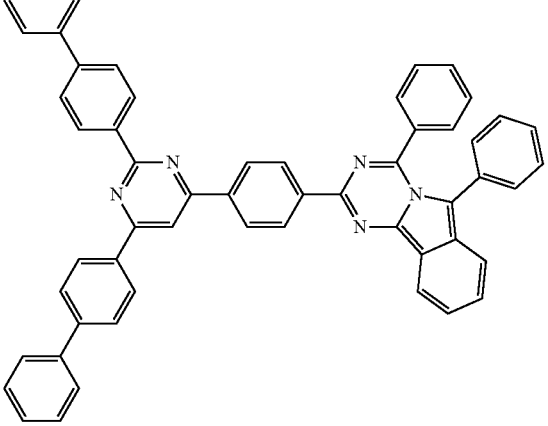

-continued
CJHP62
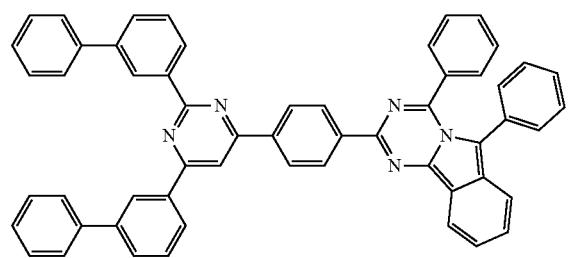
CJHP63
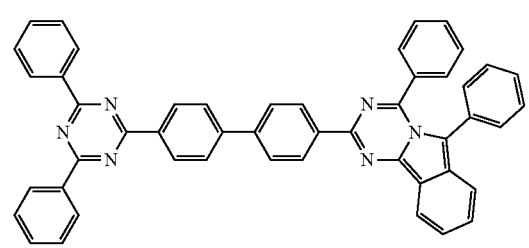
CJHP64
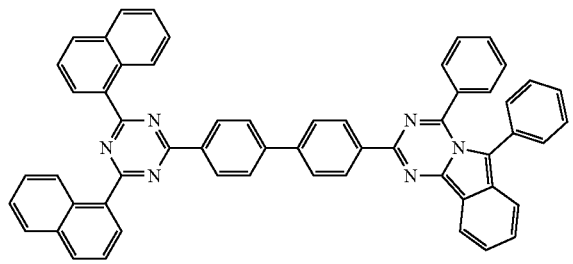
CJHP65
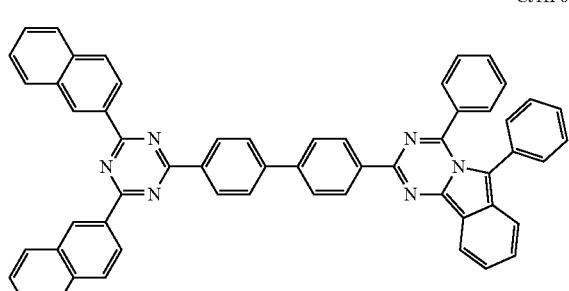
CJHP66
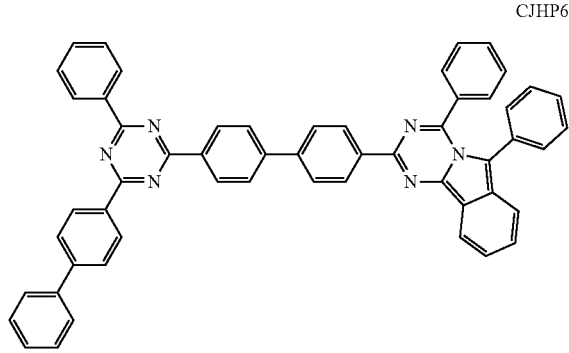
-continued
CJHP67
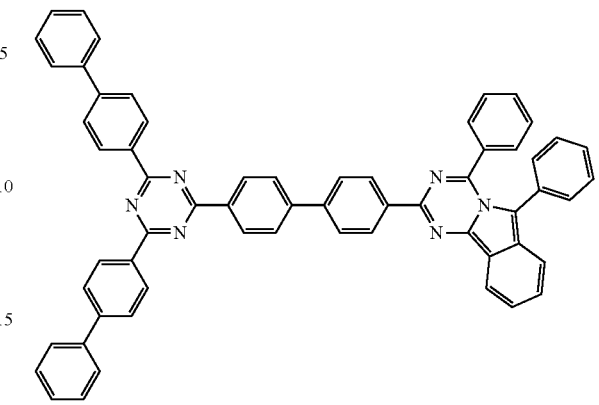
CJHP68
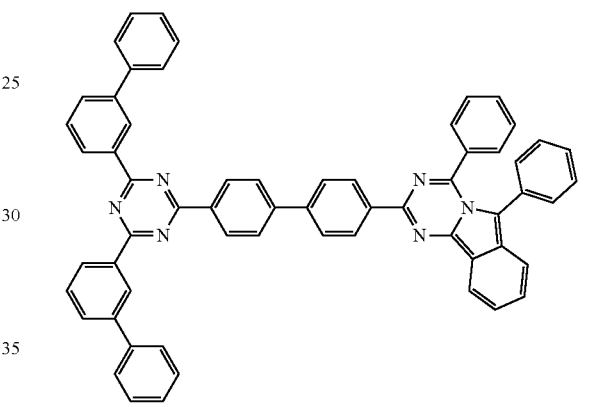
CJHP69
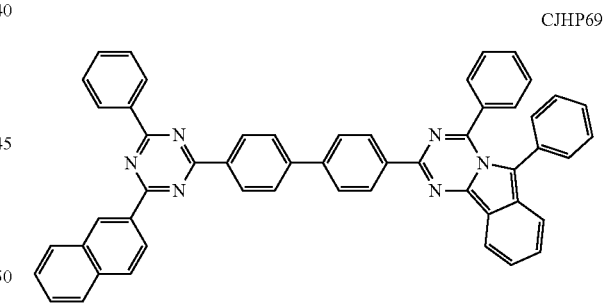
CJHP70
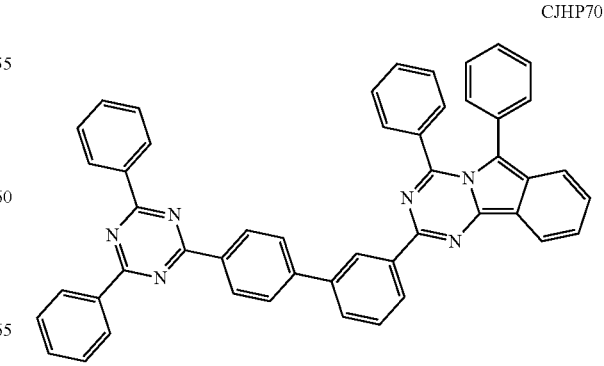

CJHP71
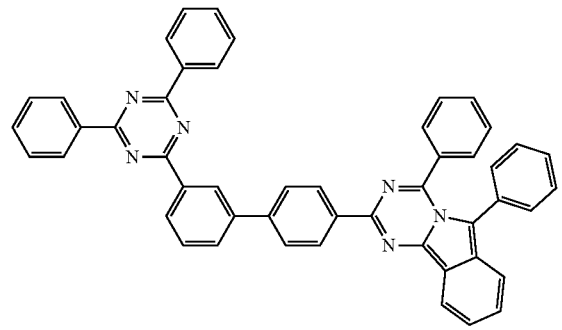
CJHP75
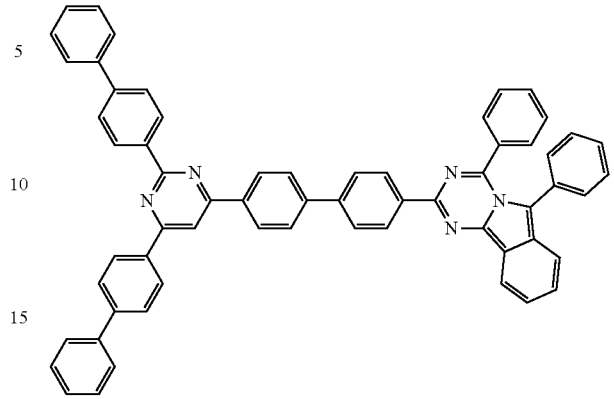
CJHP72
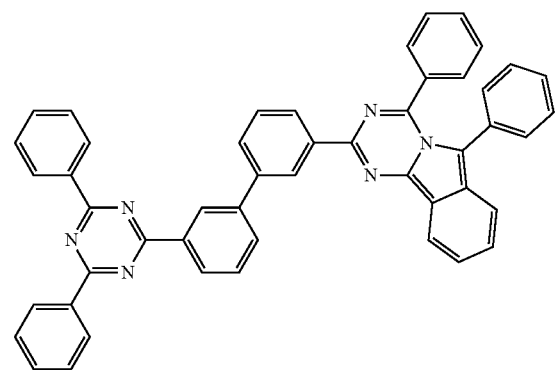
CJHP76
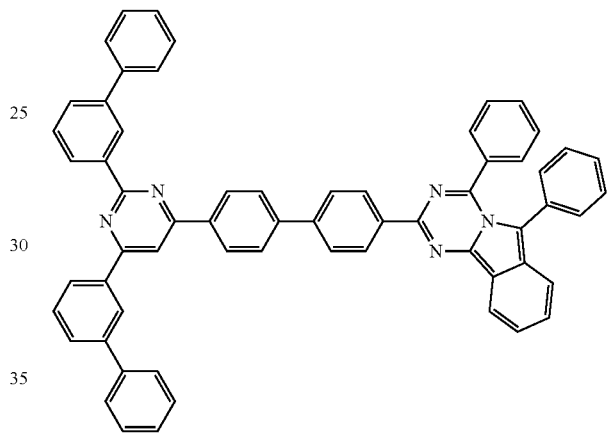
CJHP73
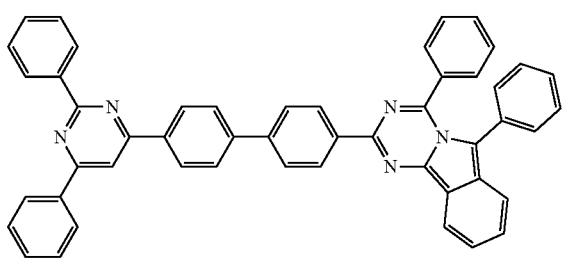
CJHP77
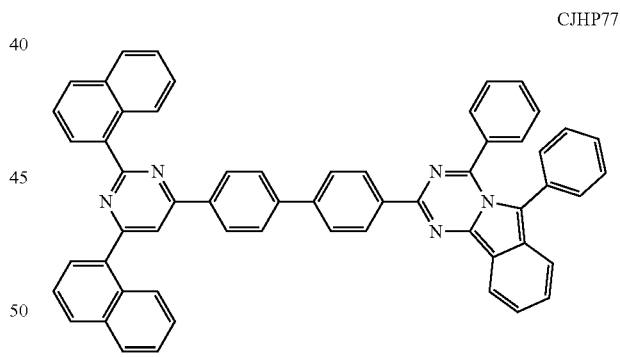
CJHP74
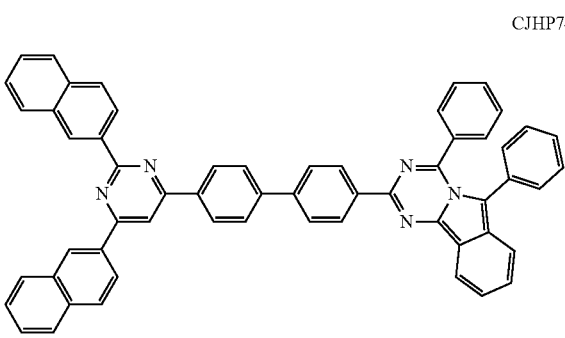
CJHP78
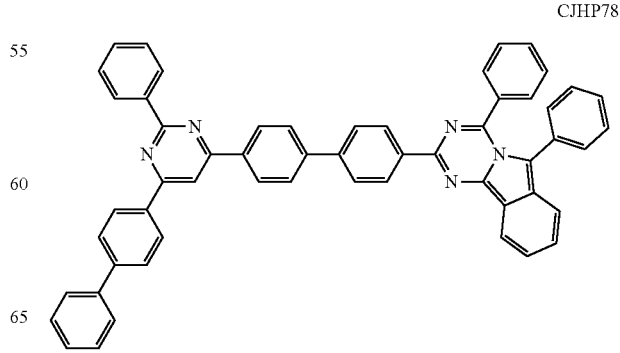

CJPHP79
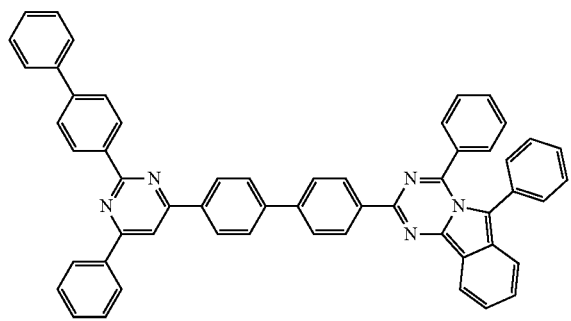
CJHP83
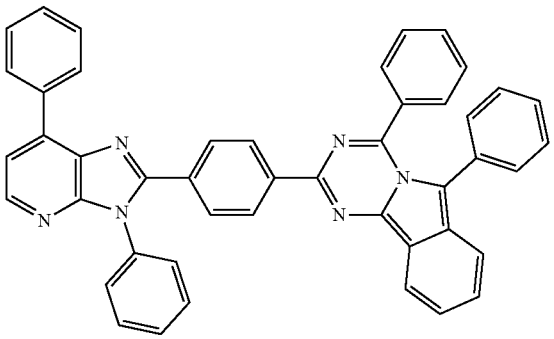
CJHP80
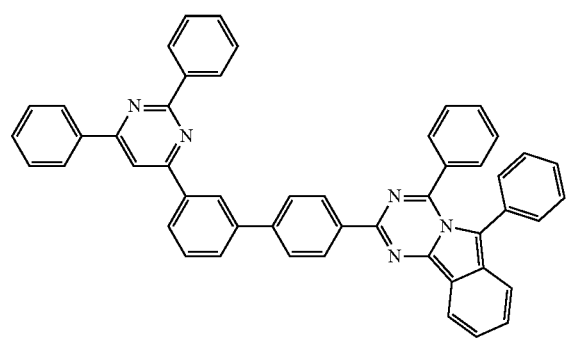
CJHP84
CJHP81
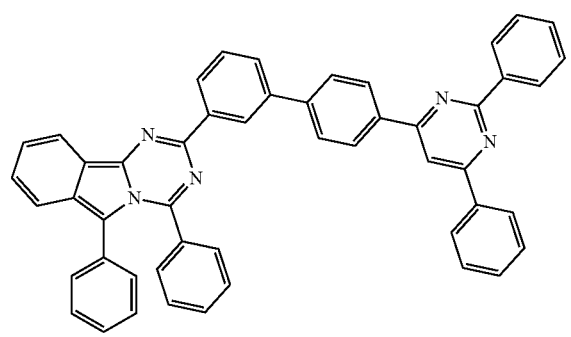
CJHP85
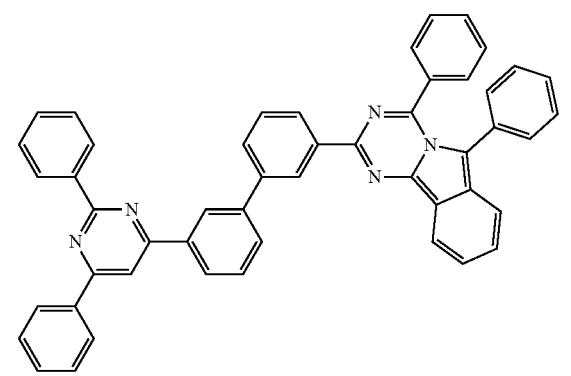
CJHP82
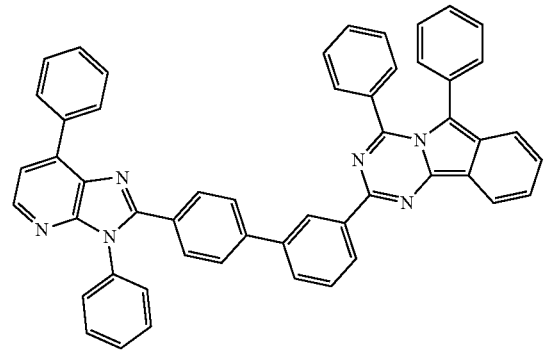
CJHP86

-continued
CJHP87
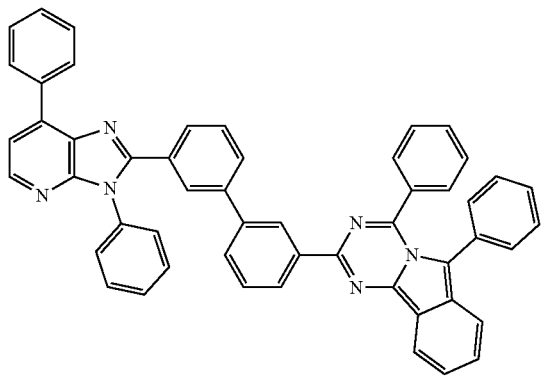
CJHP88
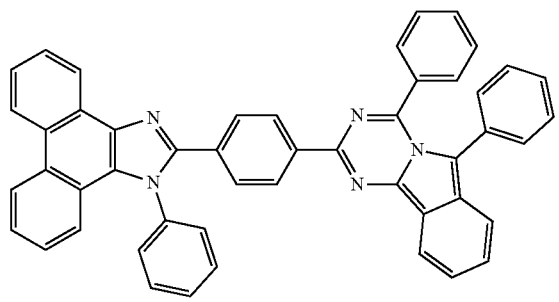
CJHP89
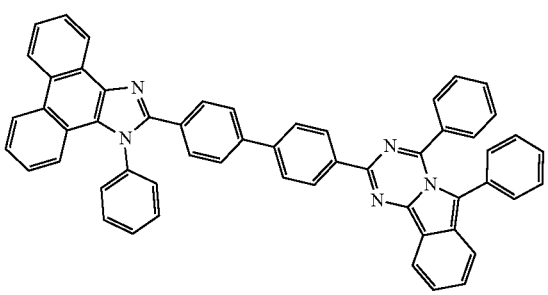
CJHP90
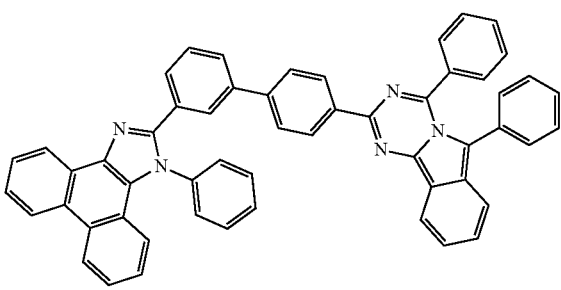
-continued
CJHP91
CJHP92
CJHP93
CJHP94
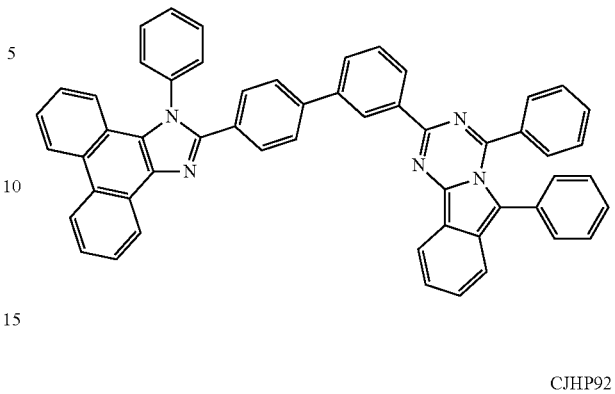
CJHP95
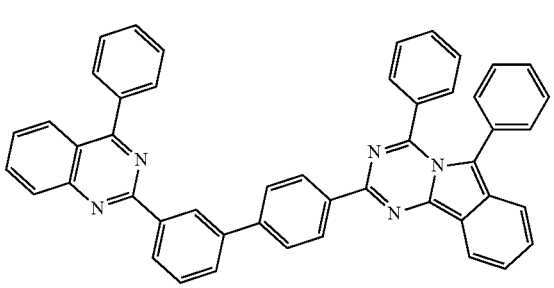

CJHP96
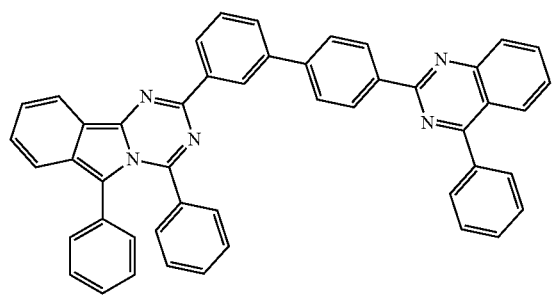
CJHP97
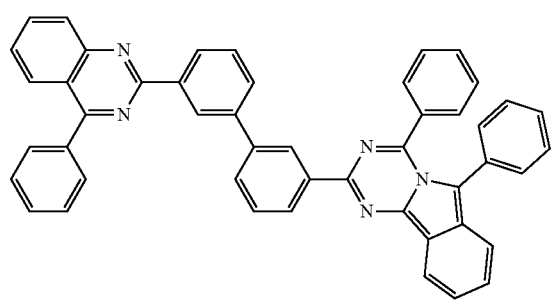
CJHP98
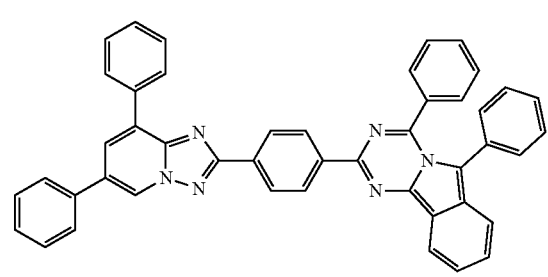
CJHP99
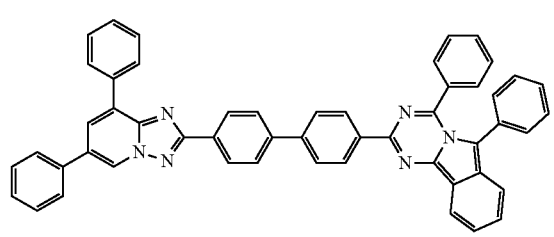
CJHP100
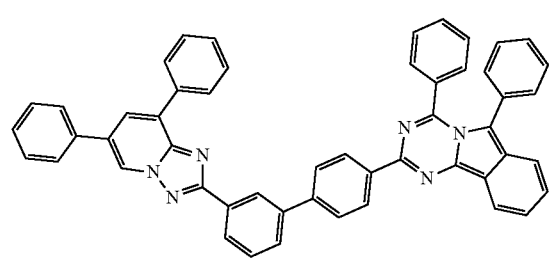
CJHP101
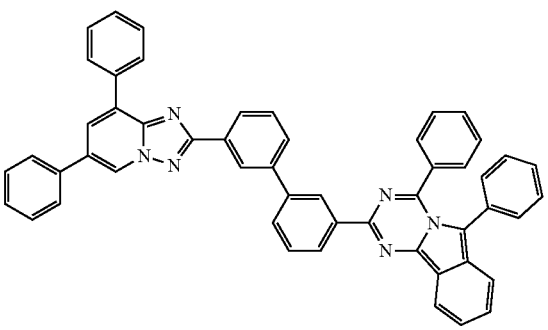
CJHP102
CJHP103
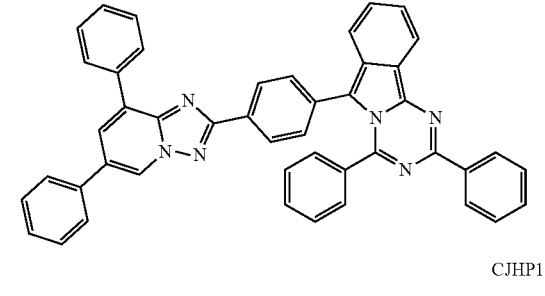
CJHP104
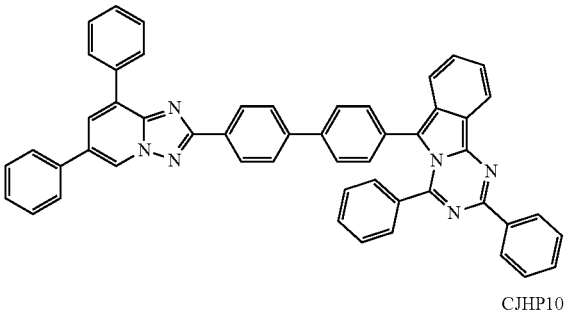
CJHP105
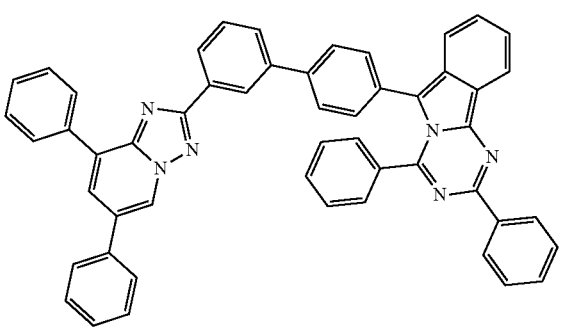

CJHP106
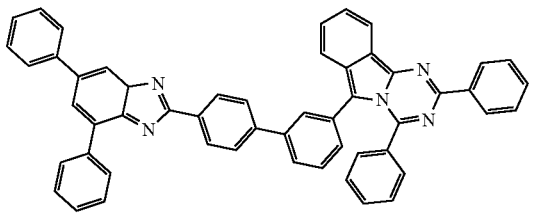
CJHP107
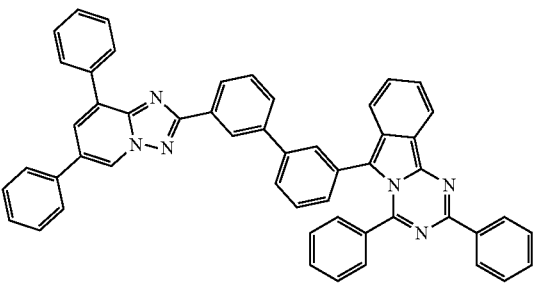
CJHP108
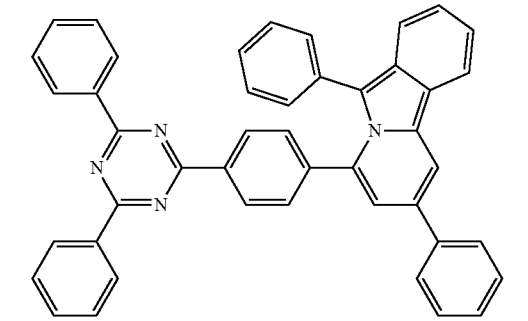
CJHP109
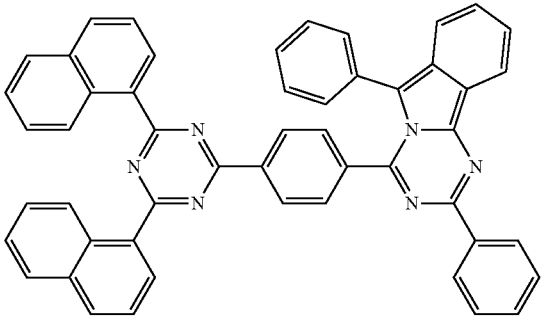
CJHP110
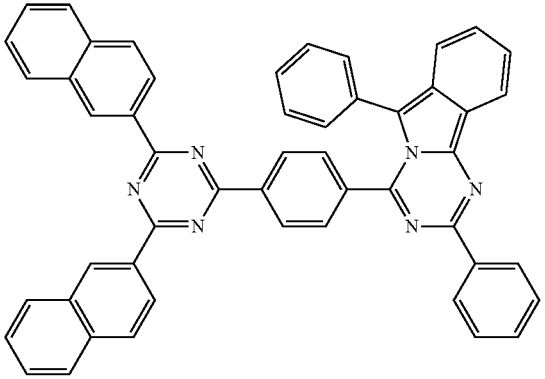
CJHP111
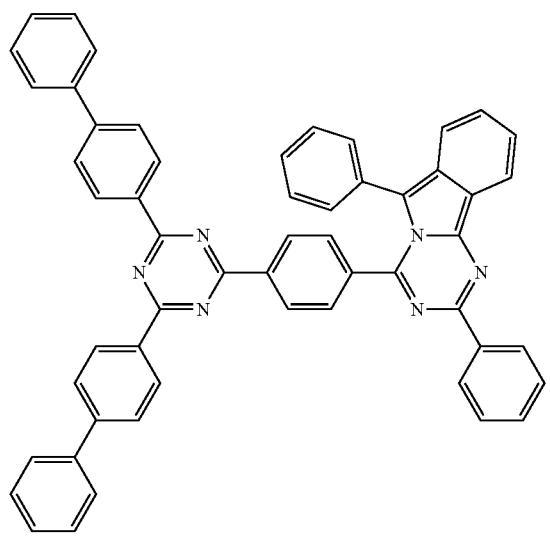
CJHP112
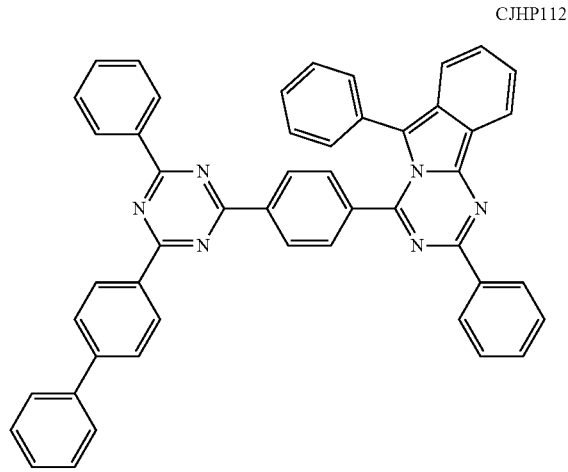
CJHP113
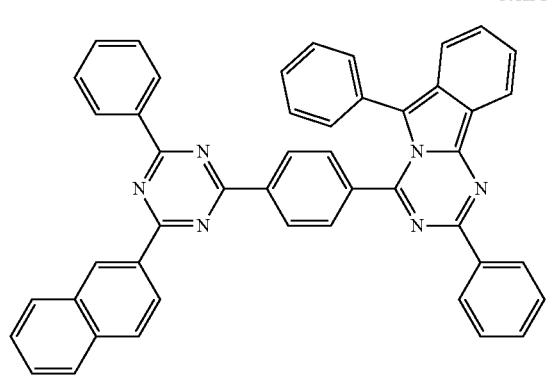

CJHP114
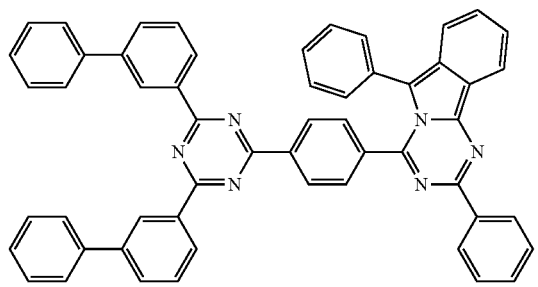
CJHP115
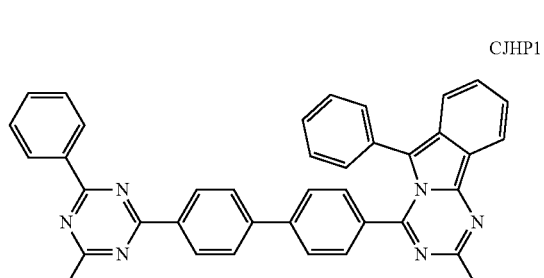
CJHP116
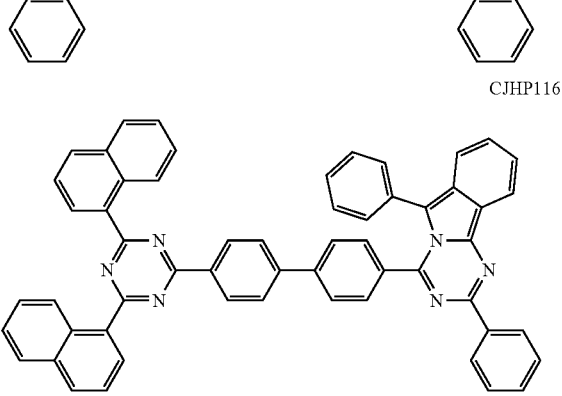
CJHP117
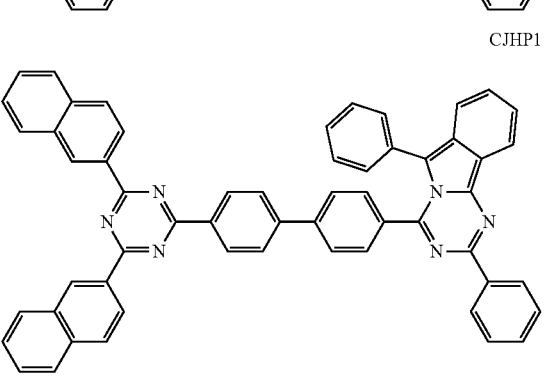
CJHP118
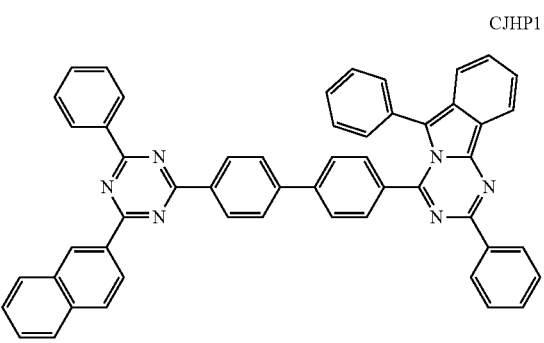
CJHP119
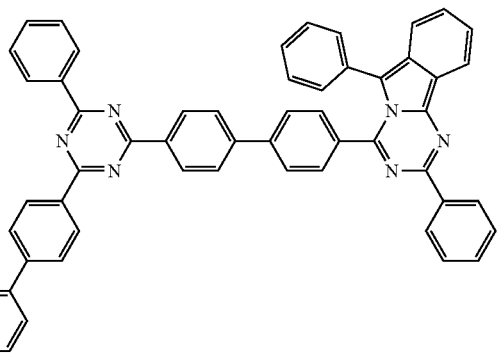
CJHP120
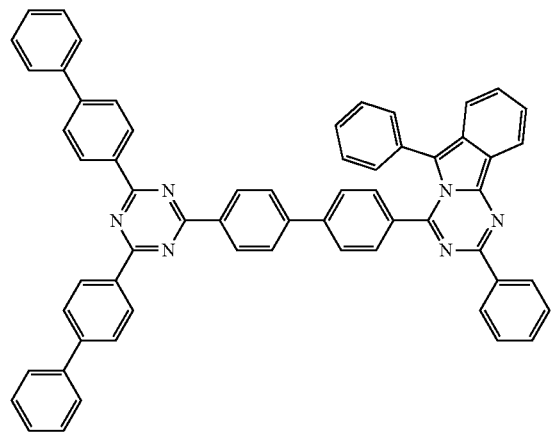
CJHP121
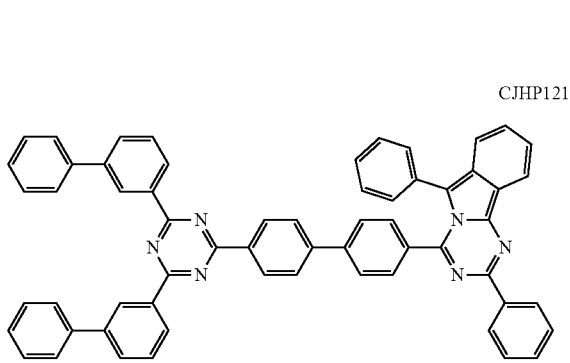
CJHP122
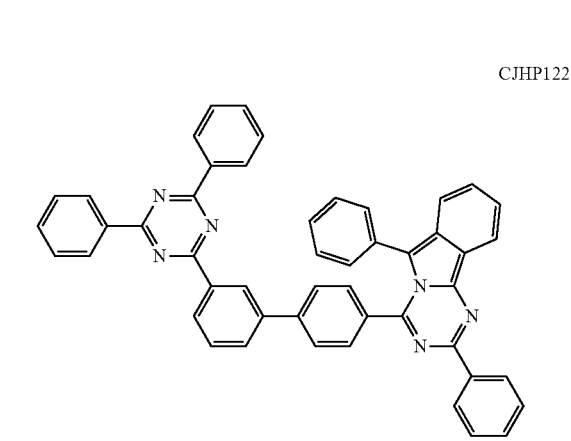

CJHP123
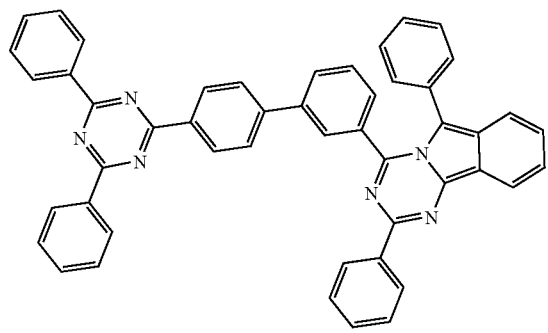
CJHP124
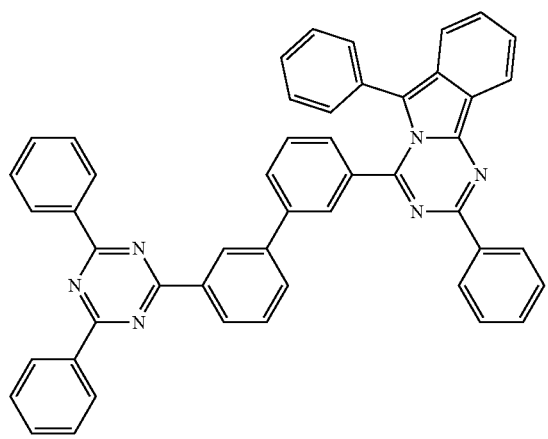
CJHP125
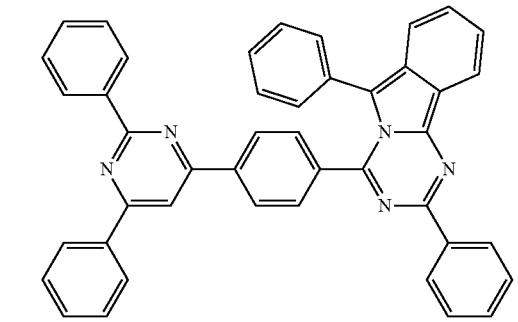
CJHP126
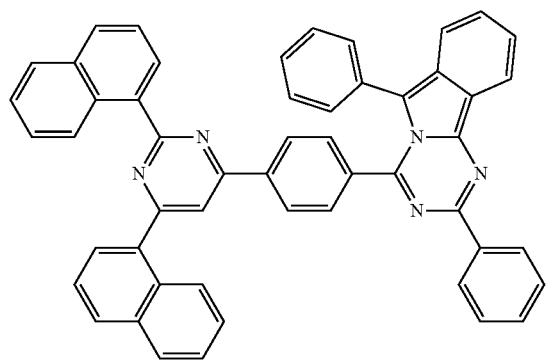
CJHP127
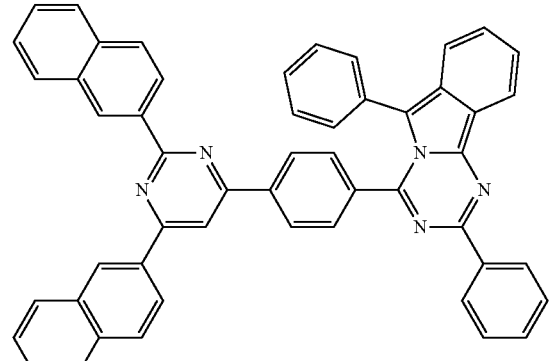
CJHP128
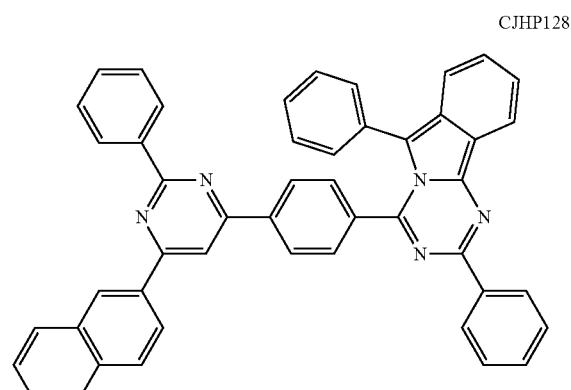
CJHP129
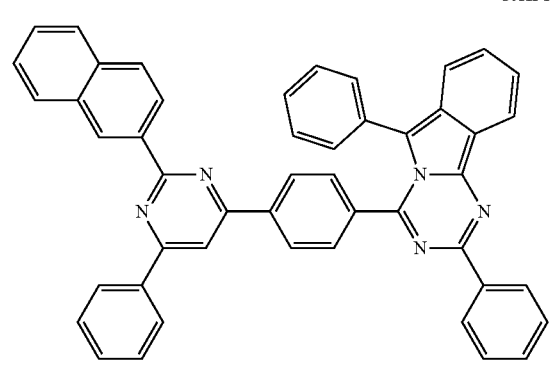
CJHP130
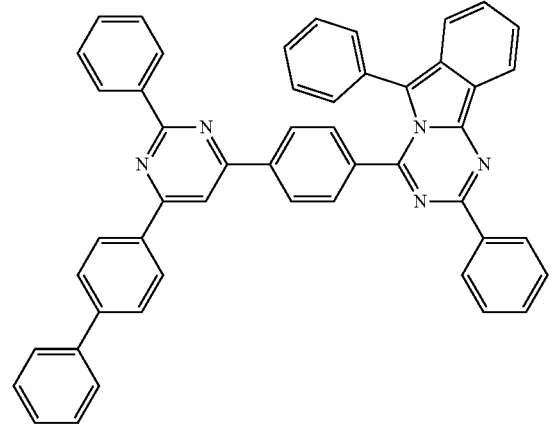

CJHP131
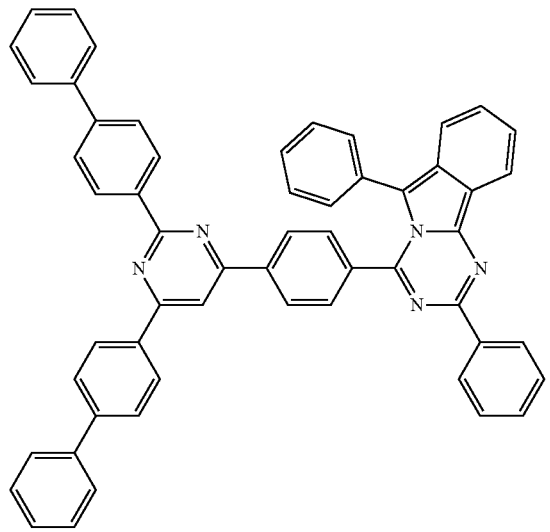
CJHP132
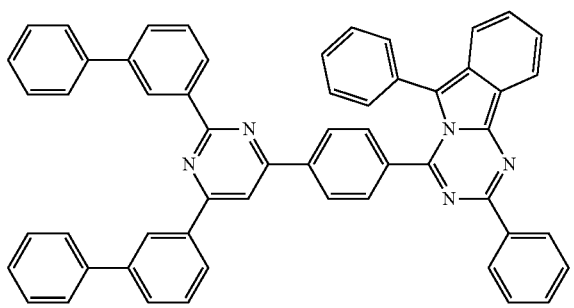
CJHP133
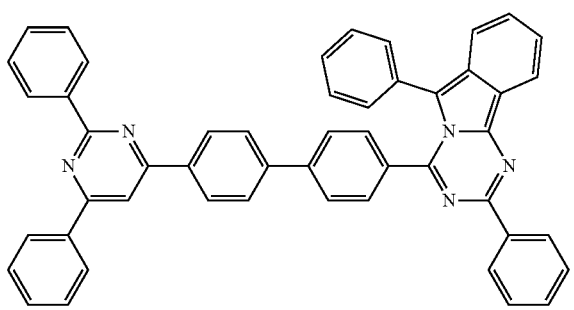
CJHP134
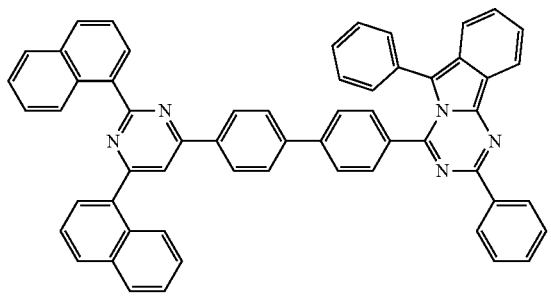
CJHP135
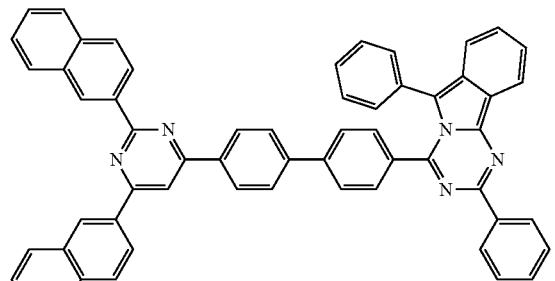
CJHP136
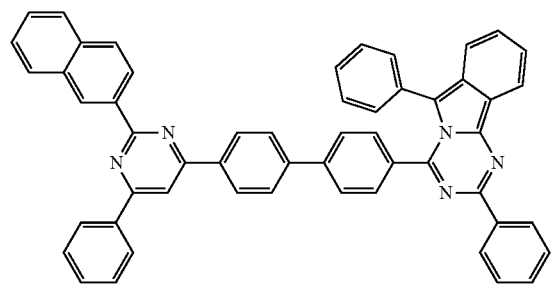
CJHP137
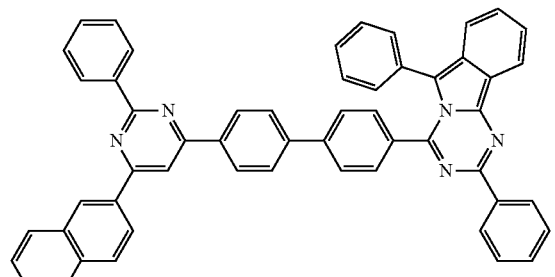
CJHP138
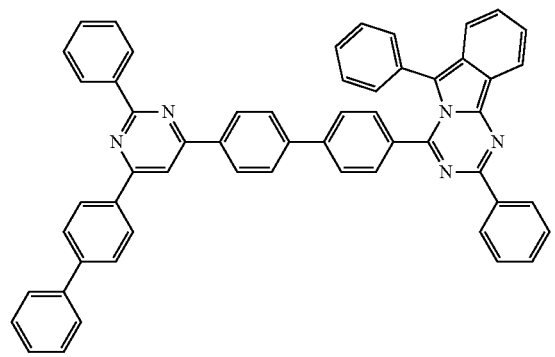

-continued

CJHP139

CJHP140

CJHP141

CJHP142

CJHP143

CJHP144

CJHP145

CJHP146

CJHP147
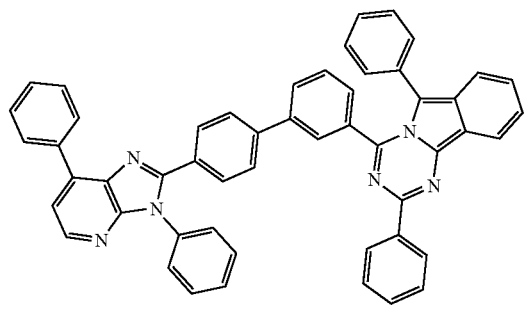
CJHP148
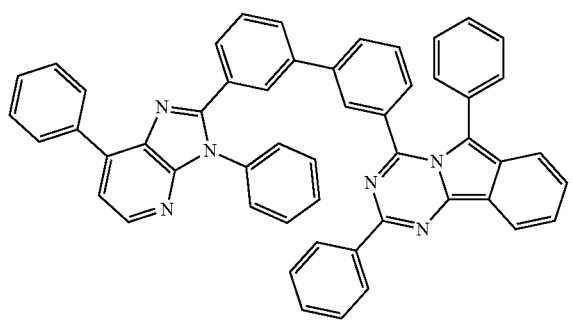
CJHP149
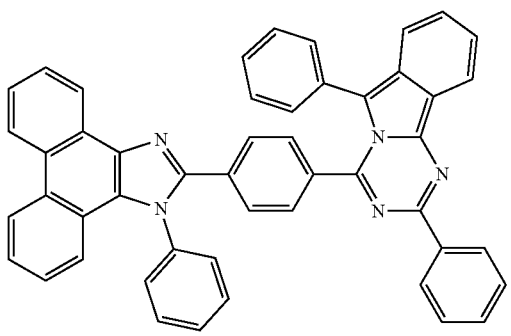
CJHP150
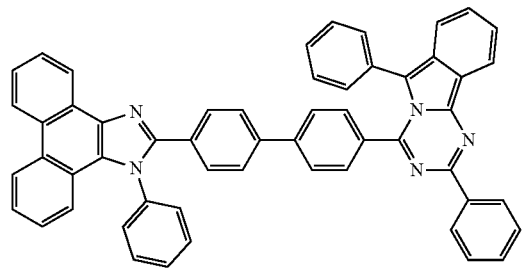
CJHP151
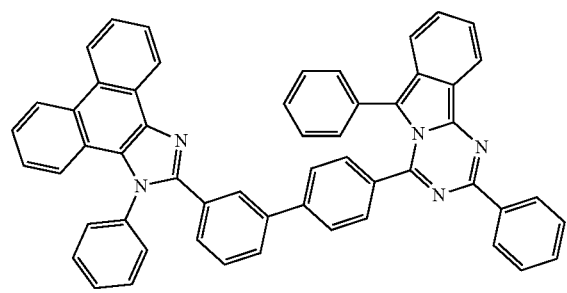
CJHP152
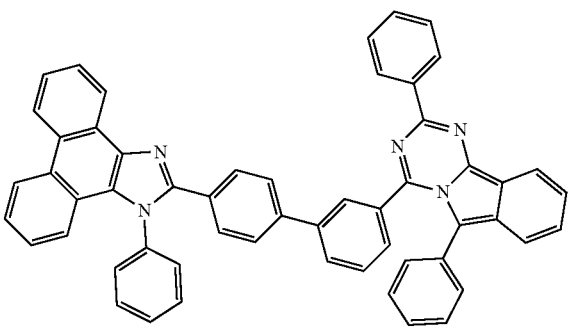
CJHP153
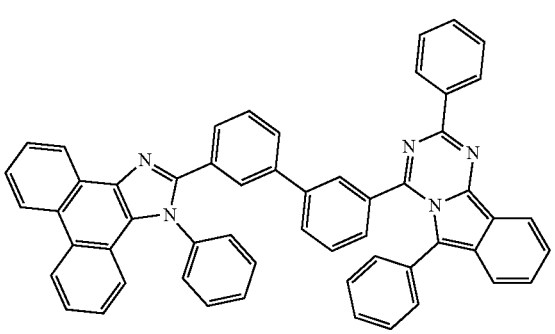
CJHP154
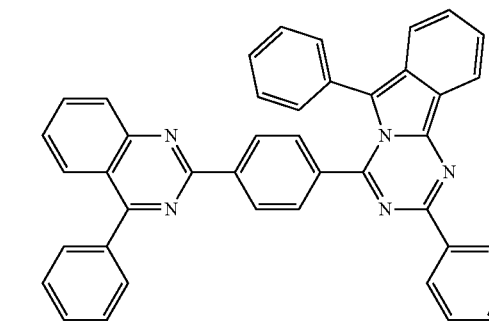
CJHP155
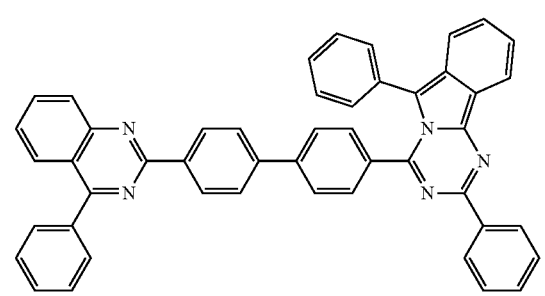

CJHP156
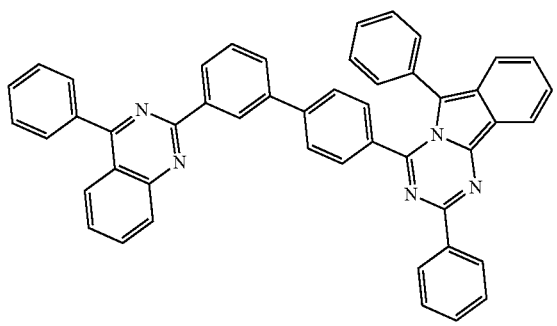
CJHP160
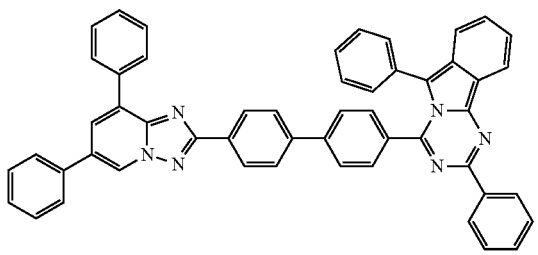
CJHP157
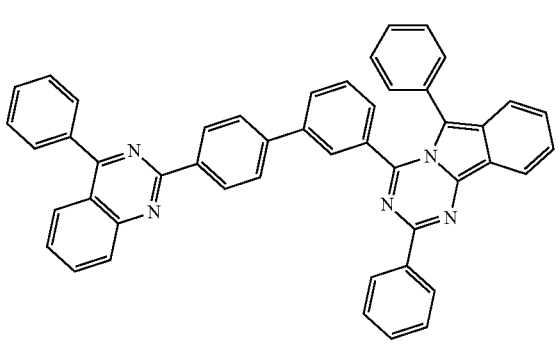
CJHP161
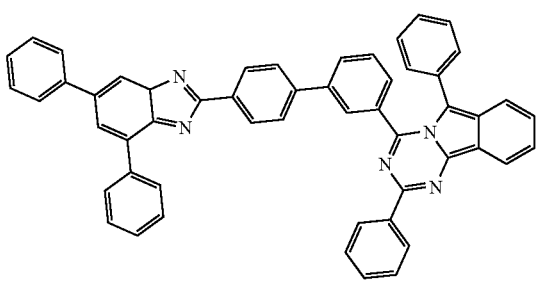
CJHP158
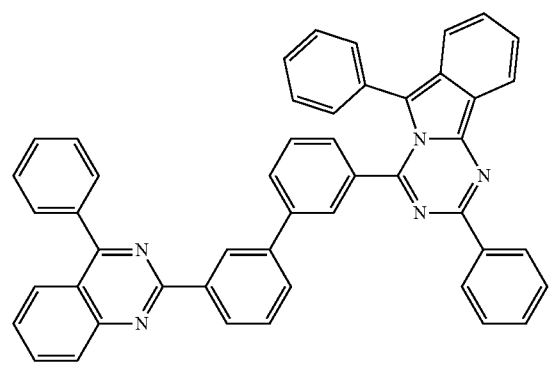
CJHP162
CJHP159
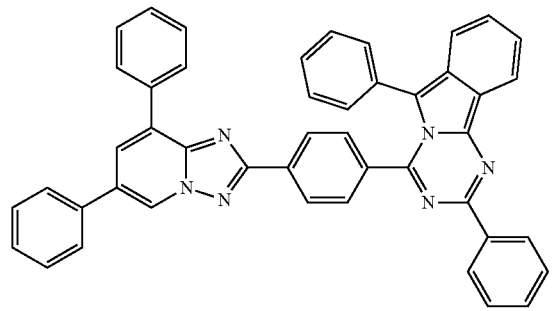
CJHP163
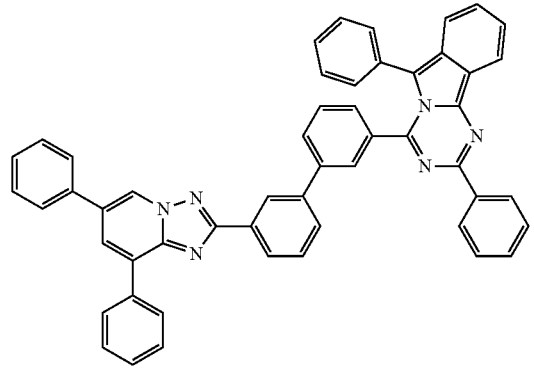

CJHP164
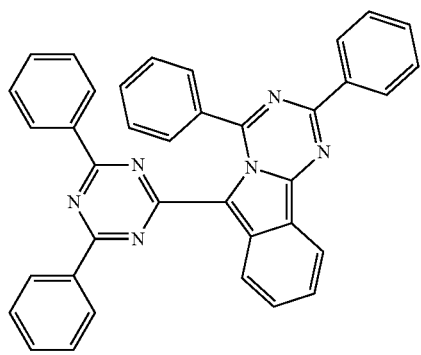
CJHP165
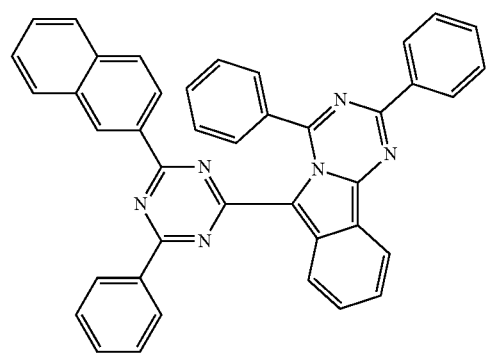
CJHP166
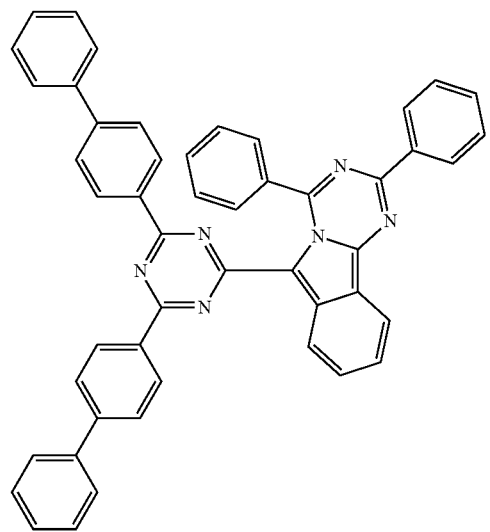
CJHP167
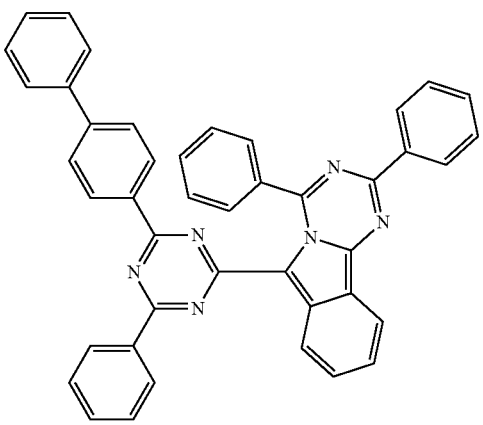
CJHP168
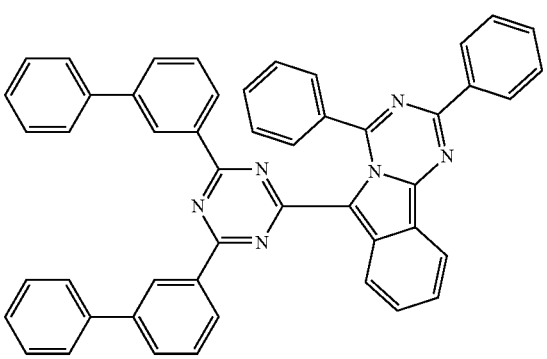
CJHP169
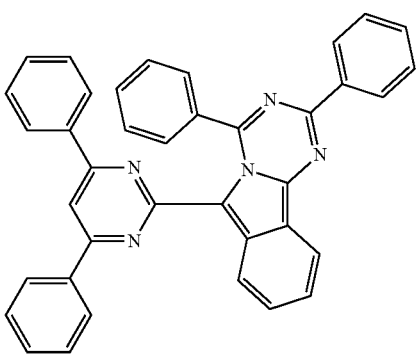
CJHP170

-continued
CJHP171
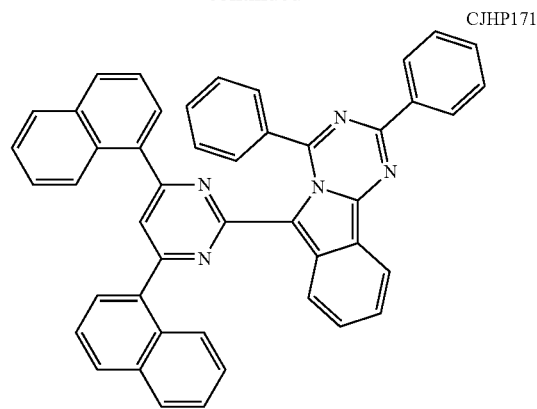
CJHP172
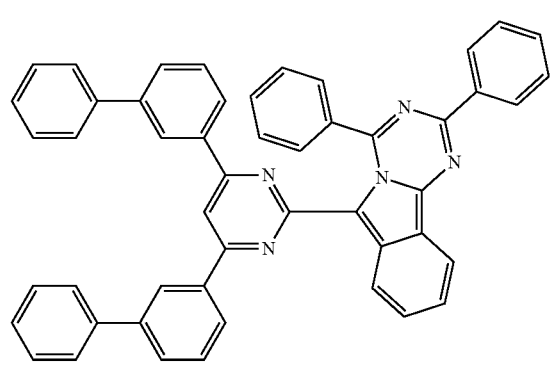
CJHP173
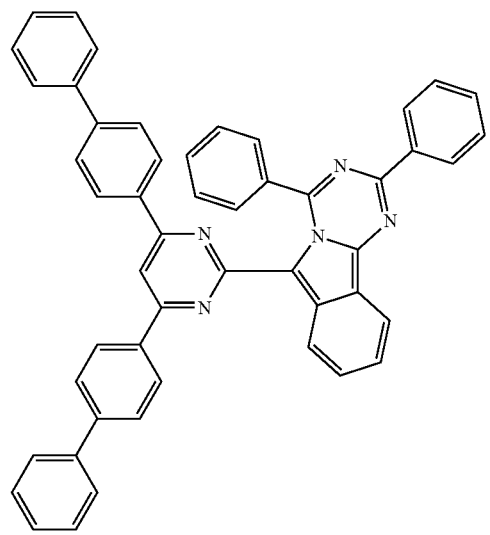
-continued
CJHP174
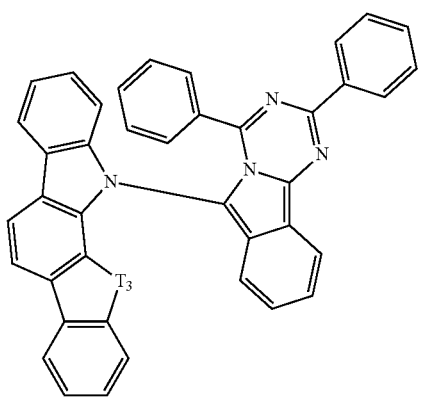
CJHP175
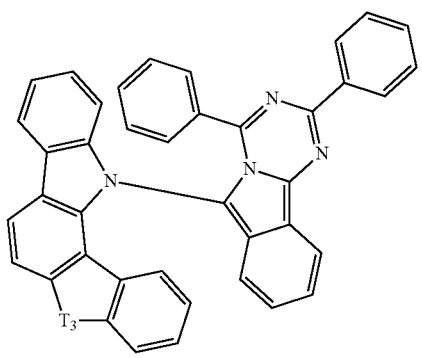
CJHP176
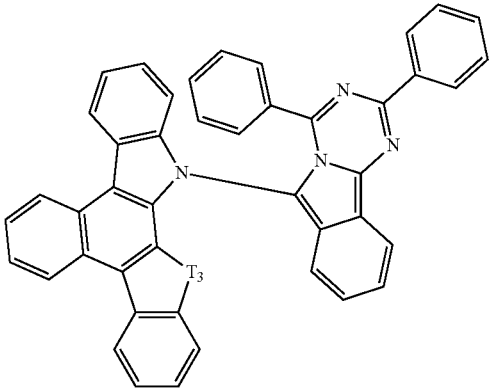
CJHP177
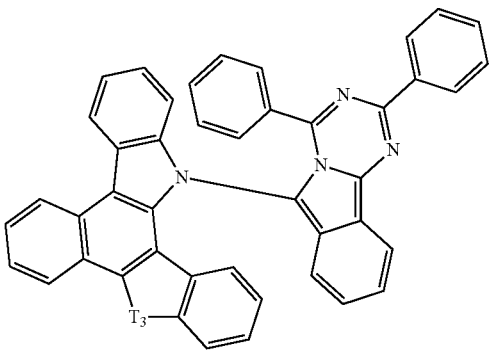

CJHP178
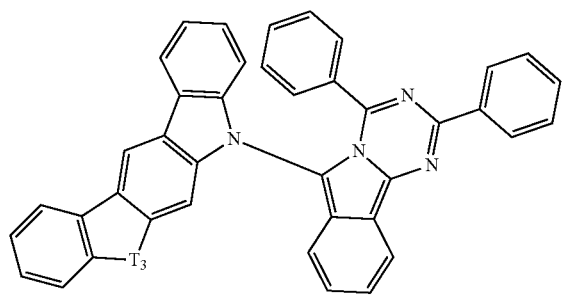
CJHP179
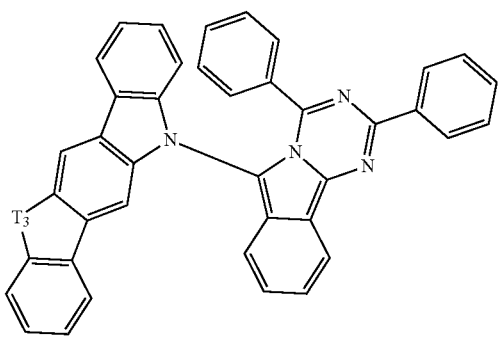
CJHP180
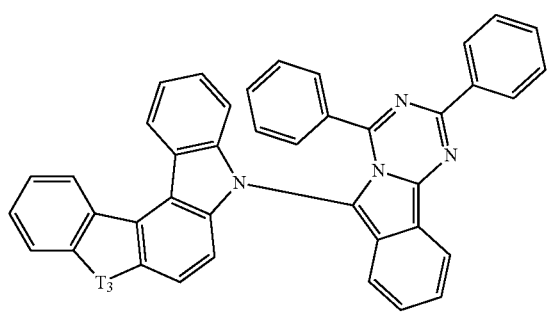
CJHP181
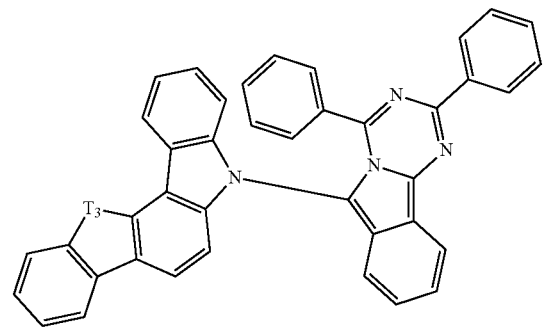
CJHP182
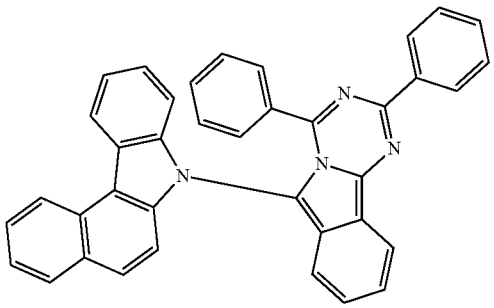
CJHP183
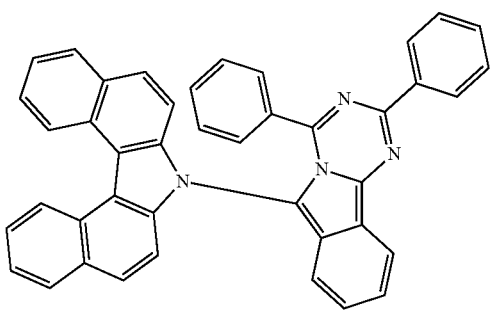
CJHP184
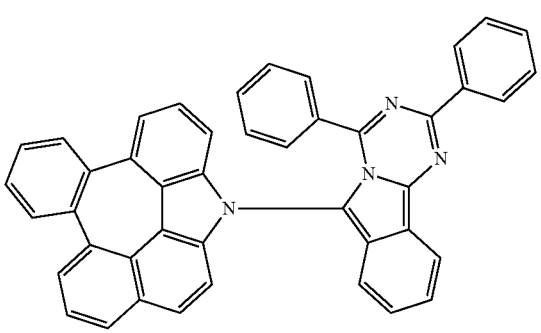
CJHP185
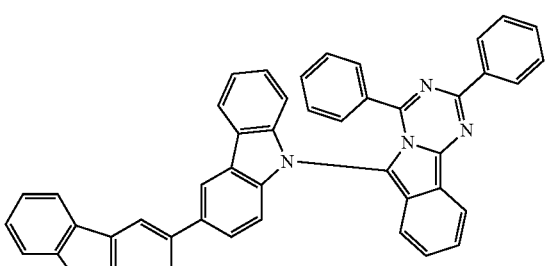
CJHP186
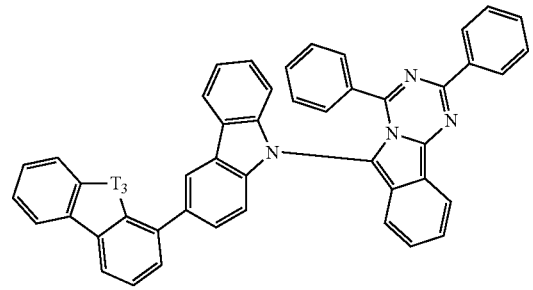

-continued
CJHP187
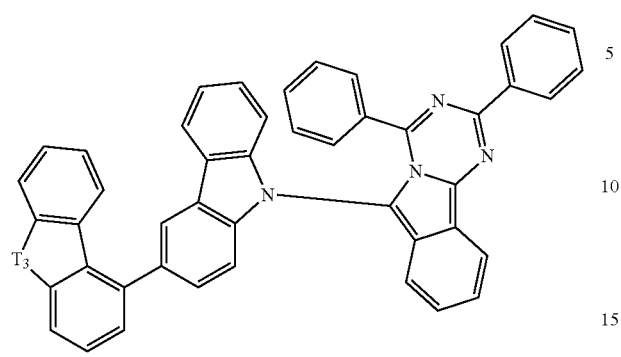
CJHP191
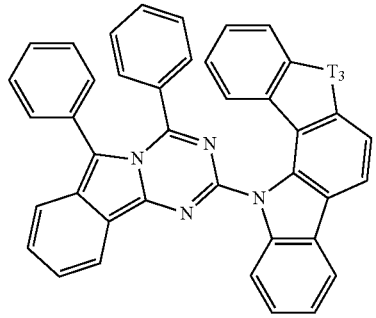
CJHP188
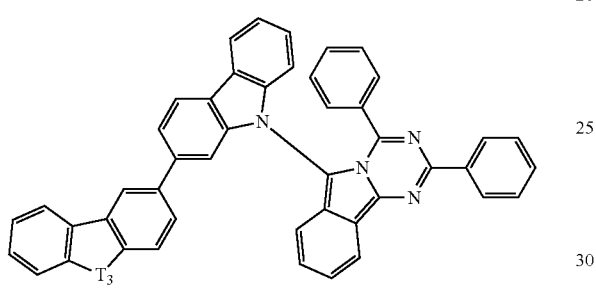
CJHP192
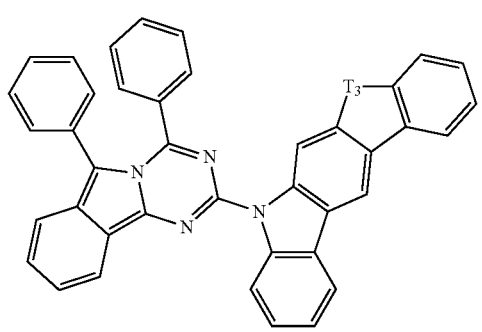
CJHP189
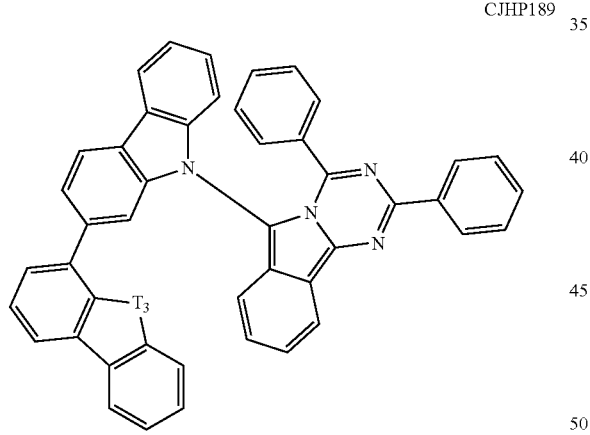
CJHP193
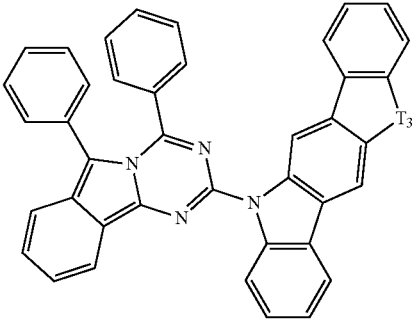
CJHP190
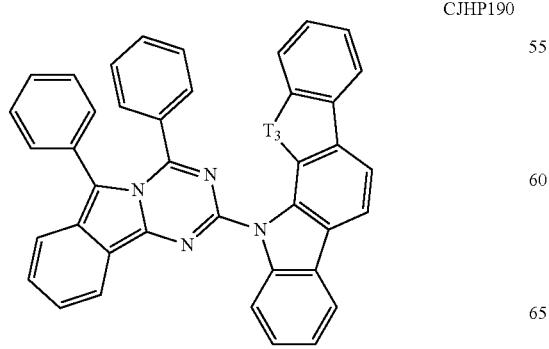
CJHP194
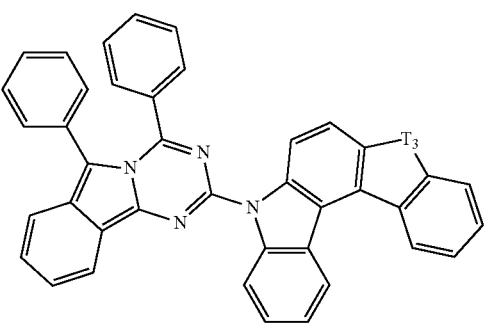

CJHP195
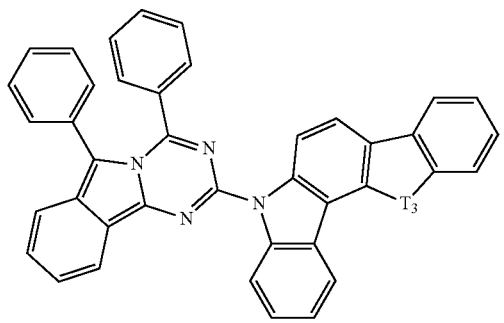
CJHP199
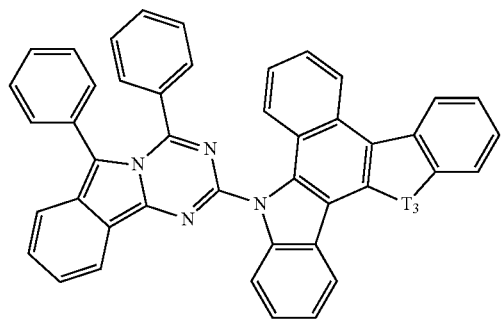
CJHP196
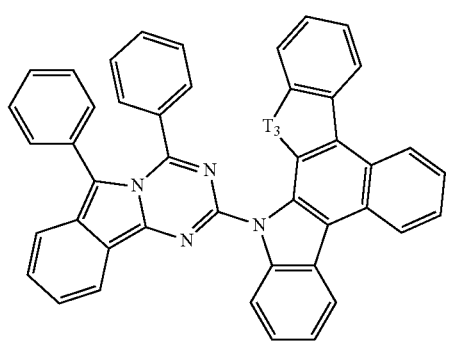
CJHP200
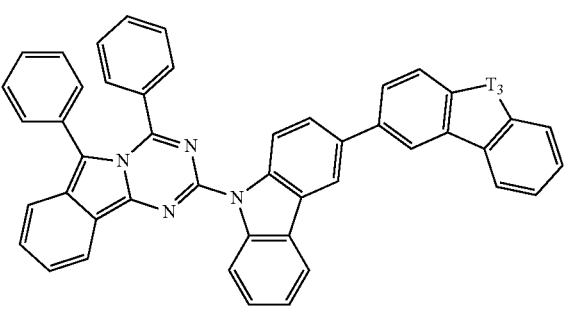
CJHP197
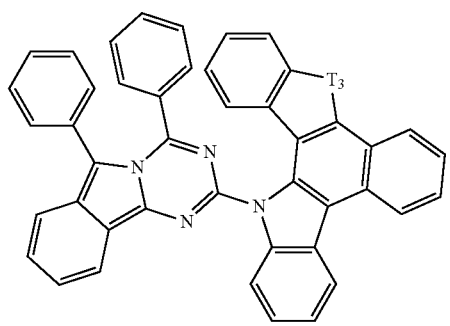
CJHP201
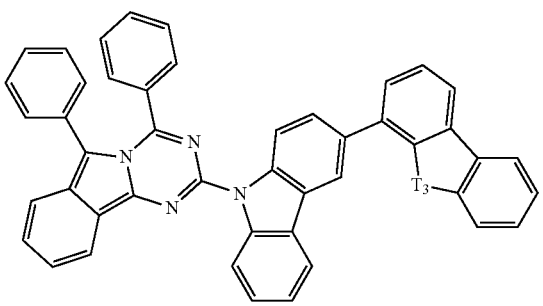
CJHP198
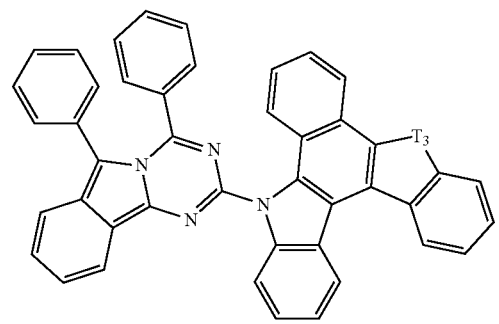
CJHP202
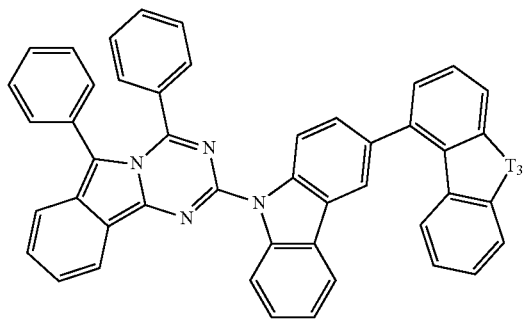

CJHP203
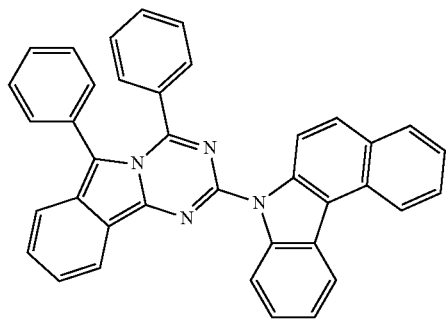
CJHP204
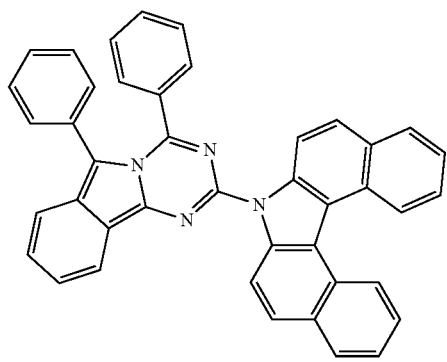
CJHP205
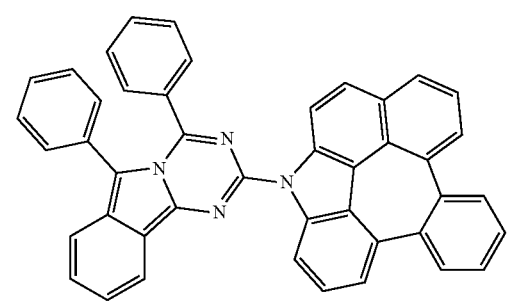
CJHP206
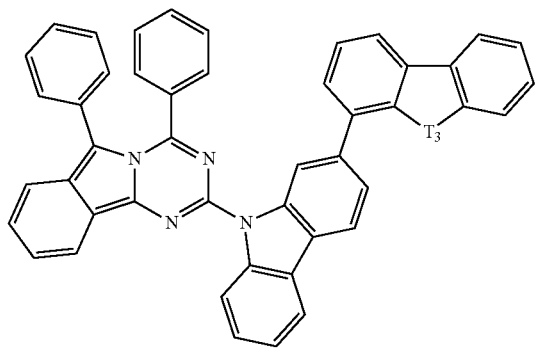
CJHP207
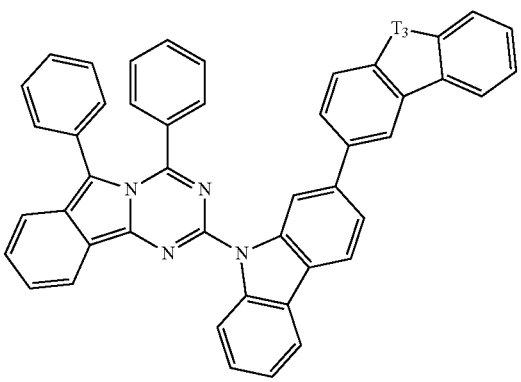
CJHP208
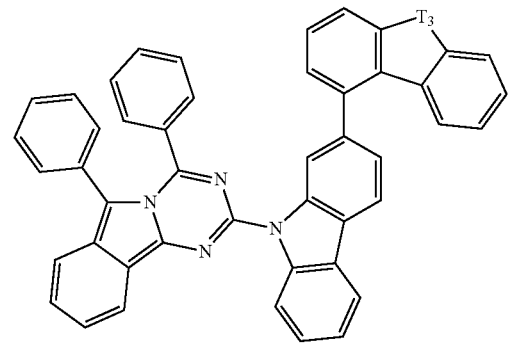
CJHP209
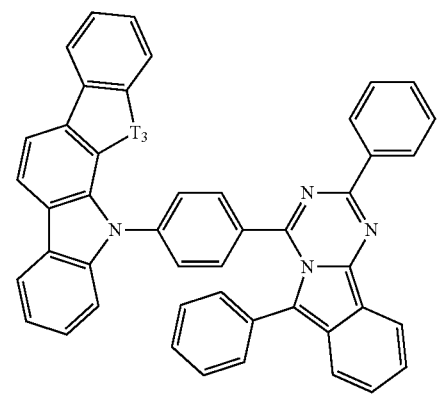
CJHP210
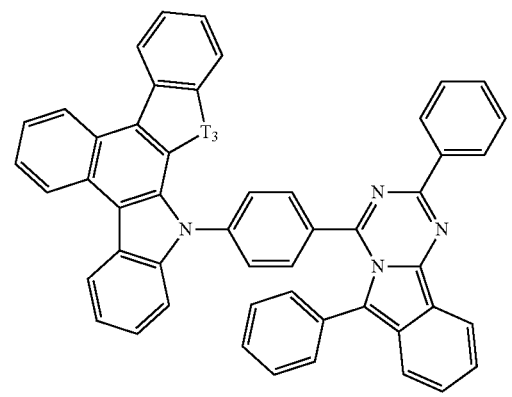

CJHP211
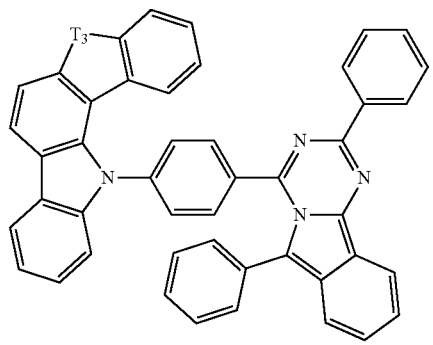
CJHP215
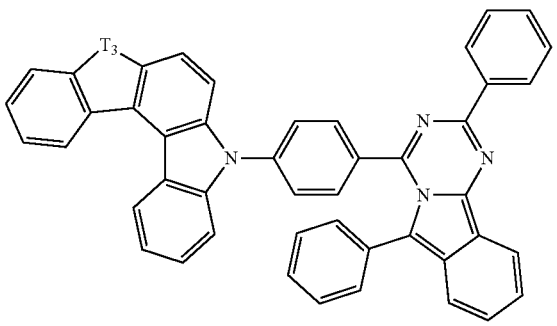
CJHP212
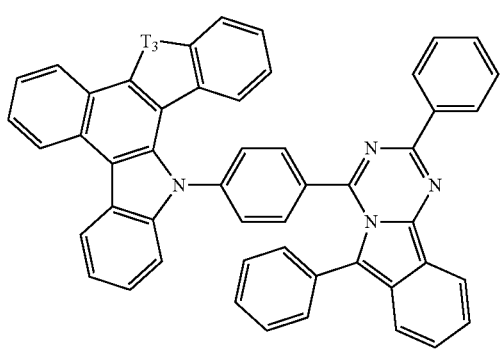
CJHP216
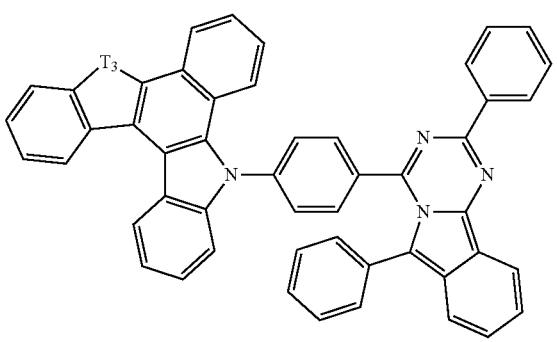
CJHP213
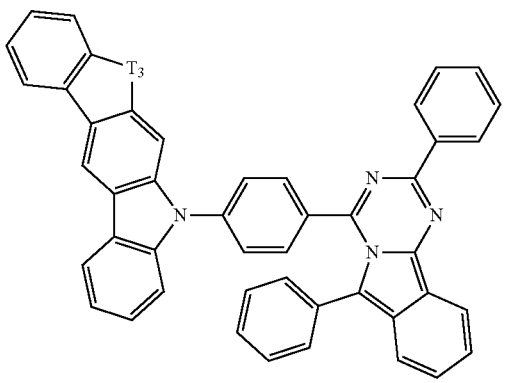
CJHP217
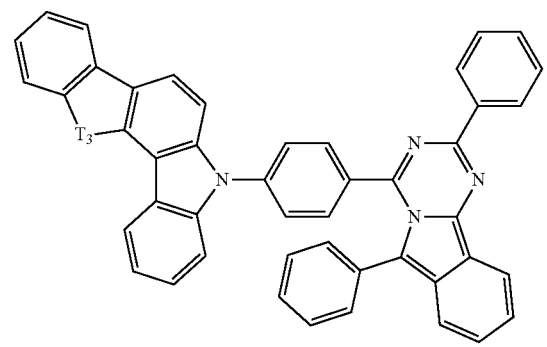
CJHP214
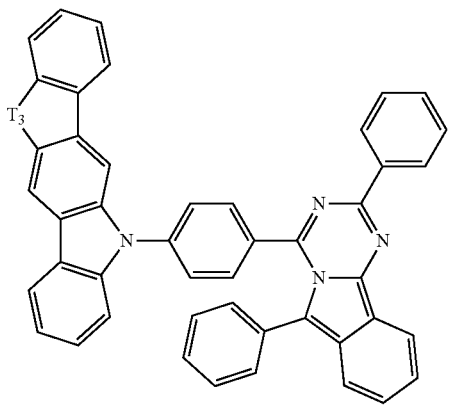
CJHP218
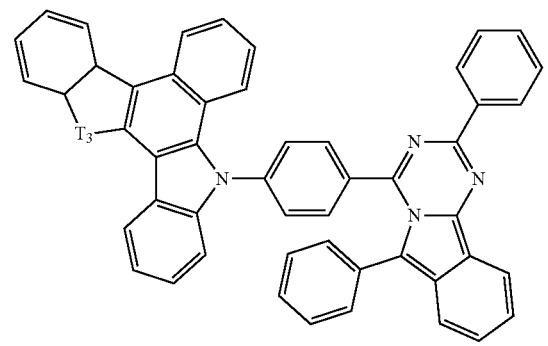

CJHP219
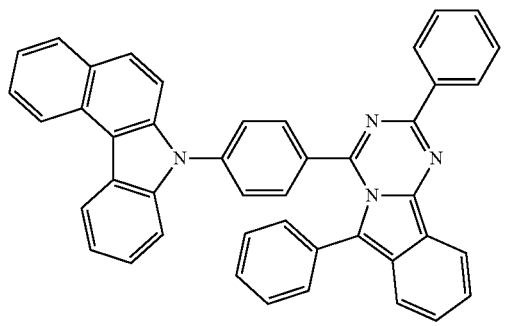
CJHP220
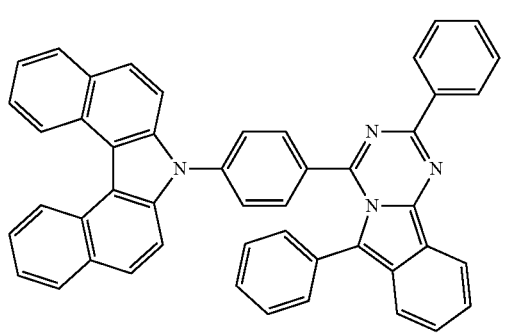
CJHP221
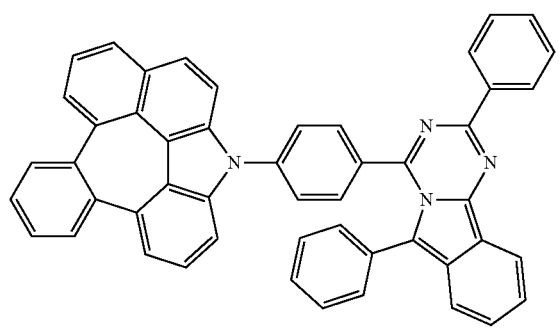
CJHP222
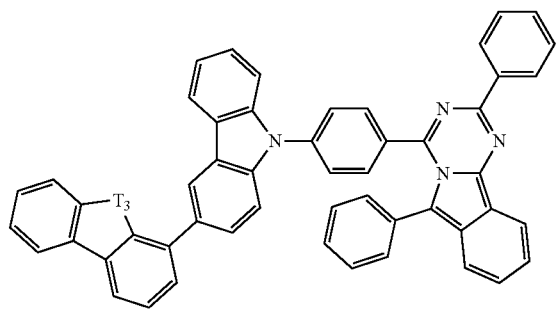
CJHP223
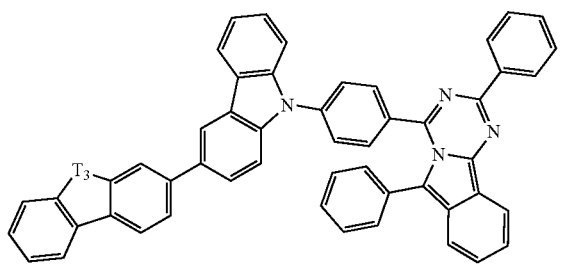
CJHP224
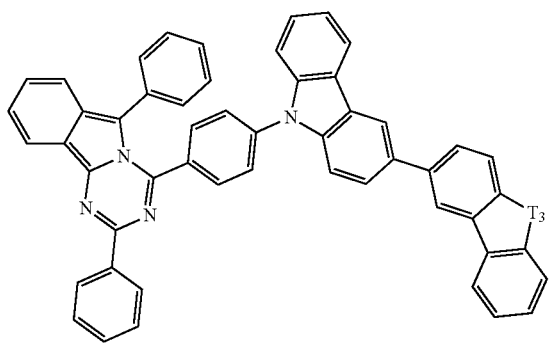
CJHP225
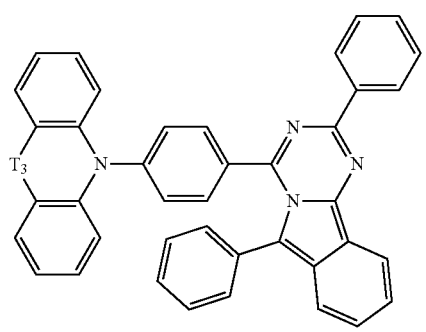
CJHP226
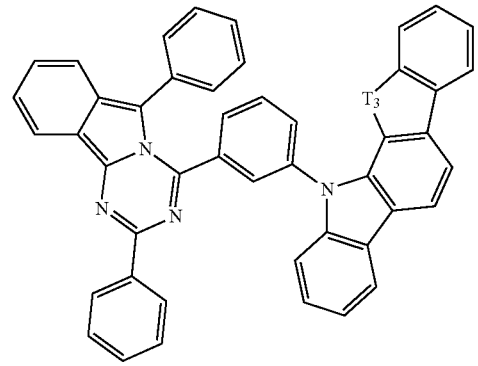
CJHP227
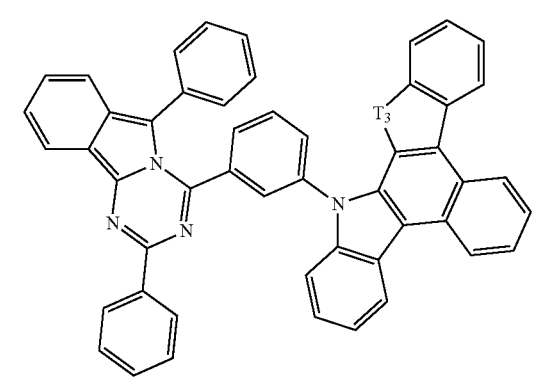

CJHP228
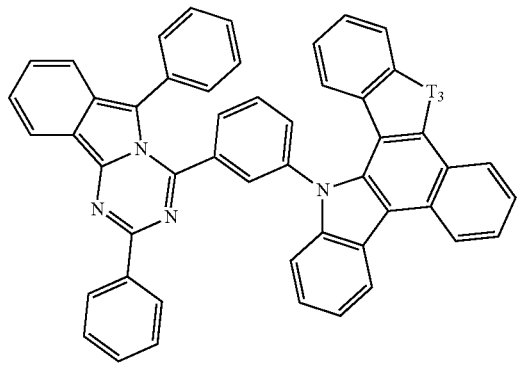
CJHP229
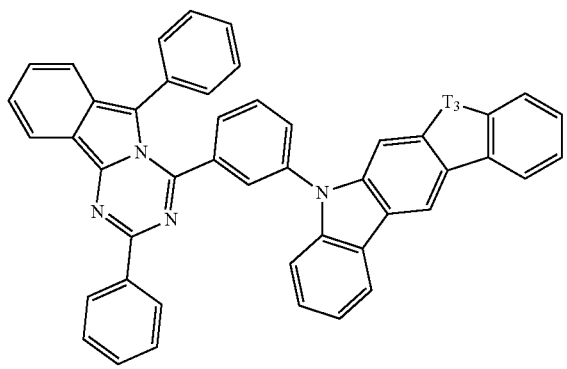
CJHP230
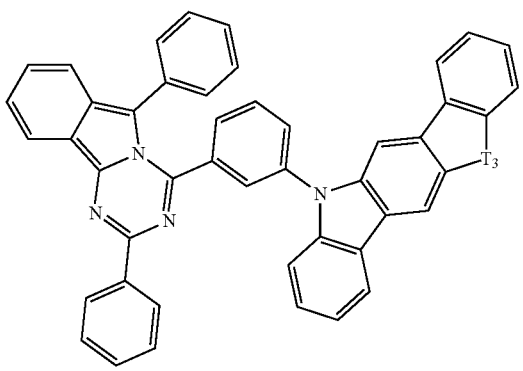
CJHP231
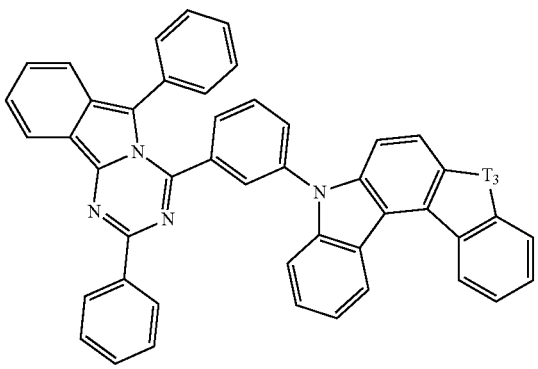
CJHP232
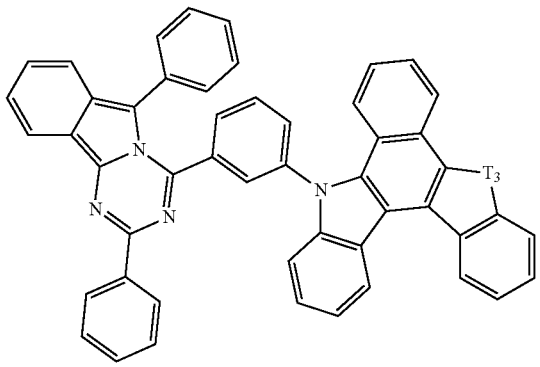
CJHP233
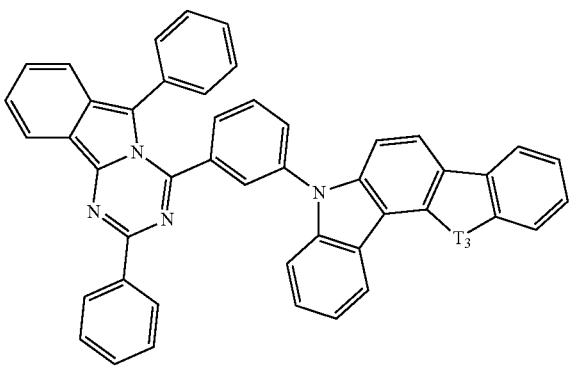
CJHP234
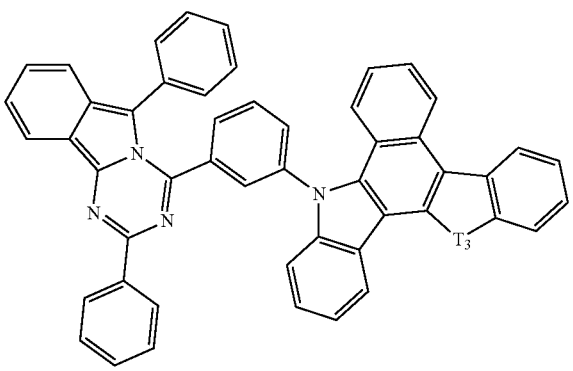
CJHP235
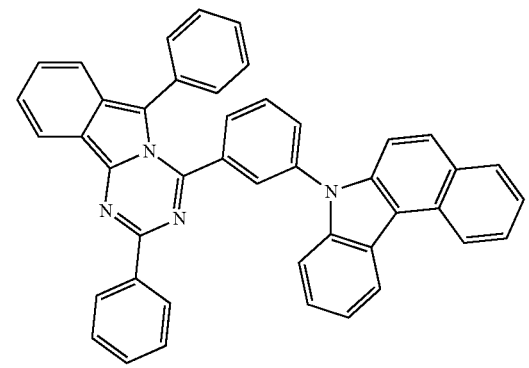

CJHP236
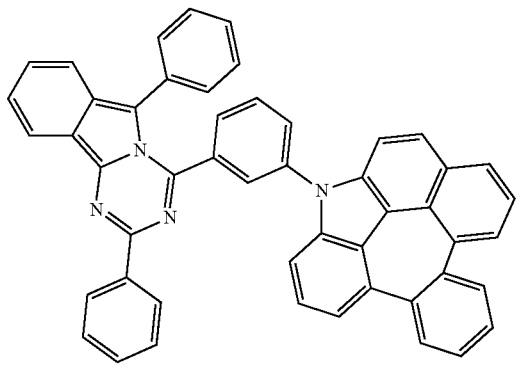
CJHP240
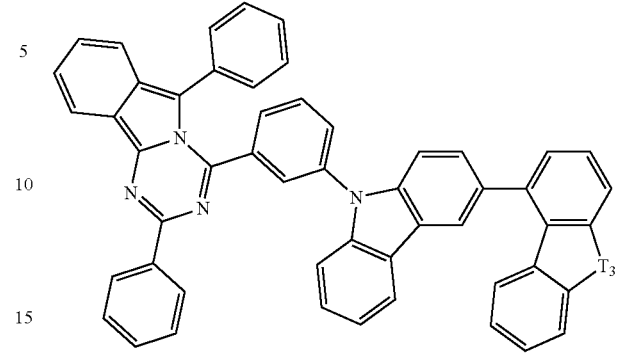
CJHP237
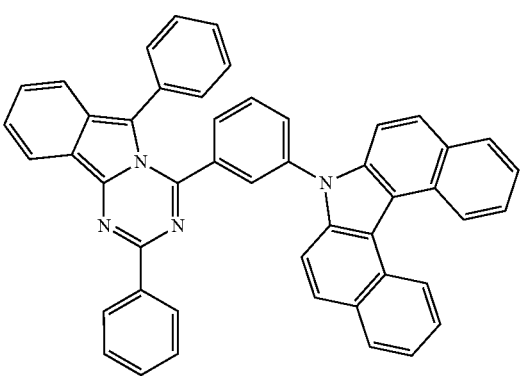
CJHP241
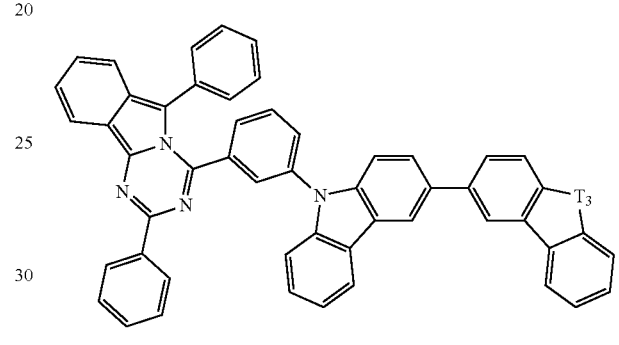
CJHP238
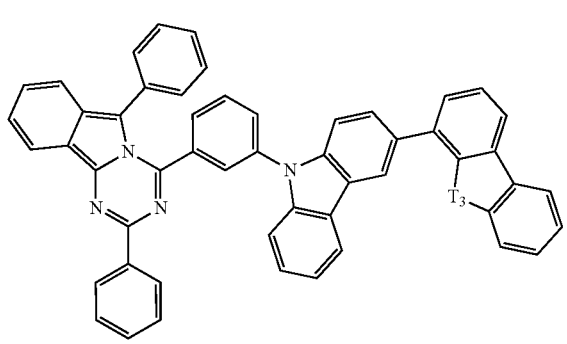
CJHP242
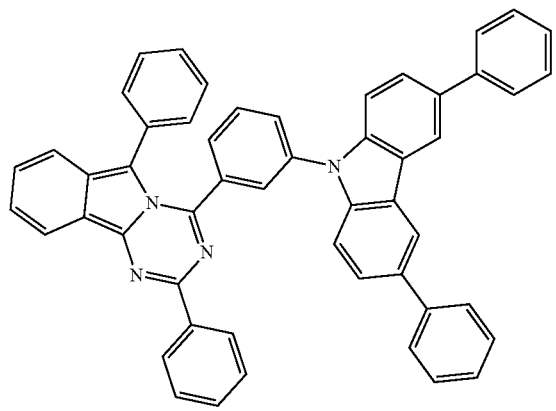
CJHP239
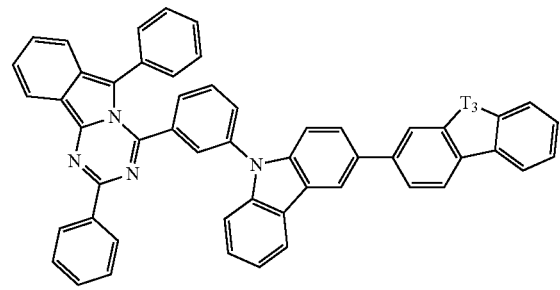
CJHP243
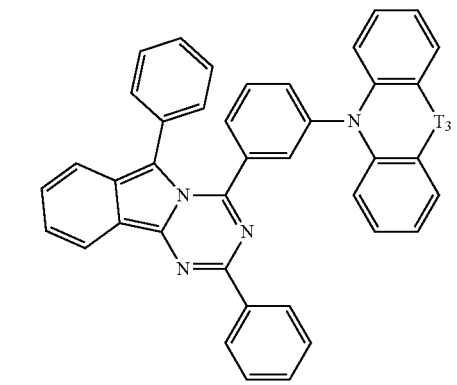

CJHP244
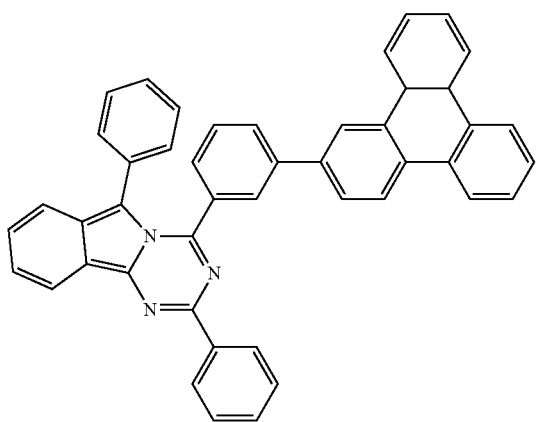
CJHP245
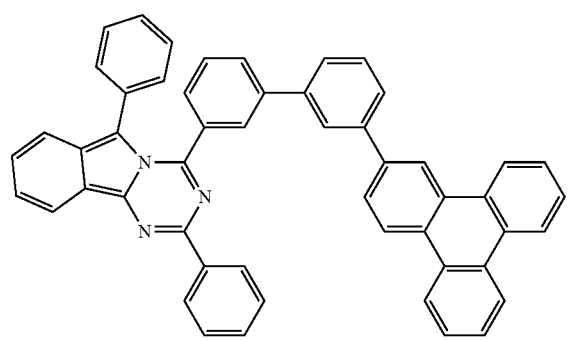
CJHP246
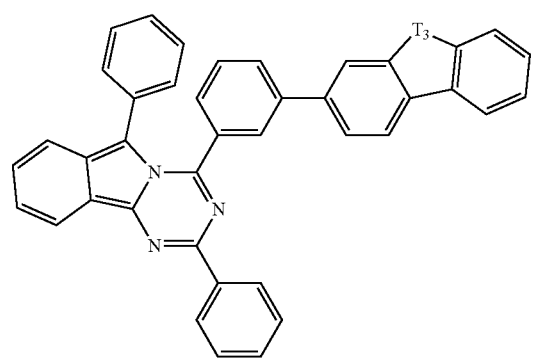
CJHP247
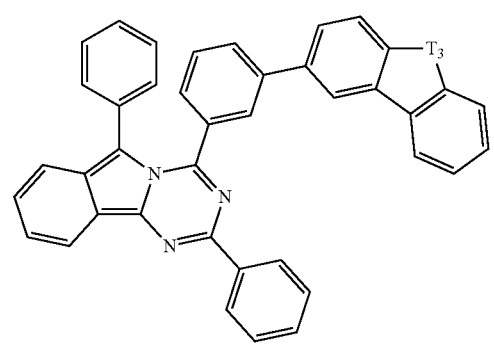
CJHP248
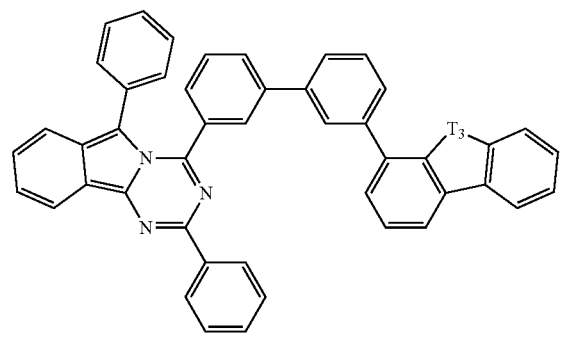
CJHP249
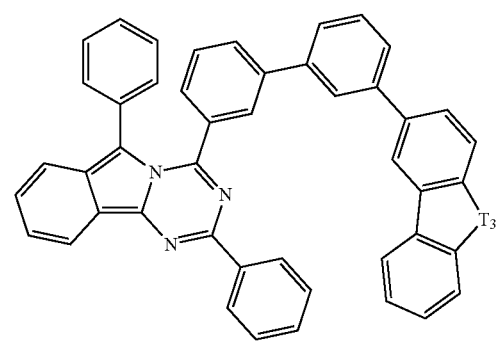
CJHP250
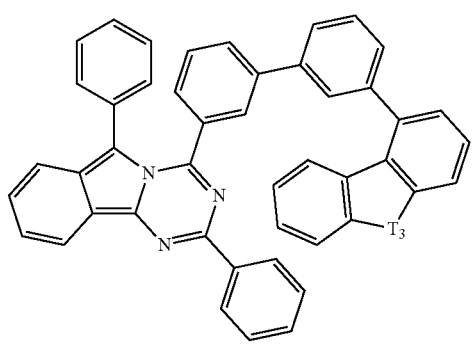
CJHP251
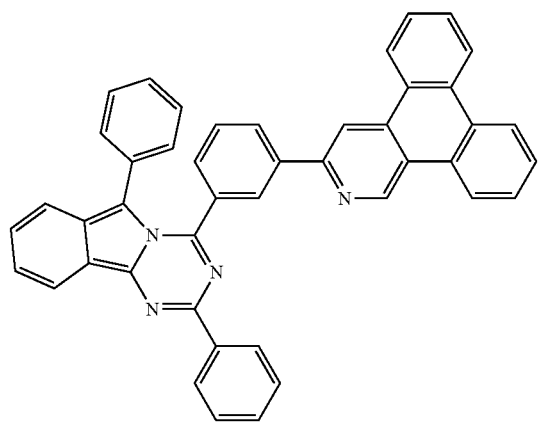

CJHP252

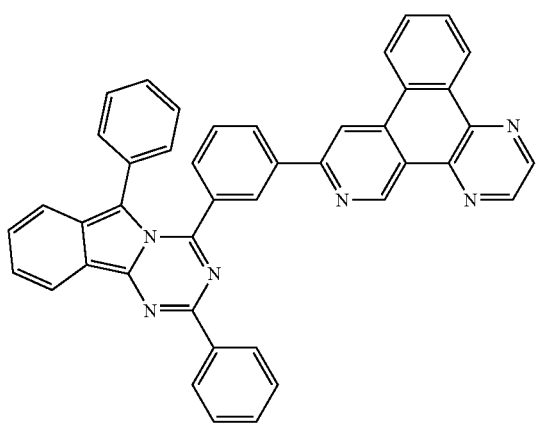

wherein T3 is *—O—*, *—S—* or one of the following structures:

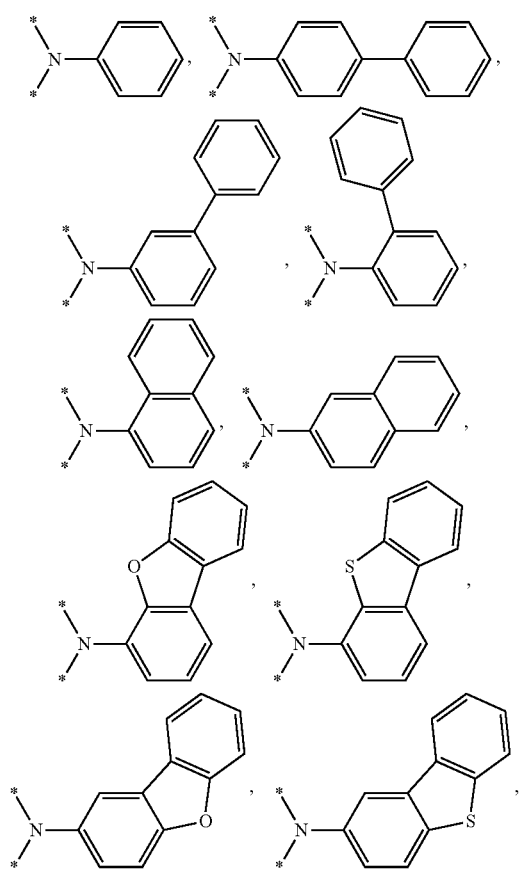

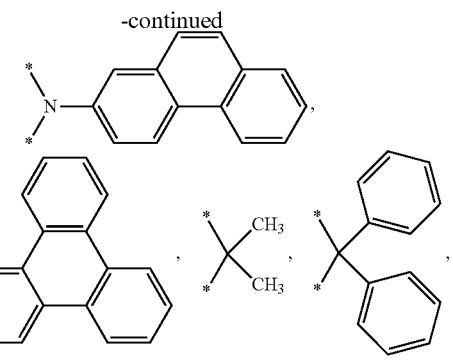

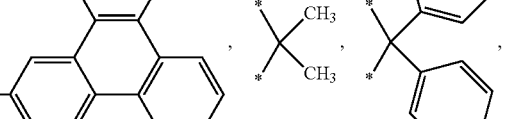

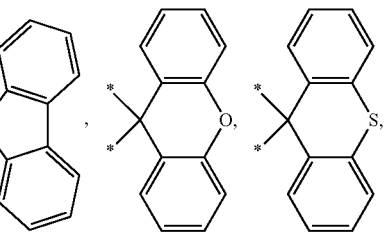

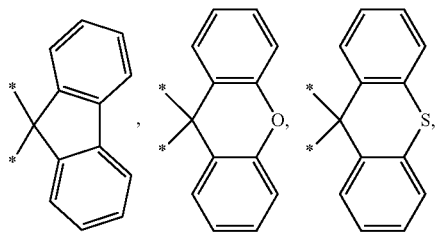

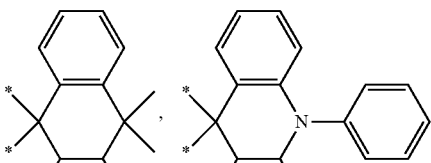

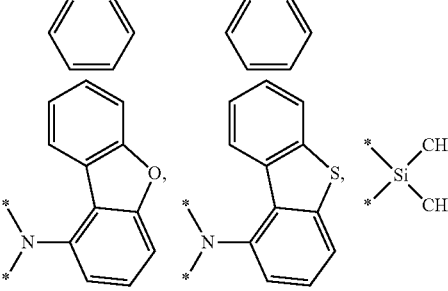

and

*— and —* indicate a connection bond.

4. An organic electroluminescent material, wherein the material comprises the organic compound according to claim 1.

5. An organic electroluminescent element, comprising a first electrode, a second electrode, one or more organic layers arranged between the first electrode and the second electrode, wherein the organic layer comprises the organic compound according to claim 1.

6. The organic electroluminescence element according to claim 5, wherein the organic layer is an emission layer, an electron transport layer, an electron injection layer, an electron transport auxiliary layer or an electron blocking layer.

7. The organic electroluminescence element according to claim 6, wherein the organic compound is a host substance of the emission layer.

* * * * *